(12) United States Patent
Roizman et al.

(10) Patent No.: US 6,340,673 B1
(45) Date of Patent: *Jan. 22, 2002

(54) METHOD OF TREATING TUMORIGENIC DISEASE

(75) Inventors: Bernard Roizman; Joany Chou, both of Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/283,471

(22) Filed: Apr. 1, 1999

Related U.S. Application Data

(60) Continuation of application No. 08/483,533, filed on Jun. 7, 1995, which is a division of application No. 08/419,853, filed on Apr. 11, 1995, now abandoned, which is a division of application No. 07/861,233, filed on Mar. 31, 1992, now abandoned.

(51) Int. Cl.[7] .................... A61K 48/00; C12N 15/63; C12N 15/85
(52) U.S. Cl. ................. 514/44; 435/320.1; 435/325; 435/375; 435/172.3
(58) Field of Search .................... 514/44; 435/320.1, 435/375, 325, 172.3

(56) References Cited

U.S. PATENT DOCUMENTS

| | | | |
|---|---|---|---|
| 4,769,331 A | 9/1988 | Roizman et al. | 435/69.1 |
| 5,328,688 A | 7/1994 | Roizman | 424/205.1 |
| 5,360,893 A | 11/1994 | Owens et al. | 530/350 |
| 5,585,096 A | 12/1996 | Martuza et al. | 424/93.2 |
| 5,593,879 A | 1/1997 | Stellar et al. | 435/240.1 |

FOREIGN PATENT DOCUMENTS

| | | |
|---|---|---|
| EP | 243155 | 10/1987 |
| EP | 453242 | 10/1991 |
| WO | WO 92/04050 | 3/1992 |

OTHER PUBLICATIONS

Ackerman et al., *J. Virology*, 58(3):843–850 (Jun., 1986).
Ackermann et al., *J. Virol.*, 52:108–118 (1984).
Barinaga, M., *Science*, 263:754–756 (1994).
Batistatou, A. et al., *J. Cell Biology*, 115(2):461–471 (Oct., 1991).
Brown, D., *The Washington Post*, A22 Friday, Dec. 8, 1995.
Centifanto–Fitzgerald et al., *J. Exp. Med.*, 155:475–489 (Feb., 1982).
Chambers, R. et al., *Proc. Natl. Acad. Sci.*, USA, 92:1411–1415 (Feb., 1995).
Chou et al., *Biochemistry*, Report, Jan. 8, 1991.
Chou et al., *J. Cell. Biochem.*, Keystone Symposia, Supplement 10C, Feb. 21–Mar. 7, 1992, Abstract N303, p. 136.
Chou et al., *Cell*, 41:803–811 (Jul., 1985).
Chou et al., *J. Virology*, 64(3):1014–1020 (Mar., 1990).
Chou et al., *J. Virology*, 57(2):629–637 (Feb., 1986).
Chou, et al., *Proc. Natl. Acad. Sci.* (USA) 89:3266–3270 (1992).
Chou, J. et al., *Science*, 250:1262–1266 (Nov., 1990).
Clem et al., *Science*, 254:1388–1399 (1991).
Coghlan, A., *New Scientist*, pp. 14–15 (Nov., 1995).
Corey et al., *N. Engl. J. Med.*, 314:686–691 (1986).
DeLuca et al., *J. Virol.*, 56:558–570 (1985).
Ejercito et al., *J. Gen. Virol.*, 2:357–364 (1968).
Gagliardini, V. et al., *Science*, 263:826–828 (1994).
Gregory et al., *Nature*, 349:612–614 (Feb., 1991).
Hammang, J.P., Bristol–Meyers Squibb, Phar. Research Inst., Research Report, Feb. 7, 1992.
Hayward et al., *Proc. Natl. Acad. Sci.*, USA, 72(11):4243–4247 (Nov., 1975).
Henderson, S., *Cell*, 65:1107–1115 (Dec., 1991).
Honess et al., *J. Virology*, 12(6):1347–1365 (Dec., 1973).
Hubenthal–Voss et al., *J. Virology*, 62(2):454–462 (Feb., 1988).
Itoh et al., *Cell*, 66:233–243 (1991).
Javier et al., *J. Virology*, 61(6):1978–1984 (Jun., 1987).
Johnson et al., *Neurobiol. of Aging*, 10:549–552 (1989).
Katz et al., *J. Virol.*, 64(9):4288–4295 (Sep., 1990).
Kyte et al., *J. Mol. Biol.*, 157:105–132 (1982).
Loo et al., *J. Neuroscience Research*, 28:101–109 (1991).
Lord et al., *Nucleic Acid Res.*, 18:2823 (1990).
Mackem et al., *J. Virol.*, 44:934–947 (1982).
Markert et al., Dept. of Neuro. Harvard Med. School, Research Manuscript, 18 pages (1992).
McGeoch et al., *J. Gen. Virol.*, 69:1531–1574 (1988).
McGoech, D. et al., *Journal of General Virology*, 72:3057–3075 (1991).
Meignier et al., *J. Infectious Diseases*, 158(3):602–614 (Sep., 1988).

(List continued on next page.)

Primary Examiner—Karen M. Hauda
Assistant Examiner—Anne Marie S Beckerleg
(74) Attorney, Agent, or Firm—Marshall, O'Toole, Gerstein, Murray & Borun

(57) ABSTRACT

The present invention relates to methods of treatment of programmed cell death (apoptosis) through the use of the HSV-1 gene $\gamma_1 34.5$ or the product of its expression, ICP34.5. The gene and its expression have been demonstrated to be required for HSV-1 neurovirulence, and in particular, to act as an inhibitor of neuronal programmed cell death which allows for viral replication. Use of the gene therapy, or the protein itself, can be expected to result in inhibition of programmed cell death in various neurodegenerative diseases. This invention also relates to novel vectors for gene therapy, including modified herpes virus. Methods are presented for conducting assays for substances capable of mimicing, potentiating or inhibiting the expression of $\gamma_1 34.5$ or the activity of ICP34.5. Also, methods are disclosed for the treatment of tumorogenic diseases, including cancer, and for treatment of herpes and other viral infections using inhibitors of $\gamma_1 34.5$ expression or ICP34.5 activity.

6 Claims, 19 Drawing Sheets

OTHER PUBLICATIONS

Morris, C. (Ed.), *Academic Press Dictionary of Science and Technology*, Academic Press, Harcourt Brace Jovanovich, Publishers, pp. 917 and 2276 (1992).
Mulligan, R.C., *Science*, 260:926–930 (May, 1993).
Orkin et al., "Report and Recommendations of the Panel to Assess the NIH Investment in Research on Gene Therapy" (Dec., 1995).
Peppel et al., *BioTechniques*, 9:711–712 (1990).
Post et al., *Cell*, 25:227–232 (Jul., 1981).
Rawson et al., *J. Cell. Biol.*, 113:671–679 (1991).
Renfranz et al., *Cell*, 66:713–729 (1991).
Roizman, *Field's Virology*, Second Edition, 64:1787–1793 (1990).
Roizman, *Field's Virology*, Second Edition, 5:87–94 (1990).
Roller et al., *J. Virol.*, 65:5873–5879 (1991).
Ryder et al., *J. Neurobiology*, 21(2):356–375 (1990).
Sentman et al., *Cell*, 67:879–888 (Nov., 1991).
Snyder et al., *Cell*, 68:33–51 (1992).
Strasser et al., *Cell*, 67:889–899 (1991).
Taha et al., *J. Gen. Virol.*, 70:705–716 (1989).
Thompson et al., *Virology*, 172(2):435–450 (1989).
Wadsworth et al.,*J. Virology*, 15(6):1487–1497 (Jun., 1975).
Whitley, R.J., *J. Clin. Invest.*, 91:2387–2843 (Jun., 1993).
Williams, *Cell*, 85:1097–1098 (1991).
Williams, G.T., *Cell*, 65:1097–1098 (Jun., 1991).

Fig. 1a

```
                         DR1
F:   TTTAAAGTCGGGGGC--GCAGCCCGGGCCCCCGCGGGCCCGAGACGAGGAGTTAGACAGGCAAGCACTACTGCCTCTGCAC    82
17:              CG T          GG              T
MGH:             CAC-A         GG              T
CVG:             CGC-          GG              T

F:   GCACATGCTTGCCTGTCAAACTCTACCACCCCGGCACGCTCTCTGTCTCCATGCCGCCGCC---ATCGCGGCCCCC         163
17:
MGH:                                                             GCC
CVG:                                                             GCC

F:   GCCGCCCCCGCCGCCCGGGCCCCACGGGCCCGTCCCAACCGCACAGTCCCAGGTAACCTCCACGCCCAACTCGGAACCGCGG   247
17:
MGH:                       G                                                         T
CVG:                       G                                                         T

F:   TCAGGAGCGCGCCCCGCCGCCCCGCCCCCCGCCGCCCTTCTTGTTCGCTGCTGCCAGTGGC                        331
17:                                       G
MGH:                                     G-G
CVG:                                     G-G                           G

F:   TCCACGTTCCCGAGTCCGCGTCCGACGATGACGACGACTGGCCGGACAGCCCCGAGCGGCCAGAGGCCC                415
17:                                                                  T
MGH:
CVG:

F:   GGCCCACCGCCGCCGCCCCCCGCCCCC-GGTCCCC-ACCGCCCCGGCGCGCGGGCCCGGGGGGCTAACCCCTCCACCCCCC    497
17:                              C G  C          T                G
MGH:                             - -               A              G
CVG:                             - -                              G

F:   CTCACGCCCCCTTCCGCCTTCCGCCTCCGCCTCGCCTGCCGCGTCACCGCAGAGCACCTGGGCGCGCCTGCCTGCGACG      581
17:                G                                                G
MGH:                                                                  G
CVG:                                                                  G

F:   CGCGGGCGGGGAGGGGCGCCGGAGCCCCCGCGACCCCCGCGACCCCCGCGACCCCCGCGACCCCCGCGACCCCCGACCCCC   *665
17:                A                    *       *        *        *        *
MGH:                                    *                                  *          ---
CVG:                                                                       *          ---
```

Fig. 1b

```
            *                                                              *                              749
F:     CGCGACCCCCGCGACCCCCGCGACCCCCGCGACCCCCGCGCTTCTGCCCCACGTCCGGGTGCGCCACCTGGT
17:    ------------------------------------
MGH:   ------------------------------------
CVG:   ------------------------------------

833
F:     CTGGGCCTCGGCCGCGCCGCCTGGCCGCGGCCGCGGCTCGTGGGCCCGGAGCGGCGACCGGAGCTCGGTTCCGGCCGGGTGGC
17:
MGH:
CVG:

917
F:     GGAGGCCGAGGCGGTCATCGGGGCCGTGCCTGGGGCCCTGGGGCCCGAGGCCCGTGCCCGGGCCCTGGCCCGCGGAGCCCGGCCCGGAACTC
17:
MGH:                                                                    C        A          C
CVG:

1001
F:     GGTCTAACGTTACACCCGAGGCGGGCTGGGTCTTCCGCGAGCTCCGCGGAGCTCCGCACCAAGCCGTCTCCGGAGAGACGAT
17:                                                                 A
MGH:
CVG:                                                                A

1083
F:     GGCAGGAGCCGCATATATACGCTGGGAGCCGGCCCGCCCC--GAGGGGGGCCCGCCCTCGGAGGGGCGGGACTGGCCAATCG
17:                                          T     A      T ACAG         -    -     -
MGH:
CVG:

1167
F:     GCGGGCCGCCAGCGCGCGGGGCCCGGCCAACCAGCGTCCGCCGAGTCTTCGGGGCCCCACTGGGCGGGAGTTACCGCCCA
17:                                                                            T
MGH:
CVG:

1251
F:     GTGGGCCGGCCGCGCCACTTCCCGGTATGGTAATTAAAAACTTACAAGAGAGCCTTGTTCCGCTTCCCGGTATGGTAATTAGAAA
17:    A                                                      T AC C
MGH:                                                          G           T AC C
CVG:                                                          G

1335
F:     CTCATTAATGGGCGGCCCGCGCCCTTCCCGCTTCCGGCAATTCCCGCGGCCCTTAATGGGCAACCCCGTATTCCCGCCT
17:
MGH:                                                          G
CVG:                                                          G
```

```
                                                                                   24
MetAlaArgArgArgArg---HisArgGlyProArgArgProArgProProGlyProThrGlyAlaValProThr
                   Arg
                   Arg
                                                                                   49
AlaGlnSerGlnValThrSerThrProAsnSerGluProAlaValArgSerAlaProAlaAlaAlaProProPro
                                          Val              ------------
                                          Val
                                                                                   74
ProProAlaSerGlyProProProSerCysSerLeuLeuLeuArgGlnTrpLeuHisValProGluSerAlaSer
        Gly
---------Gly
        Gly                                                       Gln
                                                                                   99
AspAspAspAspAspAspAspTrpProAspSerProProProGluProAlaProGluAlaArgProThrAlaAla
                                                                 Ser

124
AlaProArgProArgSerProProProGlyAlaGlyProGlyGlyGlyAlaAsnProSerHisProProSerArg
           ProGlyProHisArgProAlaTrpAlaArgGlyAlaGlyLeuThrProProThrProProArg
                                                   Asp
                                                                                  149
ProPheArgLeuProProArgLeuAlaLeuArgLeuArgValThrAlaGluHisLeuAlaArgLeuArgLeuArg
AlaProSerAlaPheArgArgAlaSerProSerAlaCysAlaSerProArgSerThrTrpArgAlaCysAlaCys

*    *    *    *    * 174
ArgAlaGlyGlyGluGlyAlaProGluProProAlaThrProAlaThrProAlaThrProAlaThrProAlaThr
AspAlaArgAlaGlyArgGlyArgArgSerProProArgProProArgProProArgProProArgProProArg
                                 Lys

*    *    *    *    *                                                           199
ProAlaThrProAlaThrProAlaThrProAlaThrProAlaThrProAlaArgValArgPheSerProHisVal
Pro-----------------------------------------------ProArgGlyCysAlaSerArgProThr
           -----------------------------------------
```

```
                                                                                               224
ArgValArgHisLeuValValTrpAlaSerAlaAlaArgLeuAlaArgArgGlySerTrpAlaArgGluArgAla
SerGlyCysAlaThrTrpTrpSerGlyProArgProProAlaTrpArgAlaAlaAlaArgGlyProAlaSerGly

249
AspArgAlaArgPheArgArgArgValAlaGluAlaGluAlaValIleGlyProCysLeuGlyProGluAlaArg
ProThrGlyLeuGlySerGlyAlaGlyTrpArgArgProArgArgSerSerGlyArgAlaTrpGlyProArgPro
                                                                                               Lys
                              263
AlaArgAlaLeuAlaArgGlyAlaGlyProAlaAsnSerValOc
ValProGlyProTrpProAlaGluProAlaArgArgThrArgSerAsnValThrProGluAlaAlaTrpValPhe

ArgGlyAlaProGlySerSerAlaProSerArgSerProGluArgArgTrpGlnGluProArgIleTyrThrLeu

GlyAlaSerProProSerGlnGlyGlyProProArgGlyArgAspTrpProIleGlyGlyArgGlnArgGlyGly

AlaArgProThrSerValArgArgValPheGlyAlaArgProIleGlyArgGluLeuProProAsnGlyProGly

ArgProLeuProGlyMetValIleLysAsnLeuGlnGluAlaLeuPheArgPheProValTrpOc
```

METHOD OF TREATING TUMORIGENIC DISEASE

This is a continuation of U.S. application Ser. No. 08/483,533, filed Jun. 7, 1995, which is a divisional of U.S. application Ser. No. 08/419,853 filed Apr. 11, 1995 (now abandoned), which is a divisional of U.S. application Ser. No. 07/861,233 filed Mar. 31, 1992 (now abandoned).

BACKGROUND OF THE INVENTION

The government may own certain rights in the present invention pursuant to grants from the National Cancer Institute (CA474511 and from the National Institute for Allergy and Infectious Diseases (AI24009. and AI1588), and the United States Public Health Service.

FIELD OF THE INVENTION

The present invention is directed to methods for blocking or delaying programmed cell death, for delivery of gene therapy to specific cells, and for treatment of cancer and other tumorgenic diseases, as well as treatment of viral infections, through the potentiation of programmed cell death in tumor or viral host cells. The present invention is also directed to assays for candidate substances which can either inhibit, or potentiate programmed cell death.

Description of the Related Art a. Programmed Cell Death (Apoptosis)

In the last decade there has been increasing acceptance in the scientific community of the idea that cells may actually be internally programmed to die at a certain point in their life cycle. As an active cellular mechanism programmed cell death, is or apoptosis, has several important implications. First, it is clear that such an active process can provide additional means of regulating cell numbers as well as the biological activities of cells. Secondly, mutations or cellular events which potentiate apoptosis may result in premature cell death. Third, a form of cell death which is dependent on a specific active cellular mechanism can at least potentially be suppressed. Finally, an inhibition of preprogrammed cell death would be expected to lead to aberrant cell survival and could be expected to contribute to oncogenesis.

In general, apoptosis involves distinctive morphological changes including nuclear condensation and degradation of DNA to oligonucleosomal fragments. In certain circumstances it is evident that apoptosis is triggered by or is preceeded by changes in protein synthesis. Apoptosis appears to provide a very clean process for cellular destruction, in that the cells are disposed of by specific recognition and phagocytosis prior to bursting. In this manner cells can be removed from a tissue without causing damage to the surrounding cells. Thus, it can be seen that programmed cell death is crucial in a number of physiological processes, including morphological development, clonal selection in the immune system, and normal cell maturation and death in other tissue and organ systems.

It has also been demonstrated that cells can undergo apoptosis in response to environmental information. Examples include the appearance of a stimulus, such as glucocorticoid hormones for immature thymocytes, or the disappearance of a stimulus, such as interleukin-2 withdrawal from mature lymphocytes, or the removal of colony stimulating factors from hemopoietic precursors (for a review of literature see Williams, Cell, 85; 1097–1098, Jun. 28, 1991). Furthermore, it has recently been demonstrated that the response of removal to nerve growth factor from established neuronal cell cultures mimics target removal, or axiotomy, or other methods of trophic factor removal, and it has been postulated that the cellular mechanism involved in this response is a triggering of a suicide program or programmed cell death following the nerve growth factor removal. (See Johnson et al., Neurobiol. of Aging, 10: 549–552, 1989). The authors propose a "death cascade" or "death program", which envisions that trophic factor deprivation initiates the transcription of new mRNA and the subsequent translation of that mRNA into death associated proteins which act in sequence to ultimately produce "killer proteins". Such an intracellular mechanism seems to fit well with the characteristics of apoptosis discussed above, eg., death of specific cells without the release of harmful materials and without the disruption of tissue integrity. Furthermore, the authors indicate that inhibitors of macromolecular synthesis prevented the death of neurons in the absence of nerve growth factor.

Studies have been conducted to explore the possibility that tumor cells could be eliminated by artificially triggering apoptosis. The APO-1 monoclonal antibody can induce apoptosis in several transformed human B and T cell lines. The antibody binds to a surface protein and could act either by mimicking a positive death-inducing signal or by blocking the activity of a factor required for survival. Also, anti-FAS antibodies have similar effects, and the recent cloning and sequencing of the gene for the FAS antigen has shown that it is a 63 kilodalton transmembrane receptor. Itoh et al., Cell 66: 233–243 (1991).

However, it is important to note that neither APO-1 nor FAS can function exclusively as triggers for cell death. Both are cell surface receptors that may activate quite different responses under other circumstances. Moreover, these antigens are not confined to tumor cells and their effect on normal cells is certainly an important consideration, as is the possible appearance of variants that no longer display the antigens.

It has also been demonstrated that the cell death induced by a range of cytotoxic drugs, including several used in cancer therapy, has also been found to be a form of apoptosis. In fact, the failure of apoptosis in tumor cells could be of fundamental importance in contributing not only to the evasion of physiological controls on cell numbers, but also to resistance both to natural defenses and to clinical therapy.

It has also been demonstrated that expression of the bcl-2 gene can inhibit death by apoptosis. The bcl-2 gene was isolated from the breakpoint of the translocation between chromosomes 14 and 18 found in a high proportion of the most common human lymphomas, that being follicular B cell lymphomas. The translocation brings together the bcl-2 gene and imunoglobulin heavy chain locus, resulting in an aberrantly increased bcl-2 expression in B cells. Subsequently, Henderson et al. (Cell, 65: 1107–1115, 1991) demonstrated that expression of latent membranes protein 1 in cells infected by Epstein-Barr virus protected the infected B cells from programmed cell death by inducing expression of the bcl-2 gene. Sentman et al. (Cell, 67: 879–88, Nov. 29, 1991) demonstrated that expression of the bcl-2 gene can inhibit multiple forms of apoptosis but not negative selection in thymocytes, and Strasser et al. (Cell, 67: 889–899, Nov. 29, 1991) demonstrated that expression of a bcl-2 transgene inhibits T cell death and can perturb thymic self-censorship. Clem et al. (Science, 245: 1388–1390, Nov. 29, 1991) identified a specific baculovirus gene product as being responsible for blocking apoptosis in insect cells.

b. Herpes Virus Infections and Neurovirulence

The family of herpes virus includes animal viruses of great clinical interest because they are the causative agents of many diseases. Epstein-Barr virus has been implicated in B cell lymphoma; cytomegalovirus presents the greatest infectious threat to AIDS patients; and. Varicella Zoster Virus, is of great concern in certain parts of the world where chicken pox and shingles are serious health problems. A worldwide increase in the incidence of sexually transmitted herpes simplex (HSV) infection has occurred in the past decade, accompanied by an increase in neonatal herpes. Contact with active ulcerative lesions or asymptomatically excreting patients can result in transmission of the infectious agent. Transmission is by exposure to virus at mucosal surfaces and abraded skin, which permit the entry of virus and the initiation of viral replication in cells of the epidermis and dermis. In addition to clinically apparent lesions, latent infections may persist, in particular in sensory nerve cells. Various stimuli may cause reactivation of the HSV infection. Consequently, this is a difficult infection to eradicate. This scourge has largely gone unchecked due to the inadequacies of treatment modalities.

The known herpes viruses appear to share four significant biological properties:

1. All herpes viruses specify a large array of enzymes involved in nucleic acid metabolism (e.g., thymidine kinase, thymidylate synthetase, dUTPase, ribonucleotide reductase, etc.), DNA synthesis (e.g., DNA polymerase helicase, primase), and, possibly, processing of proteins (e.g., protein kinase), although the exact array of enzymes may vary somewhat from one herpesvirus to another.

2. Both the synthesis of viral DNAs and the assembly of capsids occur in the nucleus. In the case of some herpes viruses, it has been claimed that the virus may be de-enveloped and re-enveloped as it transits through the cytoplasm. Irrespective of the merits of these conclusions, envelopment of the capsids as it transits through the nuclear membrane is obligatory.

3. Production of infectious progeny virus is invariably accompanied by the irreversible destruction of the infected cell.

4. All herpes viruses examined to date are able to remain latent in their natural hosts. In cells harboring latent virus, viral genomes take the form of closed circular molecules, and only a small subset of viral genes is expressed.

Herpes viruses also vary greatly in their biologic properties. Some have a wide host-cell range, multiply efficiently, and rapidly destroy the cells that they infect (e.g., HSV-1, HSV-2, etc.). Others.(e.g., EBV, HRV6) have a narrow host-cell range. The multiplication of some herpes viruses (e.g., HCNV) appears to be slow. While all herpes viruses remain latent in a specific set of cells, the exact cell in which they remain latent varies from one virus to another. For example, whereas latent HSV is recovered from sensory neurons, latent EBV is recovered from B lymphocytes. Herpes viruses differ with respect to the clinical manifestations of diseases they cause.

Herpes simplex viruses 1 and 2 (HSV-1, HSV-2), are among the most common infectious agents encountered by humans (Corey and Spear, *N. Eng. J. Med.*, 31: 686–691, 1986). These viruses cause a broad spectrum of diseases which range from mild and nuisance infections such as recurrent herpes simplex labialis, to severe and life-threatening diseases such as herpes simplex encephalitis (HSE) of older children and adults, or the disseminated infections of neonates. Clinical outcome of herpes infections is dependent upon early diagnosis and prompt initiation of antiviral therapy. However, despite some successful therapy, dermal and epidermal lesions recur, and HSV infections of neonates and infections of the brain are associated with high morbidity and mortality. Earlier diagnosis than is currently possible would improve therapeutic success. In addition, improved treatments are desperately needed.

Extrinsic assistance has been provided to infected individuals, in particular, in the form of chemicals. For example, chemical inhibition of herpes viral replication has been effected by a variety of nucleoside analogues such as acyclovir, 5-flurodeoxyuridine (FUDR), 5-iododeoxyuridine, thymine arabinoside, and the like.

Some protection has been provided in experimental animal models by polyspecific or monospecific anti-HSV antibodies, HSV-primed lymphocytes, and cloned T cells to specific viral antigens (Corey and Spear, *N. Eng. J. Med.,* 314: 686–691, 1986). However, no satisfactory treatment has been found.

The $\gamma_1 34.5$ gene of herpes simplex virus maps in the inverted repeat region of the genome flanking the L component of the virus. The discovery and characterization of the gene was reported in several articles (Chou and Roizman, *J. Virol.,* 5: 629–635, 1986, and *J. Virol.,* 64: 1014–1020, 1990; Ackermann et al., *J. Virol.,* 58: 843–850, 1986). The key features are: (i) the gene encodes a protein of 263 amino acid in length; (ii) the protein contains Ala-Thr-Pro triler repeat ten times in the middle of the coding sequence; (iii) the protein is basic in nature and consists of large number of Arg and Pro amino acids; (iv) the promoter of the gene maps in the a sequence of the genome which also serves several essential viral functions for the virus; (v) the cis-acting element essential for the expression of the gene $\gamma_1 34.5$ is contained within the a sequence, in particular, the DR2 (12 base pair sequence repeated 22 times) and $U_b$ element. This type of promoter structure is unique to this gene and not shared by other viral gene promoters.

The function of the gene $\gamma_1 34.5$ in its ability to enable the virus to replicate, multiply and spread in the central nervous system (CNS) was demonstrated by a set of recombinant viruses and by testing their abilities to cause fatal encephalitis in the mouse brain. The mutant viruses lacking the gene therefore lost their ability to multiply and spread in the CNS and eyes and therefore is non-pathogenic. See Chou et al., *Science,* 250: 1212–1266, 1990.

The $\gamma_1 34.5$ gene functions by protecting the nerve cells from total protein synthesis shutoff in a manner characteristic of programmed cell death (apoptosis) in neuronal cells. The promoter appears to contain stress response elements and is transactivated by exposure to W irradiation, viral infection, and growth factor deprivation. These data suggest that the gene $\gamma_1 34.5$ is transactivated in the nerve cells at times of stress to prevent apoptosis.

The significance of these findings therefore lies in the fact that $\gamma_1 34.5$ extends viability or lends protection to the nerve cells so that in this instance, the virus can replicate and spread from cell to cell—defined as neurovirulence. It also appears that the protection can be extended to other toxic agents or environmental stresses to which the cell is subjected. An important aspect about the nature of the neurons, unlike any other cells in human, is the fact that neurons in the brain, eyes or CNS do not regenerate which forms the basis of many impaired neurological diseases. Any genes or drugs that extend the life of cells from death or degeneration can be expected to have a significant impact in the area of neural degeneration.

The role of $\gamma_1 34.5$, and anti-apoptosis factors, in infected cells is in its early stages of elucidation. Recent studies have suggested that Epstein-Barr virus enhances the survival capacity of infected cells through latent membrane protein 1(LMP1)-induced up-regulation of bcl-2. In that system it is postulated that LMP 1 induced bcl-2 up regulation gives virus infected B cells the potential to by-pass physiological selection and gain direct access to long lived memory B cell pools. However, bcl-2 expression fails to suppress apoptosis in some situations, for example upon withdrawal of interleukin-2 or interleukin-6. Moreover, the intracellular mechanism of action of bcl-2 expression remains unknown.

c. Programmed Cell Death and Disease Therapy

In light of the foregoing, it is apparent that the expression of $\gamma_1 34.5$ in CNS cells added an extra dimension of protection to the neurons against viral infection, and naturally ocurring and stress-induced apoptosis. An appreciation of this extra dimension of protection can be utilized in novel and innovative means for control and treatment of central nervous system (CNS) disorders. Specifically, treatment of CNS degenerative diseases, including Alzheimer's disease, Parkinson's disease, Lou Gerig's disease, and others the etiology of which may be traceable to a form of apoptosis, and the treatment of which is currently very poor, could be improved significantly through the use of either the 134.5 gene in gene therapy or the protein expressed by 134.5 as a therapeutic agent. This is especially critical where the death of neuronal cells is involved, due to the fact that, as noted, such cells do not reproduce post-mitotically. Since a finite number of neurons are available it is crucial to have available methods and agents for their protection and maintenance. $\gamma_1 34.5$ is also a very useful gene for assays of substances which mimic the effect of $\gamma_1 34.5$ and block stress of biologically induced programmed cell death.

Furthermore, the HSV-1 virus, appropriately modified so as to be made non-pathogenic, can serve as a vehicle for delivery of gene therapy to neurons. The HSV-L virus is present in neurons of the sensory ganglia of 90% of the world's human population. The virus ascends into neuronal cell bodies via retrograde axonal transport, reaching the axon from the site of infection by the process of neurotropism. Once in the neuronal cell body the virus remains dormant until some form of stress induces viral replication (e.g. UV exposure, infection by a second virus, surgery or axotomy). As noted, the use of HSV-1 as a vector would necessitate construction of deletion mutants to serve as safe, non-pathogenic vectors. Such a virus would act as an excellent vector for neuronal gene therapy and its use would be an especially important development since few methods of gene therapy provide a means for delivery of a gene across the central nervous system's blood-brain barrier.

Moreover, other viruses, such as HSV-2, picornavirus, coronavirus, eunyavirus, togavirus, rahbdovirus, retrovirus or vaccinia virus, are available as vectors for $\gamma_1 34.5$ gene therapy. As discussed with regard to the use of HSV-1 viruses, these vectors would also be altered in such a way as to render them non-pathogenic. In addition to the use of an appropriately mutated virus, implantation of transfected multipotent neural cell lines may also provide a means for delivery of the $\gamma_1 34.5$ gene to the CNS which avoids the blood brain barrier.

In addition, use of the HSV-1 virus with a specific mutation in the $\gamma_1 34.5$ gene provides a method of therapeutic treatment of tumorogenic diseases both in the CNS and in all other parts of the body. The "$\gamma_1 34.5$ minus" virus can induce apoptosis and thereby cause the death of the host cell, but this virus cannot replicate and spread. Therefore, given the ability to target tumors within the CNS, the $\gamma_1 34.5$ minus virus has proven a powerful therapeutic agent for hitherto virtually untreatable forms of CNS cancer. Furthermore, use of substances, other than a virus, which inhibit or block expression of genes with anti-apoptotic effects in target tumor cells can also serve as a significant development in tumor therapy and in the treatment of herpes virus infection, as well as treatment of infection by other viruses whose neurovirulence is dependent upon an interference with the host cells' programmed cell death mechanisms.

SUMMARY OF THE INVENTION

This invention relates to methods for the prevention or treatment of programmed cell death, or apoptosis, in neuronal cells for therapy in connection with neurodegenerative diseases, as well as methods of treatment of cancer and other tumorogenic diseases and herpes virus infection. The present invention also relates to assay methodologies allowing for the identification of substances capable of modulating the effects of the $\gamma_1 34.5$ gene or its protein expression product ICP34.5, i.e., substances capable of potentiating or inhibiting their effects. Additionally, the present invention also relates to assay methodologies designed to identify candidate substances able to mimic either $\gamma_1 34.5$ expression or the activity of ICP34.5. The present invention also relates to methods of delivering genes to cells for gene therapy.

In one illustrative embodiment of the present invention a method of preventing or treating programmed cell death in neuronal cells is described in which a non-pathogenic vector is prepared which contains the $\gamma_1 34.5$ gene. This vector is then introduced into neuronal cells which are presently undergoing or are likely to undergo programmed cell death. Those skilled in the art will realize that several vectors are suitable for use in this method, although the present invention envisions the use of certain unique and novel vectors designed specifically for use in connection with delivery of the $\gamma_1 34.5$ gene.

One such vector envisioned by the present invention is the HSV-1 virus itself, modified so as to render it non-pathogenic. Because of the unique capability of the HSV-1 virus to use an axon's internal transport system to move from the peripheral nerve endings of the neuron into the neuronal cell body, the present invention proposes the use of the non-pathogenic HSV-1 virus injected into the vicinity of the synaptic terminals of affected neurons, or in the area of a peripheral wound or lesion or other appropriate peripheral locus. The HSV-1 virus containing the $\gamma_1 34.5$ gene, under a different target-specific promoter, would then be transported into the neuronal cell body via retrograde axonal transport.

The present invention envisions specific genomic modifications being introduced into the HSV-1 virus in order to render the virus non-cytotoxic. These modifications could include deletions from the genome, rearrangements of specific genomic sequences, or other specific mutations. One example of such a modification comprises modification or deletion of the α4 gene which encodes the ICP4 protein. Deletion or modification of the gene expressing ICP4 renders the HSV-1 virus unable to express genes required for viral DNA and structural protein synthesis. However, the $\gamma_1 34.5$.gene placed under a suitable promoter would be expressed, thus inducing an anti-apoptotic effect in the neuron without the potential for stress induced neurovirulence. Other genes which might be modified include the the γ0 gene. The present invention also envisions the use of other vectors including, for example, retrovirus, picorna virus, vaccinia virus, HSV-2, coronavirus, eunyavirus, togavirus or rhabdovirus vectors. Again, use of of such viruses as vectors will necessitate construction of deletion mutations so that the vectors will be safe and non-pathogenic.

Another method by which the present invention envisions introducing the $\gamma_1 34.5$ gene into neuronal cells undergoing or likely to undergo programmed cell death, is through the use of multi-potent neural cell lines. Such lines have been shown to change phenotype in vitro and have also been demonstrated to become integrated into the central nervous system of mice and to differentiate into neurons or glia in a manner appropriate to their site of engraftment. Snyder, et al., *Cell*, 68: 33–51, 1992. Transplant or engraftment of multi-potent neural cell lines into which the $\gamma_1 34.5$ gene has been introduced into an area of the central nervous system in which cells are undergoing or are likely to undergo programmed cells death is expected to lead to reversal and inhibition of programed cell death.

It is expected that the ability of $\gamma_1 34.5$ to inhibit apoptosis will be a boon not only in human medicine, but also in basic scientific research. In this regard the present invention also envisions the use of the $\gamma_1 34.5$ gene in the extension of the life of neuronal cells in cell culture. Introduction of a non-cytotoxic vector into cultured neuronal cells will have an anti-apoptotic effect and will thereby extend the life of cell cultures. This in turn will extend the time periods over which experimentation may be conducted, and can also be expected to decrease the cost of conducting basic research.

In addition to utilizing a vector comprising the $\gamma_1 34.5$ gene, the present invention also discloses a method of preventing or treating programmed cell death in neuronal cells which involves the use of the product of expression of the $\gamma_1 34.5$ gene. The protein expressed by $\gamma_1 34.5$ is called ICP34.5. Ackermann, et al. (*J. Virol.*, 58: 843–850, 1986) reported that ICP34.5 has an apparent molecular weight of 43,500 upon SDS-polyacrylamide gel electrophoresis, appears to accumulate largely in the cytoplasm of HIV infected cells, and in contrast to many HSV-1 proteins, ICP34.5 has been demonstrated to be soluble in physiologic solutions.

In practicing this method or the method in which the $\gamma_1 34.5$ gene is introduced into cells, it is envisioned that the $\gamma_1 34.5$ gene or a biological functional equivalent thereof could be used for gene therapy, or ICP34.5 in a purified form or a biological functional equivalent of the ICP34.5 protein could be utilized as an anti-apoptotic agent. As used herein, functional equivalents are intended to refer to those proteins, and their encoding nucleic acid sequences, in which certain structural changes have been made but which nonetheless are, or encode, proteins evidencing an effect similar to that of ICP34.5.

In light of the fact that certain amino acids may be substituted for other amino acids in a protein without appreciable loss of defined functional activity, it is contemplated by the inventors that various changes may be made in the sequence of the ICP34.5 protein (or the underlying DNA of the $\gamma_1 34.5$ gene) without an appreciable loss of biological utility or activity. Amino acids with similar hydropathic scores may be substituted for one another (see Kyte et al., *J. Mol. Biol.*, 157: 105–132, 1982, incorporated herein by reference), as may amino acids with similar hydrophilicity values, as described in U.S. Pat. No. 4,554,101, incorporated herein by reference.

Therefore, amino acid substitutions are generally based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

This embodiment of the present invention describes a method which involves combining ICP34.5 or a biological functional equivalent thereof with a pharmaceutically acceptable carrier in order to form a pharmaceutical composition. (It should be understood in subsequent discussions that when $\gamma_1 34.5$ or ICP34.5 are referred to, the inventors intend to include biological functional equivalents, including any chemicals which mimic the effect of $\gamma_1 34.5$.) Such a composition would then be administered to neurons likely to undergo or undergoing programmed cell death. Such a composition could be administered to an animal using intravenous, intraspinal injection or, in certain circumstances, oral, intracerebral or intraventricular administration may be appropriate. Furthermore, neuronal cells in culture could also benefit from administration of ICP34.5 through administration directly into the medium in which the neuronal cells are grown.

ICP34.5 can be prepared using a nucleic acid segment which is capable of encoding ICP34.5 (i.e., the $\gamma_1 34.5$ gene or a biological functional equivalent). Such a segment could be expressed using, for example, a technique involving transferring the $\gamma_1 34.5$ segment into a host cell, culturing the host cell under conditions suitable for expression of the segment, allowing expression to occur, and thereafter isolating and purifying the protein using well established protein purification techniques. The nucleic acid segment would be transferred into host cells by transfection or by transformation of a recombinant vector into the host cell.

A particularly important embodiment of the present invention relates to assays for candidate substances which can either mimic the effects of the $\gamma_1 34.5$ gene, or mimic the effects of ICP34.5, as well as assays for candidate substances able to potentiate the function of $\gamma_1 34.5$ or potentiate the protective function of ICP34.5. Additionally, methods for assaying for candidate substances able to inhibit either $\gamma_1 34.5$ expression or the activity of ICP34.5 are also embodiments of the present invention.

In an exemplary embodiment, an assay testing for candidate substances which would block the expression of the anti-apoptosis gene or inhibit the activity of an anti-apoptotic protein such as ICP34.5 would proceed along the following lines. A test plasmid construct bearing the a sequence promoter and portions of the coding sequence of $\gamma_1 34.5$ is fused to the lacZ reporter gene, or any other readily assayable reporter gene. This construct is then introduced into an appropriate cell line, for example a neuroblastoma or PC12 cell line, by G418 selection. A clonal and continuous cell line for screening purposes is then established. A control plasma construct bearing an HSV late promoter (a promoter, which would normally not be expressed in cell lines and not induced to express by a stress factor which would normally induce apoptosis) is fused to the same or different indicator gene. This construct is also introduced into a continuous clonal cell line and serves as a control for the test cell line. The anti-apoptosis drugs would then be applied. Environmental stresses which typically trigger a sequence promoter activation and cause programmed cell death, such as UV injury, viral infection or deprivation of nerve growth factor, would then be applied to the cells. In control cells, the stress should have no effect on the cells and produce no detectible reaction in the assay. Stress in a test cell line in the absence of a positive candidate substance would give rise to an appropriate reaction, typically a colorimetric reaction. Introduction of stress to the test cell line in the presence of the candidate substance would give rise to an opposite colorimetric reaction indicating that the candidate substance interferes either with expression of the $\gamma_1 34.5$ gene, or with the ability of the substance to interfere with the anti-apoptotic activity of ICP34.5.

Similarly, the present invention describes an assay for candidate substances which would mimic or potentiate the activity of ICP34.5, or which would mimic the expression of $\gamma_1 34.5$, and such an assay would proceed along lines similar to those described above. A test cell line (e.g., a neuroblastoma cell line) constitutively expressing ICP34.5 and a fluorescent tagged cellular gene or any other tag providing an easily detected marker signalling viability of the cells is produced. In addition, a corresponding null cell line consisting of an appropriate indicator gene, for example the a-lacZ indicator gene, and the same host indicator gene as in the test cell line is also produced. Also, a third cell line (e.g., a vero cell line) consisting of the same indicator gene and the identical host indicator gene is also produced. Again, environmental stresses which trigger programmed cell death in the absence of $\gamma_1 34.5$ are applied to the cells. Candidate substances are also applied in order to determine whether they are able to mimic or. potentiate the anti-apoptotic effects of $\gamma_1 34.5$ expression or the anti-apoptotic activity of ICP34.5 or biological functional equivalents thereof.

The present invention also embodies a method of delivering genes for gene therapy. In an exemplary embodiment, the method involves combining the gene used for gene therapy with a mutated virus such as those described above, or with the HSV-1 virus rendered non-pathogenic. The gene and the virus are then combined with a pharmacologically acceptable carrier in order to form a pharmaceutical composition. This pharmaceutical composition is then administered in such a way that the mutated virus containing the gene for therapy, or the HSV-1 wild type virus containing the gene, can be incorporated into cells at an appropriate area. For example, when using the HSV-1 virus, the composition could be administered in an area where synaptic terminals are located so that the virus can be taken up into the terminals and transported in a retrograde manner up the axon into the axonal cell bodies via retrograde axonal transport. Clearly, such a method would only be appropriate when cells in the peripheral or central nervous system were the target of the gene therapy.

The present invention also envisions methods and compositions for the treatment of cancer and other tumorogenic diseases, as well as herpes infections or other infections involving viruses whose virulence is dependent upon an anti-apoptotic effect. Candidate substances identified as having an inhibiting effect upon either the expression or activity of ICP34.5 identified in the assay methods discussed above could be used to induce cell death in target tumor cells, or in virus-infected cells. Pharmaceutical compositions containing such substances can be introduced using intrathecal, intravenous, or direct injection into the tumor or the infected area, as appropriate.

BRIEF DESCRIPTION OF THE DRAWINGS

FIG. 9a: Photograph of ethidium bromide stained agarose gel containing electrophoretically separated BamHI digests of total DNAs extracted, from mock-infected cells or cells infected with HSV-1(F), R36i6, R4009 or HSV-1(F)R viruses. FIG. 9b: Hybridization of electrophoretically separated RNA transferred to a nitrocellulose sheets probed with RNA sequences antisense to α47, $U_S10$ and $U_S11$ open reading frames. SK-N-SH neuroblastoma and Vero cells were either mock-infected or exposed to 5 pfu of HSV-1(F) or of R3616 per cell. Total DNAs were extracted from cells at 17 hr post infection by the procedure published by Katz et al., (J. Virol., 64: 4288–4295), digested with BamHI, electrophoresed in 0.8% agarose gel at 40V overnight and stained with ethidium bromide for visualization. For RNA analysis, SK-N-SH neuroblastoma and Vero cells were either mock-infected or infected with R3616 and HSV-1(F) as described above. At 13 hrs post exposure of cells to virus the RNA was extracted by the procedure of Peppel and Baglioni (BioTechniques, 9: 711–712, 1990). The RNAs were then separated by electrophoresis on 1.2% agarose gel, transferred by gravity to a nitrocellulose sheet and probed with anti-sense RNA made from in vitro transcription of pRB3910 off T7 promoter using kit from Promega, Inc. according to manufacturer's instruction. α47, $U_S10$ and $U_S11$ transcripts overlap in sequence and share the same 3' co-terminal sequence. McGeoch et al., J. Gen. Virol., 64: 1531–1574 (1988). The $U_S10$ transcript is of low abundance and not detected in this assay.

DETAILED DESCRIPTION OP THE PREFERRED EMBODIMENTS

Introduction

Figure 1:
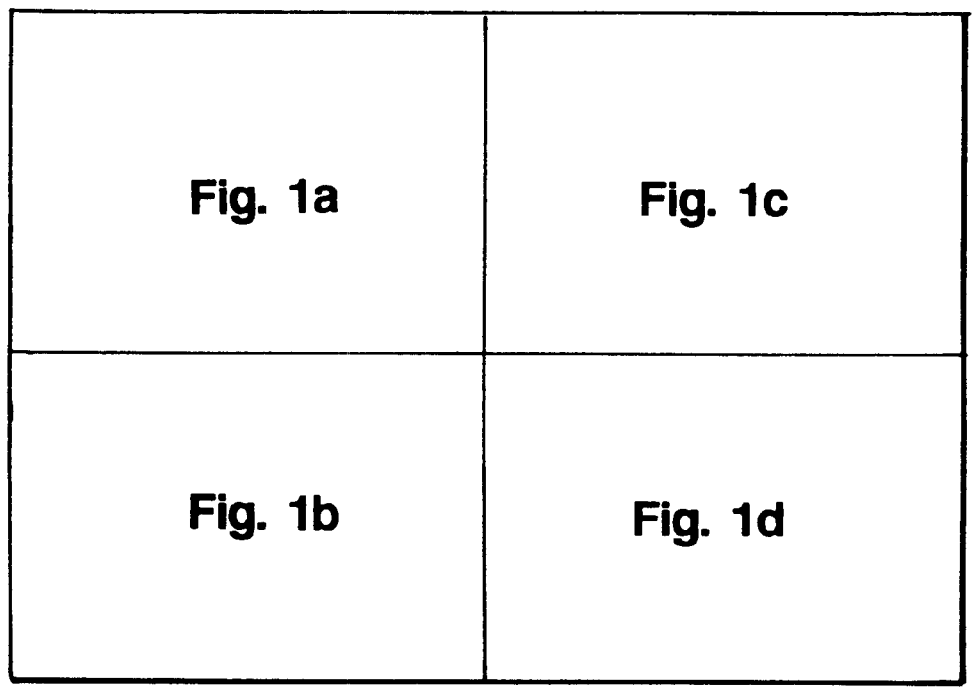
FIGS. 1a–1d show DNA sequence comparisons of HSV-1 strains F (SEQ ID NOS. 1–5) collectively SEQ ID NO. 36 17syn+(SEQ ID NOS. 6–9) collectively SEQ ID NO. 37, MGH-10 (SEQ ID NOS. 10–15) collectively SEQ ID NO. 38, and CVG-2 (SEQ ID NOS. 16–20) collectively SEQ ID NO 39 in the region of the gene for ICP34.5 (FIGS. 1a–1b) and the predicted open frames for ICP34.5 in these strains (SEQ ID NOS. 25–34 with the complete amino acid sequences being set out in SEQ ID NOS. 40, 41, 42, and 43, respectively (FIGS. 1c–1d). Unless otherwise indicated by a new base (insertion of A, C, G, or T), a new amino acid (three-letter code), or absence of a base or amino acid (-), the sequences for strains HSV-1(17)syn+, HSV-1(MGH-10), and HSV-1(CVG-2) were identical to the sequence for HSV-1(F). An asterisk indicates initiation of a repeat sequence of nine nucleotides or three amino acids. Direct repeat 1(DR1) designates the 20-base-pair repeat sequence flanking the a sequence. Sequences upstream of direct repeat 1 are contained within the a sequence. The number at the end of each line indicates the relative position from nucleotide 1 (FIGS. 1a–1b) or amino acid 1 (FIGS. 1c–1d). The initiation and termination codons for the HSV-1(F) sequence are underlined.
Figure 2:
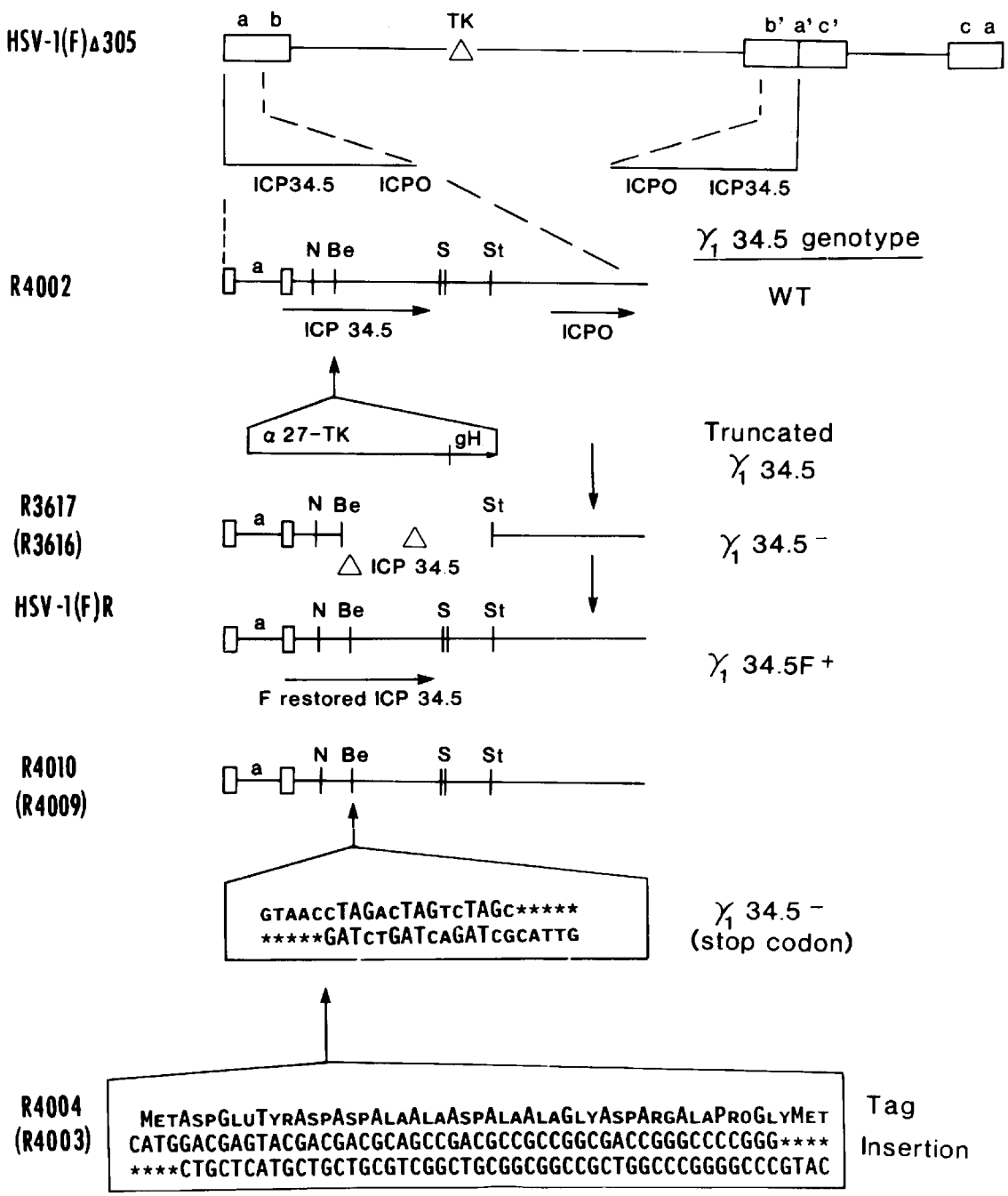
FIG. 2 shows sequence arrangements of the genome of wild-type strain HSV-1 strain F [HSV-1(F)] and of recombinant viruses derived from it. Top line, the sequence arrangement of HSV-1(F) Δ305. The rectangles identify the inverted repeats ab, b' a' c, and ca. The HSV-(F) a sequence is present in a direct orientation at the two genomic termini and in the inverted orientation at the junction between the long and short components. The b and c sequences are approximately 9 and 6 kbp long, respectively. The triangle marked TK identifies the position of the tk gene and of the Bgl II to Sac I sequence of BamHI Q fragment deleted from HSV-1(F)Δ305. Lines two and three from the top show that the b sequences contain the genes specifying ICP34.5 and ICP0 and, since b sequence is repeated in an inverted orientation, there are two copies of these genes per genome. The construction of the a24-tk fragment containing portions of the glycoprotein H gene has been described. Chou and Roizman,*J. Virol.,* 57: (1986); Ackerman et al.,*J. Virol.,* 58: 843 (1986); Chou and Roizzan, *J. Virol.,* 64: 1014 (1990). Line 7 shows a schematic diagram of the insertion of the oligonucleotide containing stop codons in all three reading frames. The plasmids pRB3615 and pRB2976 used in the construction of R4002 and R4004, respectively, were described elsewhere. Chou and Roizran, *J. Virol.,* 57: 629 (1986) and J. Virol., 64: 1014 (1990). To generate pRB3616, plasmid pRB143 was digested with BstEII and Stu I, bluntended with T4 polymerase, and relegated. The asterisks designate nucleotides from vector plasmid that form cohesive ends with the synthesized oligomers (SEQ ID NOS. 21 and 22). The insertion of the α4 epitope (SEQ ID NO.35) into the first amino acid of ICP34.5 (line 9) has been described, Chou and Roizman, *J. Virol.,* 64: 1014.(1990), except that in this instance the sequence was inserted into both copies of the $\gamma_1 34.5$ gene. The tk gene was restored in all recombinant viruses tested in mice. HSV-1(F)R (line 6) was derived from R3617 by restoration of the sequences deleted in $\gamma_1 34.5$ and tk genes. N, Be, S, and St are abbreviations for Nco I, BstEII, Sac I, and Stu I restriction endonucleases (New England Biolabs), respectively. The numbers in parentheses are the tk$^+$ version of each construct tested in mice.
Figure 3A:
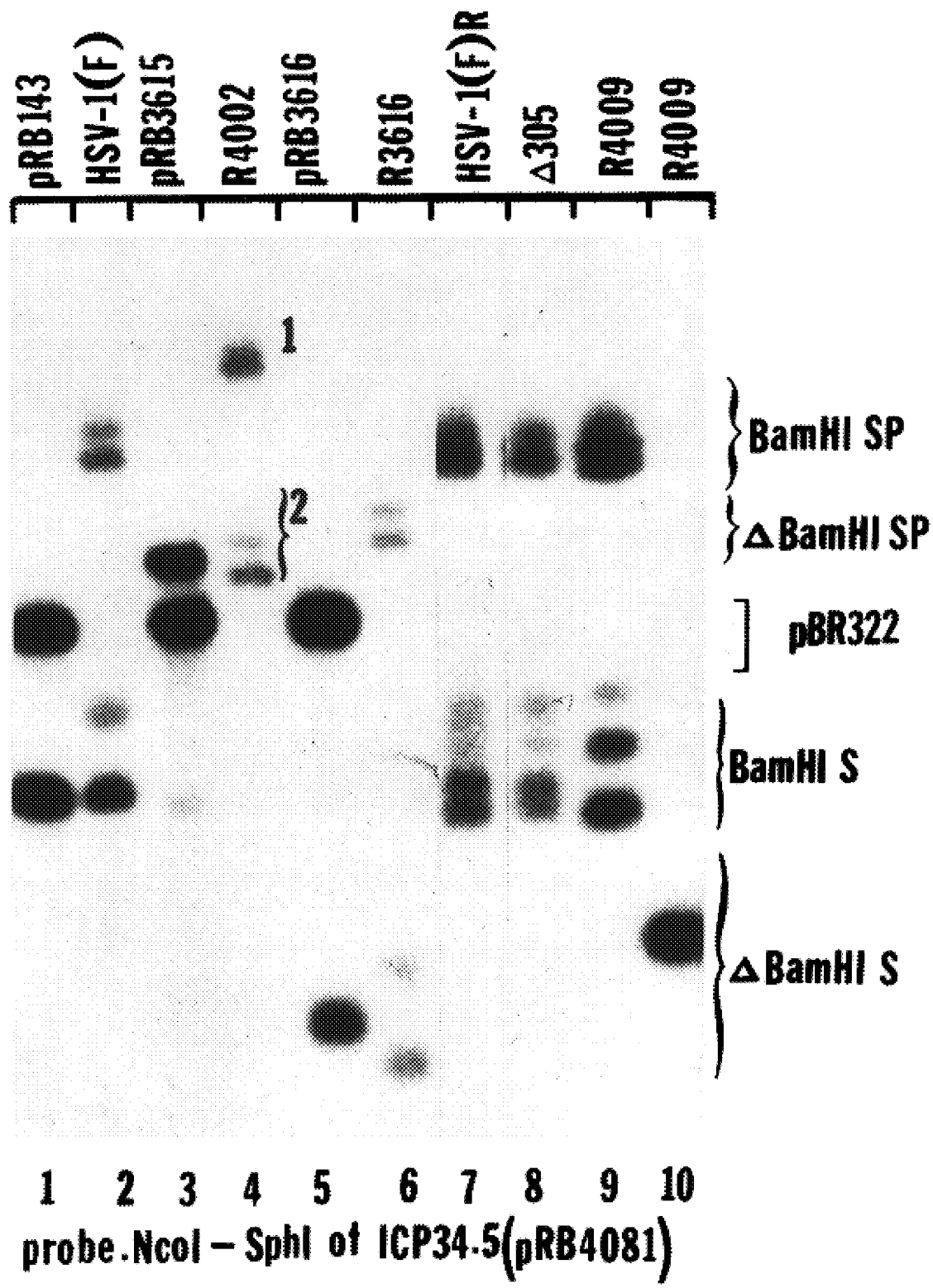
FIGS. 3a and 3b show an autoradiographic image of electrophoretically separated digest of plasaid, wild-type, and mutant virus DNAs, transferred to a solid substrate and hybridized with labelled probes for the presence of $\gamma_1 34.5$ and tk genes. The plasmids or viral DNAs shown were digested with BamHI or, in the case of R4009 shown in lanes 10, with both BamHI and Spe I. The hybridization probes were the fragment Nco I to Sph I contained entirely within the coding sequences of $\gamma_1 34.5$ (FIG. 3a) and the BamHI Q fragment of HSV-1(F) (FIG. 3b). The probes were labeled by nick translation of the entire plasmid DNAs with [$\alpha$-$^{32}$P] deoxycytidine triphosphate and reagents provided in a kit (Du Pont Biotechnology Systems). The DNAs that were limit digested with BamHI (all lanes) or both BamHI and Spe I (FIG. 3a, lane 10) were electrophoretically separated on 0.8% agarose gels in 90 mM trisphosphate buffer at 40 V overnight. The DNA was then transferred by gravity to two nitrocellulose sheets sandwiching the gel and hybridized overnight with the respective probes. $\gamma_1 34.5$ maps in BamHI S and SP fragments, which form a characteristic ladder of bands at 500-bp increments. The ladders are a consequence of a variable number of a sequences in the repeats flanking the unique sequences of the junction between the long and short components, whereas BamHI S is the terminal fragment of the viral genome at the terminus of the long component, whereas BamHI SP is a fragment formed by the fusion of the terminal BamHI S fragment with BamHI P, the terminal BamHI fragment of the short component. Bands of BamHI S, SP, and Q and their deleted versions, $\Delta$BamHI S, $\Delta$BamHI SP, and $\Delta$BamHI Q ($\Delta$Q), respectively, are indicated. Band 1 represents the 1.7-kbp $\alpha$27-tk insert into the BamHI SP fragment in R4002, and therefor this fragment reacted with both labeled probes (lanes 4). Band 2 represents the same insertion into the BamHI S fragment.
Figure 3B:
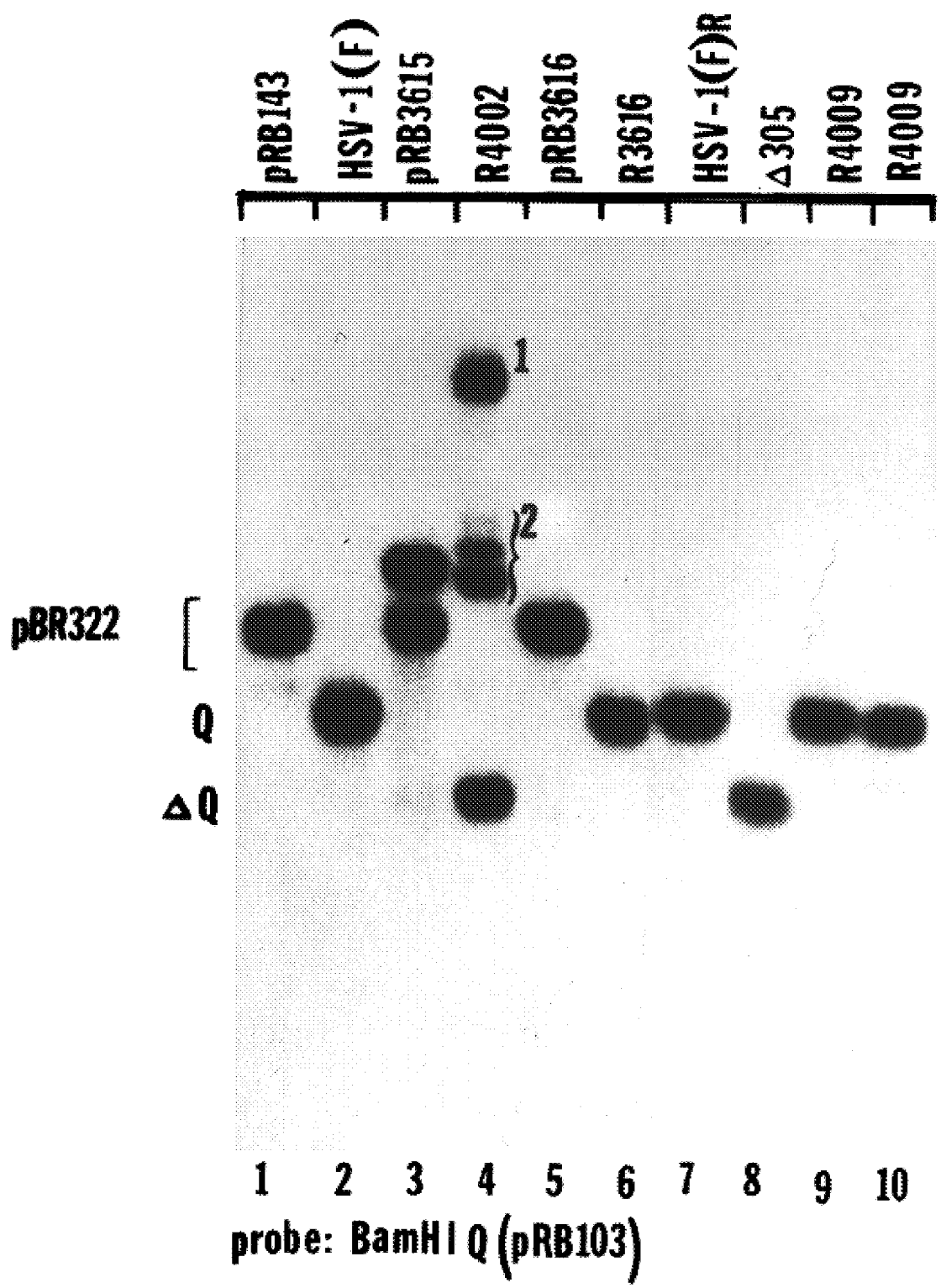

The present invention relates to the use of the HSV-1 $\gamma_1 34.5$ gene, the ICP34.5 protein expressed by that gene, and derivatives of the protein which function in a similar manner as therapeutics for (neuronal) programmed cell death. The present invention also relates to the use of altered, non-pathogenic HSV-1 virus (as well as other viruses) as a vector for gene therapy. Other aspects of the present invention relate to assays for detecting candidate substances capable of acting as anti-apoptotic agents, as well as assays for detecting candidate substances able to induce programmed cell death in tumor cells. Additionally, the present invention also relates to methods for treating cancer and other tumorgenic diseases. Finally, the present invention also relates to the use of candidate substances capable of inactivating the $\gamma_1 34.5$ gene or ICP34.5 and thereby suppressing HSV-1 and other viral infections.

The wild-type HSV-1 genome (150 kilobase pairs) has two components, L and S, each possessing unique sequences flanked by inverted repeats. The repeat sequences of the L component, designated ab and b'a', are each 9 kilobase pairs, whereas the repeat sequences of the S component, designated a'c' and ca, are each 6.5 kilobase pairs. Wadsworth et al., J. Virol., 15: 1487–1497 (1975). The shared a sequence, 500-base pairs long in HSV-1 strain F (HSV-1(F)], is present in one copy at the S component terminus and in one to several copies, in the same orientation, at the junction between L and S components. The L and S components invert relative to each other such that the DNA extracted from virions or infected cells consists of four isomers differing solely in the orientation of the L and S components relative to each other. Hayward et al., Proc. Natl. Acad. Sci. USA, 72: 4243–4247 (1975). The n sequence appears to be a cis-acting site for inversions inasmuch as insertion of the a sequence elsewhere in the genome or deletion of the entire internal inverted repeat sequences (b'a'c') leads to additional inversions or the loss of the ability of the L and S components to invert, respectively. The a sequence was also shown to contain the cis-acting sites for the circularization of the genome after infection, for cleavage of the HSV genome from concatemers, and for encapsidation of the DNA.

HSV-1 genomes contain at least 73 genes whose expression is coordinately regulated and sequentially ordered in cascade fashion. The α genes are expressed first, followed by β, $\gamma_1$ and $\gamma_2$ genes. The differentiation among β, $\gamma_1$ and $\gamma_2$ genes is operationally based on the effect of inhibitors of viral DNA synthesis. Whereas the expression of β genes is stimulated and that of $\gamma_1$ genes is only slightly reduced by inhibitors of viral DNA synthesis, the expression of $\gamma_2$ genes stringently requires viral DNA synthesis.

In the course of studies on the function of the a sequence, Chou and Roizman (Cell, 4: 803–811, 1985) noted that the chimeric structure consisting of the a sequence fused to the 5' transcribed, noncoding sequences of the thymidine kinase (TK) gene of HSV-1 was inducible in transferred cells and regulated as a $\gamma_1$ gene when inserted into the viral genome. This observation suggested that the terminus of the a sequence nearest the b sequence of the inverted repeats contained a promoter and the transcription initiation site of a gene whose structural sequences were located in the b sequences flanking the L component. Studies involving hybridization of labeled DNA probes to electrophoretically separated RNAs extracted from infected cells, and S1 nuclease analyses confirmed the existence of RNA transcripts initiating in the a sequence. Nucleotide sequence analyses revealed the presence of an open reading frame capable of encoding a protein 263 amino acids long. Chou and Roizman, J. Virol., 64: 1014–1020 (1990).

Previous studies have shown that each inverted repeat of the S component contains in its entirety a gene designated α4, whereas each of those of the L component contains in its entirety a gene designated ah. See, e.g., Mackem and Roizman, J. Virol., 44: 934–947 (1982). The putative gene identified on the basis of nucleotide sequence and analyses of RNA is also present in two copies per genome. Because of the overlap of the domain of this gene with the a sequence containing the cis-acting sites for inversion, cleavage of DNA from concatemers, and packaging of the DNA, it was of interest to identify and characterize the gene product. For this purpose, the observation that the nucleotide sequence predicted the presence in the protein of the amino acid triplet Ala-Thr-Pro repeated 10 times was utilized, and antibody to a synthetic peptide synthesized on the basis of this sequence reacted with a 43,500-apparent-molecular-weight HSV-1 protein. Ackerman et al., J. Virol., 58: 843–850, 1986.

The extent of variability of the open reading frame that encodes ICP34.5 was established by comparing the nucleotide sequences of three HSV-1 strains passaged a limited number of times outside a human host. Chou and Roizman (J. Virol., 64: 1014–1020, 1990) reported that the gene that specifies ICP34.5 contains 263 codons conserved in all three limited passage strains but not in the reported sequence of the HSV-1(17)syn+strain. (FIGS. 1a–1d) To ensure that the antibody to a predicted repeat sequence, Ala-Thr-Pro, reacted with ICP34.5 rather than with a heterologous protein with a similar repeat sequence, a short sequence of 45 nucleotides that encodes an epitope characteristic of another HSV-1 gene was inserted near the 5' terminus of the ICP34.5-coding domain. The recombinant virus expressed a protein with an appropriately slower electrophoretic mobility and which reacted with both the monoclonal antibody to the inserted epitope and rabbit antiserum to the Ala-Thr-Pro repeat element.

Figure 4A:
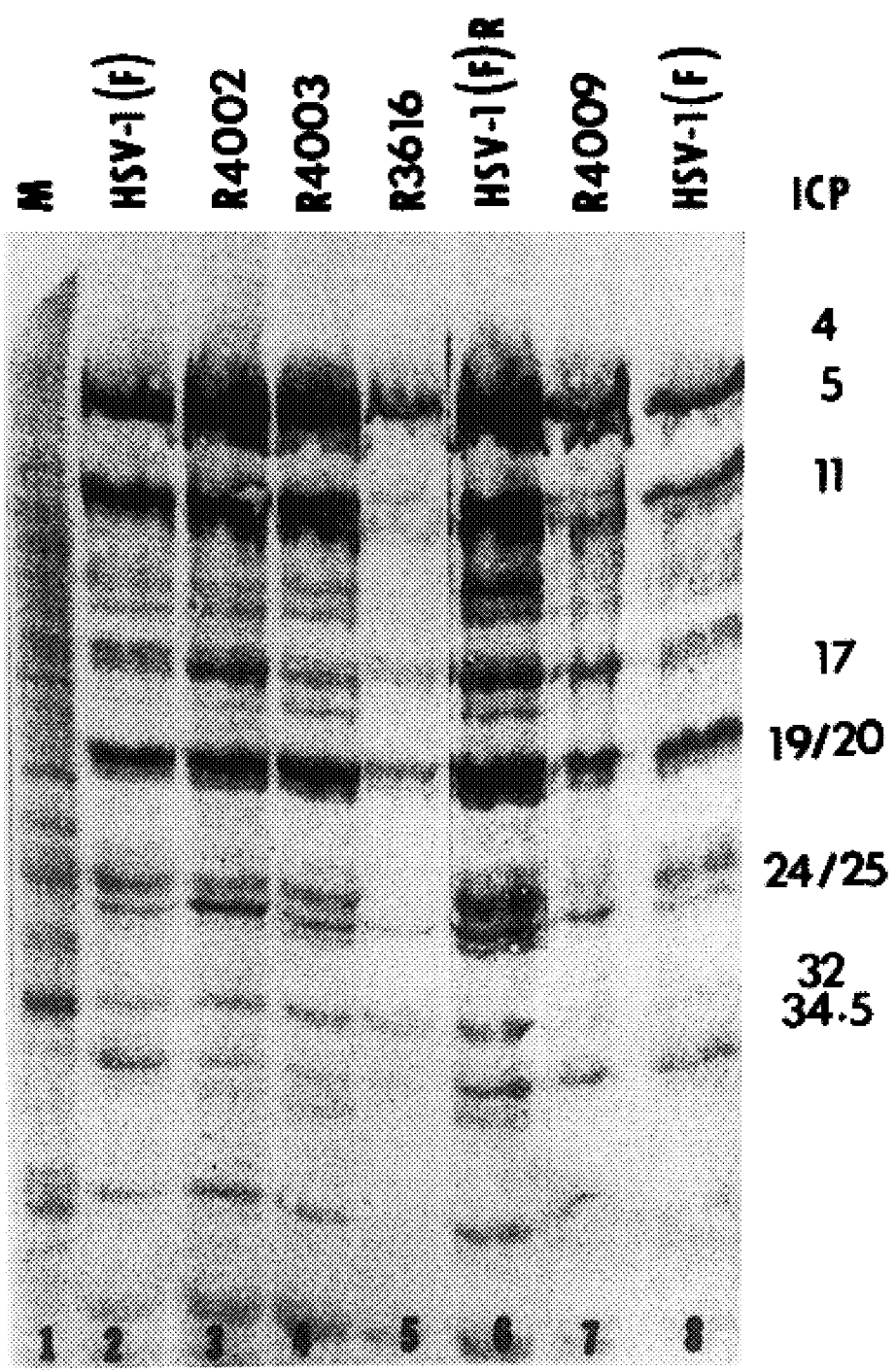
FIGS. 4a and 4b show autoradiographic images (FIG. 4a) and photograph of lysates of cells mock infected (M) or infected with HSV-1(F) and recombinant viruses (FIG. 4b) separated electrophoretically in denaturing polyacrylamide (10%) gels, transferred electrically to a nitrocellulose sheet, and stained with rabbit polyclonal antibody R4 described elsewhere. Ackerman et al., J. Virol., 58: 843 (1986); Chou and Roizman, J. Virol., 64: 1014 (1990). Replicate cultures of Vero cells were infected and labeled with [$^{35}$S]methionine (Du Pont Biotechnology Systems) from 12 to 24 hours after infection, and equivalent amounts of cell lysates were loaded in each slot. The procedures were as described (Ackerman et. al.; Chou and Roizman) except that the bound antibody was made apparent with the alkaline phosphatase substrate system supplied by Promega, Inc. Infected cell proteins were designated by number according to Honess and Roizman (J. Virol., 12: 1346 (1973)). The chimeric ICP34.5 specified by R4003 migrated more slowly than the protein produced by other viruses because of the increased molecular weight caused by the insertion of the epitope.
Figure 4B:
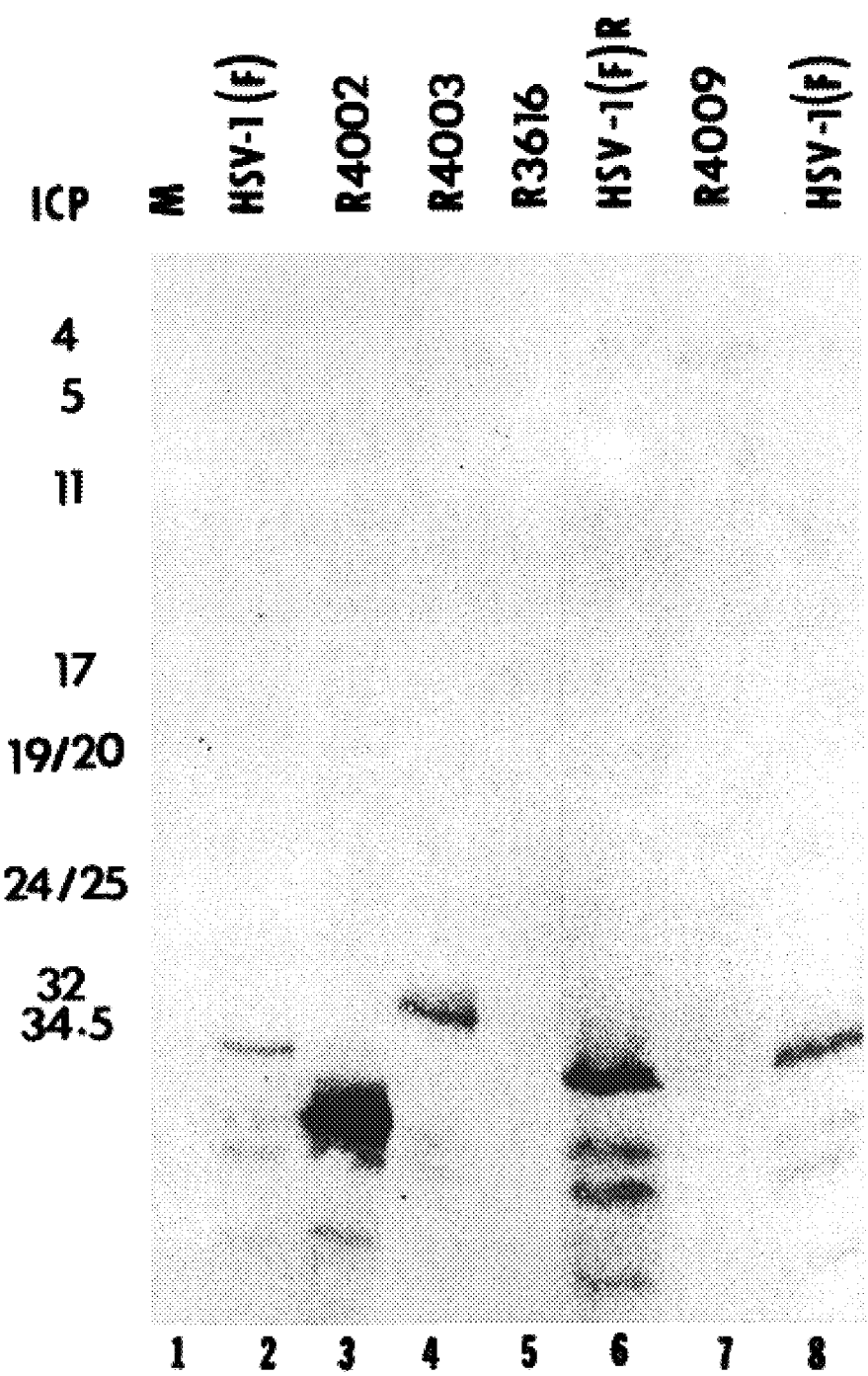

Studies of the identification of the genes associated with neurovirulence have repeatedly implicated DNA sequences located at or near a terminus of the long component of HSV-1 DNA. Thus, Centifanto-Fitzgerald et al. (*J. Exp. Med.,* 155: 475,1982) transferred, by means of a DNA fragment, a virulence marker from a virulent to an antivirulent strain of HSV-1. Deletion of genes located at one terminus of the long component of HSV-1 DNA contributed to the lack of virulence exhibited by a prototype HSV vaccine'strain. Meignier et al., *J. Infect. Dis.,* 158: 602 (1988). In other studies, Javier et al. (*J. Virol.,* 65: 1978, 1987) and Thompson et al. (*Virology,* 172: 435, 1989) demonstrated that an HSV-1×HSV-2 recombinant virus consisting largely of HSV-1 DNA but with HSV-2 sequences located at one terminus of the long component was avirulent; virulence could be restored by rescue with the homologous HSV-1 fragment. Taha et al. (*J. Gen. Virol.,* 10: 705, 1989) described a spontaneous deletion mutuant lacking 1.5 kbp at both ends of the long component of a HSV-2 strain. Because of heterogeneity in the parent virus population, the loss of virulence could not be unambiguously related to the specific deletion, although the recombinant obtained by marker rescue was more virulent than the deletion mutant. In neither study was a specific gene or gene product identified at the mutated locus, and no gene was specifically linked to virulence phenotype.

Role of the $\gamma_1$34.5 Gene

To test the possible role of the product of the $\gamma_1$34.5 gene, ICP34.5, a series of four viruses (FIG. 2) were genetically engineered by the procedures of Post and Roizman (*Cell* 25: 227, 1981, incorporated herein by reference).

1) Recombinant virus R4002 (FIG. 4*a*, lane 3 and FIG. 4*b*, lane 3) contained the insertion of a thymidine kinase (tk) gene driven by the promoter of the α27 gene (α27-tk) in both copies of the ICP34.5 coding sequences. It was constructed by cotransfecting rabbit skin cells with intact DNA of HSV-1(F)Δ305, a virus from which a portion of the tk gene was specifically deleted, with the DNA of plasmid pRB3615, which contains the α27-tk gene inserted into the $\gamma_1$34.5 gene contained in the BamHI S fragment. Recombinants that were $tk^+$ were then selected on human 143 thymidine kinase minus ($TX^-$) cells. The fragment containing the α27-tk gene contains downstream from the tk gene: the 5' untranscribed promoter, the transcribed noncoding sequence, and the initiating methionine codon of the glycoprotein H gene. The BstEII site into which the α27-tk fragment was inserted is immediately upstream of the codon 29 of the $\gamma_1$34.5 open reading frame. As a consequence, the initiating codon of glycoprotein H was fused in frame and became the initiating codon of the truncated open reading frame of the $\gamma_1$34.5 gene (FIG. 2, line 3). The recombinant selected for further study, R4002, was shown to contain the α27-tk gene insert in both copies of 7134.5 gene (FIG. 3*a*, lane 4 and FIG. 3*b*, lane 4) and specified only the predicted truncated product of the chimeric $\gamma_1$34.5 gene (FIG. 4*b*). The amounts of the native ICP34.5 protein detected in these and previous studies have been generally low. The chimeric genes formed by the fusion of the 5' transcribed noncoding region and the initiating codon of glycoprotein H in frame with the truncated $\gamma_1$34.5 gene were expressed far more efficiently than the native genes.

2) The recombinant virus R3617 (FIG. 2, line 5 from the top) lacking 1 kb of DNA in each copy of the $\gamma_1$34.5 gene was generated by cotransfecting rabbit skin cells with intact R4002 DNA and the DNA of plasmid pRB3616. In this plasmid, the sequences containing most of the coding domain of $\gamma_1$34.5 has been deleted (FIG. 2, line 5 from top). The $tk^-$ progeny of the transfection was plated on $143TK^-$ cells overlaid with medium containing bromodeoxy uridine (BrdU). This procedure selects $tk^-$ viruses, and since the tk gene is present in both copies of the $\gamma_1$34.5 gene, the selected progeny of the transfection could be expected to contain deletions in both copies. The selected $tk^-$ virus designated as R3617 was analyzed for the presence of the deletion in both copies of the $\gamma_1$34.5 gene. For assays of neurovirulence, the deletion in the native $tk^-$ gene of R3617, which traces its origin from HSV-1(F)Δ305, had to be repaired. This was done by cotransfection of rabbit skin cells with intact R3617 DNA and BamHI Q fragment containing the tk gene. The virus selected for $tk^+$ phenotype in $143TK^-$ cells was designated R3616. This virus contains a wild-type BamHI Q fragment (FIG. 3*b* lane 6) and does not make ICP34.5 (FIG. 4*b*).

3) To ascertain that the phenotype of R3616 indeed reflects the deletion in the $\gamma_1$34.5 gene, the deleted sequences were restored by cotransfecting rabbit skin cells with intact R3617 DNA, the HSV-1(F) BamHI Q DNA fragment containing the intact tk gene, and the BamHI SP DNA fragment containing the intact $\gamma_1$34.5 gene in the molar ratios of 1:1:10, respectively. Viruses that were $tk^+$ were then selected in $143TK^-$ cells overlaid with medium containing hypoxanthine, aminopterin, and thymidine. The $tk^+$ candidates were then screened for the presence of wild-type tk and $\gamma_1$34.5 genes. As expected, the selected virus designated HSV-1(F)R (FIG. 2, line 6) contained a wild-type terminal long component fragment (compare FIG. 3*a*, lanes 2, 7, and 8), and expressed ICP34.5 (FIG. 4*a*, lane 6).

4) To eliminate the possibility that the phenotype of R3616 reflects deletion in cryptic open reading frames, a virus was constructed (R4010, FIG. 2, line 7 from the top) that contains translational stop codons in all three reading frames in the beginning of the ICP34.5 coding sequence. The 20-base oligonucleotide containing the translational stop codons and its complement sequence (FIG. 2) were made in an Applied Biosystems 380D DNA synthesizer, mixed at equal molar ratio, heated to 80° C., and allowed to cool slowly to room temperature. The annealed DNA was inserted into the HSV-1(F) BamHI S fragment at the BstEII site. The resulting plasmid pRB4009 contained a stop codon inserted in the beginning of the ICP34.5 coding sequence. The 20 nucleotide oligomer DNA insertion also contained a Spe I restriction site, which allowed rapid verification of the presence of the insert. To generate the recombinant virus. R4010, rabbit skin cells were cotransfected with the intact DNA of R4002 and the pRB4009. plasmid DNA. Recombinants that were $tk^-$ were selected in $143TK^-$ cells in medium containing BrdU. The $tk^+$ version of this virus, designated R4009, was generated by cotransfection of intact $tk^-$ R4010 DNA with HSV-1(F) BamHI Q DNA fragment, and selection of $tk^+$ progeny. The virus selected for neurovirulence studies, R4009, contained the Spe I restriction endonuclease cleavage site in both BamHI S and SP fragments (compare FIG. 3*a*, lanes 9 and 10) and did not express ICP34.5 (FIG. 4*b*, lane 7).

5) R4004 (FIG. 2, last line) was a recombinant virus produced by insertion of a sequence encoding 16 amino acids. This sequence has been shown to be the epitope of the monoclonal antibody H943 reactive with a viral protein designated as ICP4. Hubenthal-Voss et al., *J. Virol.,* 62: 454 (1988). The virus was generated by cotransfecting intact R4002 DNA and the DNA of plasmid pRB3976 containing the insert, and the selected $tk^-$ progeny was analyzed for the presence of the insert. For neurovirulence studies, its tk gene was restored (recombinant virus R4003) as described above.

The DNA sequence was inserted in frame at the Nco I site at the initiating methionine codon of the $\gamma_1 34.5$ gene. The insert regenerated the initiating methionine codon and generated a methionine codon between the epitope and the remainder of ICP34.5. Because of the additional amino acids, the protein migrated more slowly in denaturing polyacrylamide gels (FIG. 4b, lane 4).

Plaque morphology and size of all of the recombinants were similar to those of the wild-type parent, HSV-1(F) when plated on Vero, 143TK$^-$, and rabbit skin cells lines. Whereas HSV-1(F)R and R4003 replicated as well as the wild-type virus in replicate cultures of Vero cells, the yields of R3616 and R4009 were reduced to one-third to one-fourth the amount of the wild type. Although ICP34.5 was not essential for growth of HSV-1 in cells in culture, the results of the studies shown in Table 1 indicate that the deletion or termination of translation of the $\gamma_1 34.5$ has a profound effect on the virulence of the virus. Thus, all of the mice inoculated with the highest concentration [$1.2 \times 10^6$ plaque-forming units (PFU)] of R3616 survived. In the case of R4009, only three of ten mice died as a result of inoculation with the highest concentration of virus ($\sim 10^7$ PFU). In comparison with other deletion mutants, R3616 and R4009 rank among the least pathogenic viruses reported to date. The virus in which the $\gamma_1 34.5$ gene was restored exhibited the virulence of the parent virus.

TABLE 1

| Virus in the inoculum | Genotype | PFU/LD$_{50}$ |
| --- | --- | --- |
| HSV-1(F) | Wild-type parent virus | 420 |
| R3616 | 1000-bp deletion in the $\gamma_1 34.5$ | >1,200,000 |
| HSV-1(F)R | Restoration of $\gamma_1 34.5$ and tk | 130 |
| R4009 | Stop codon in $\gamma_1 34.5$ | >10,000,000 |
| R4003 | Monoclonal antibody epitope inserted at the NH$_2$ terminal | 4,200 |

Comparative ability of wild-type and recombinant viruses to cause death after intracerebral inoculation of mice. The neurovirulence studies were done on female BALB/C mice obtained at 21 days of age (weight±1.8 g) from Charles River Breeding Laboratories in Raleigh, N.C. The viruses were diluted in minimum essential medium containing Earle's salts and 10% fetal bovine serum,, penicillin, and gentamicin. The mice were inoculated intracerebrally in the right cerebral hemisphere with a 26-gauge needle. The volume delivered was 0.03 ml, and each dilution of virus was tested in groups of ten mice. The animals were checked daily for mortality for 21 days. The LD$_{50}$ was calculated with the aid of the "Dose effect Analysis" computer program from Elsevier Biosoft, Cambridge, United Kingdom.

The wild-type virus and all of the recombinants have identical surface glycoproteins necessary for attachment and penetration into brain cells. Injection of $10^6$ PFU into the brain should result in infection and death of a significant number of the brain cells. Death after intracerebral inoculation results from viral replication, spread from cell to cell, and cell destruction before the immune system has a chance to act. Titrations of brain tissue suspended in minimal essential medium containing Eagle's salts and 10% fetal bovine serum showed that the brains of animals inoculated with the viruses that failed to make ICP34.5 contained very little virus. Thus, for the R3616 and R4009 viruses, the recovery was 120 and 100 PFU per gram of brain tissue, respectively. Given the amount of virus in the inoculum (highest concentration tested), it is not clear whether the small amounts of recovered virus represent a surviving fraction of the inoculum or newly replicated virus. In contrast, the amounts of virus recovered from mice inoculated with HSV-1(F)R and R4003 were $6 \times 10^6$, respectively. These results indicate that the failure of the two recombinant viruses to cause death must be related to poor spread of virus in neuronal tissue as a consequence of the inability of mutant viruses to replicate in the CNS, reflecting a reduction in their host range.

In the course of studies designed to determine the function of the $\gamma_1 34.5$ gene product, it was discovered that infection of cells of neuronal origin with mutants incapable of expressing the $\gamma_1 34.5$ gene resulted in shutoff of cellular protein synthesis, whereas infection of cells of non neuronal origin with wild type or mutant viruses resulted in sustained protein synthesis and production of infectious progeny.

EXAMPLE 1

IMPACT OF $\gamma_1 34.5$ EXPRESSION ON PROGRAMMED CELL DEATH

Materials and Methods

Cells Vero cells originally obtained from ATCC were propagated in DME media containing 5% calf serum. The human SK-N-SH neuroblastoma (NB) cell line was obtained from ACTT (HTB11) and propagated in Dulbecco's modified Eagle's medium containing 10% fetal bovine serum.

Figure 5:
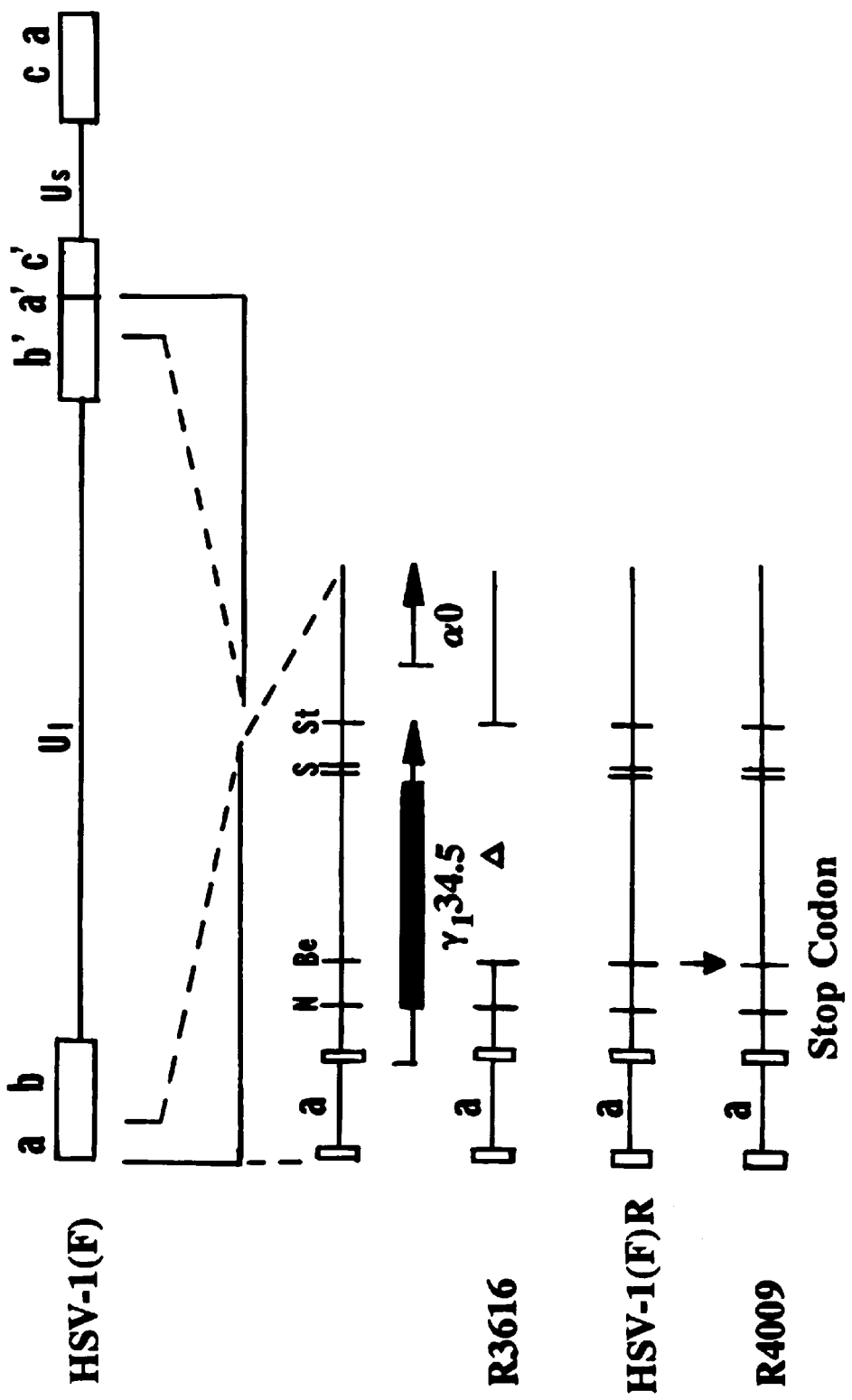
FIG. 5 is a schematic representation of the genome structure and sequence arrangements of the HSV-1 strain P [HSV01(F)] and related mutants. Top line: The two covalently linked components of HSV-1 DNA, L and S, each consist of unique sequences flanked by inverted repeats (7, 31). The reiterated sequences flanking the L component designated as ab ad b'a' are each 9 kb in size, whereas the repeats flanking the S component are 6.3 kb in size (31). Line 2: expansion of portions of the inverted repeat sequences ab and b'a' containing the $\gamma_1 34.5$ and $\alpha 0$ genes. Line 3: sequence arrangement and restriction endonuclease sites in the expanded portions shown in line 2. Open box represents the 20 bp direct repeat sequence (DR1), flanking the A sequence (26,27). Restriction site designations are N,- NcoI; Be,- BstEII; S,- Sacd; St,- StuI. Line 4: the thin line and filled rectangle represent the transcribed and coding domains of the $\gamma_1 34.5$ gene (406). Vertical line, location of the transcription initiation sites of i$\gamma_1 34.5$ and of $\alpha 0$ genes. In the R3616 viral recombinant, one Kb was deleted between BstEII at 28th amino acid of $\gamma_1 34.5$ to StuI at the 3' terminus of the genes as shown. In HSV-1(F)R DNA, the sequences deleted from the $\gamma_1 34.5$ gene in R3616 were restored and therefore the virus could be expected to exhibit a wild-type phenotype. The R4009 recombinant virus DNA contains an in frame translation termination codons at the BstEII site. Vertical arrow on top points to the site of the stop codon insertion.

Viruses The isolation of herpes simplex virus 1 strain F, [HSV-1(F)] has been described by Ejercito et al. (*J. Gen. Virol.*, 2: 357–364 (1968) (incorporated herein by reference). The construction of recombinant viruses R3616, R4009, and HSV-1(F) was reported by Chou et al. (*Science*, 250: 1262–1266, Nov. 30, 1990) (incorporated herein by reference). As illustrated in FIG. 5, R3616 contains a 1 Kbp deletion in both copies of the $\gamma_1 34.5$ gene. In the recombinant R4009 a stop codon was inserted in both copies of the $\gamma_1 34.5$ gene. The $\gamma_1 34.5$ genes in the recombinant R3616 were restored to yield the recombinant HSV-1(F)R.

Virus Infection Cells were generally exposed to the viruses for 2 h at 37° C. at multiplicity of infection of 5 and then removed and replaced with the 199v media containing 1% calf serum. The infection continued at 37° C. for a length of time as indicated for each experiment. Cells were then either labeled for de novo protein synthesis or analysis of viral DNA and RNA.

$^{35}$S-methionine labeling At the indicated time post infection,, 50 uCi of $^{35}$S-methionine (specific activity>1,000 Cimmole, Amersham Co., Downers Grove, Ill.) was added to 1 ml of 199v media lacking methionine to cells in 6 well dishes. Labeling was continued for 1.5 hr, at which time cells were harvested. Preparation of cell extracts; separation of proteins by electrophoresis in denaturing polyacrylamide gels crosslinked with N,N' Diallytartardiamide (Bio-Rad Laboratories., Richmond, Calif.); transfer of polypeptides to nitrocellulose sheets; autoradiography and immunoblot with antibodies have been described by Ackermann et al., *J. Virol.*, 52: 108–118 (1984) (incorporated herein by reference).

Results

Figure 6A:
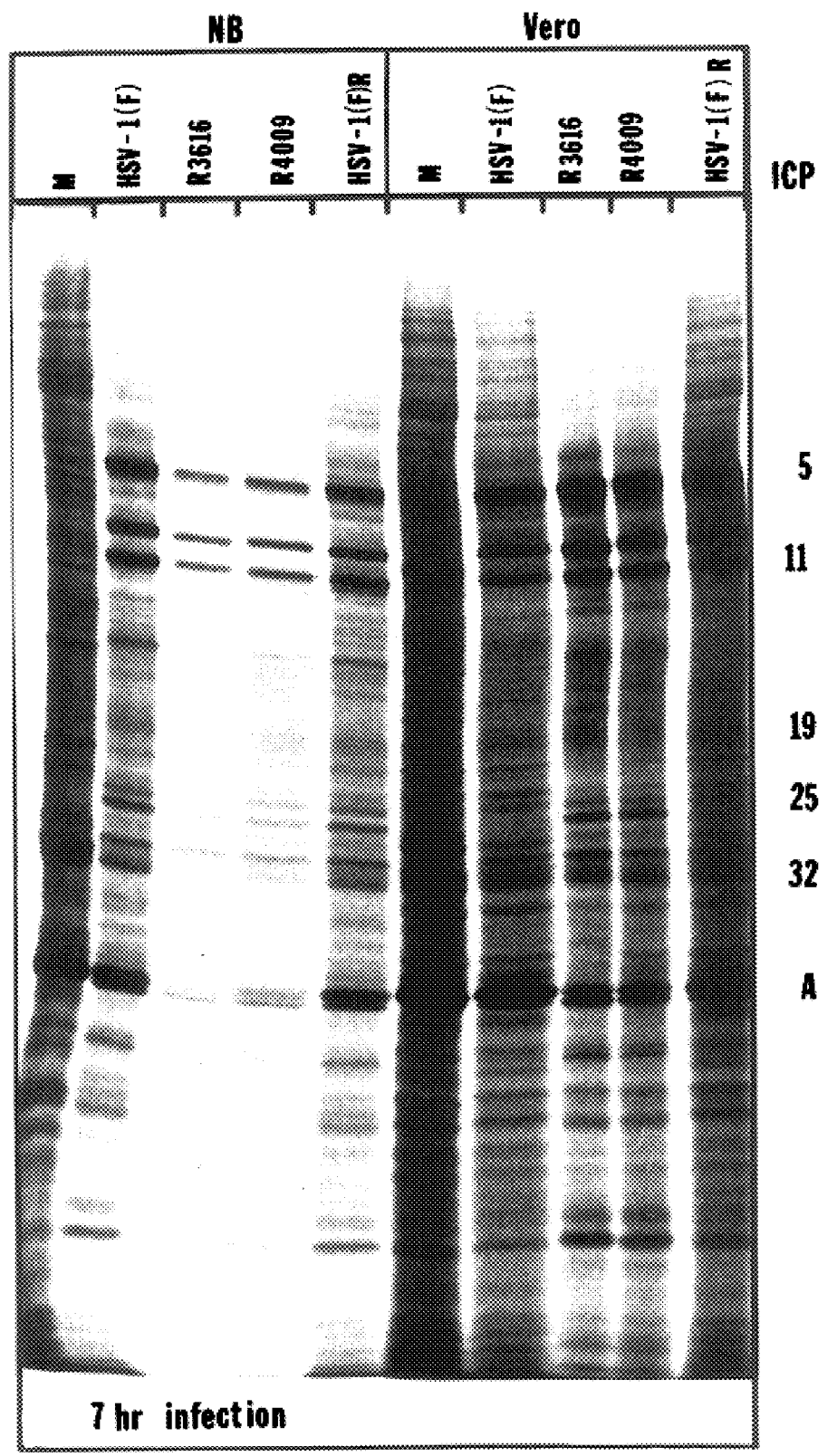
FIGS. 6a and 6b show an autoradiographic image of electrophoretically separated lysates of infected cells labeled for 90 minutes with $^{35}$S-methionine at stated time points. The SK-N-SH neuroblastoma and Vero cell lines were mock infected (M) or exposed at 37° C. to 5 pfu of wild-type or mutant viruses in 6 well (Costar, Cambridge, Mass.) dishes. At 2 hours post exposure, the cells were overlaid with mixture 199 supplemented with 1% calf serum. At 5.5 and 11.5 hours post exposure of cells to viruses, replicate infected 6 well cultures were overlaid with 1 ml of the 199v medium lacking unlabeled methionine but supplemented with 50 $\mu$Ci of $^{35}$S-methionine (specific activity >1,000 Ci/mmole, Amersham Co. Downers Grove, Ill.). After 90 minutes in labeling medium, the cells were harvested, solubilized in a buffer containing sodium dodecyl sulphate, subjected to electrophoresis on a denaturing 12% polyacrylamide gels crosslinked with N, N' Diallytartardiamide, electrically transferred to nitrocellulose sheet and subjected to autoradiography as previously described (13). Infected cell polypeptides (ICP) were designated according to Honess and Roizman, J. Virol., 12: 1347–1365 (1973).
Figure 6B:
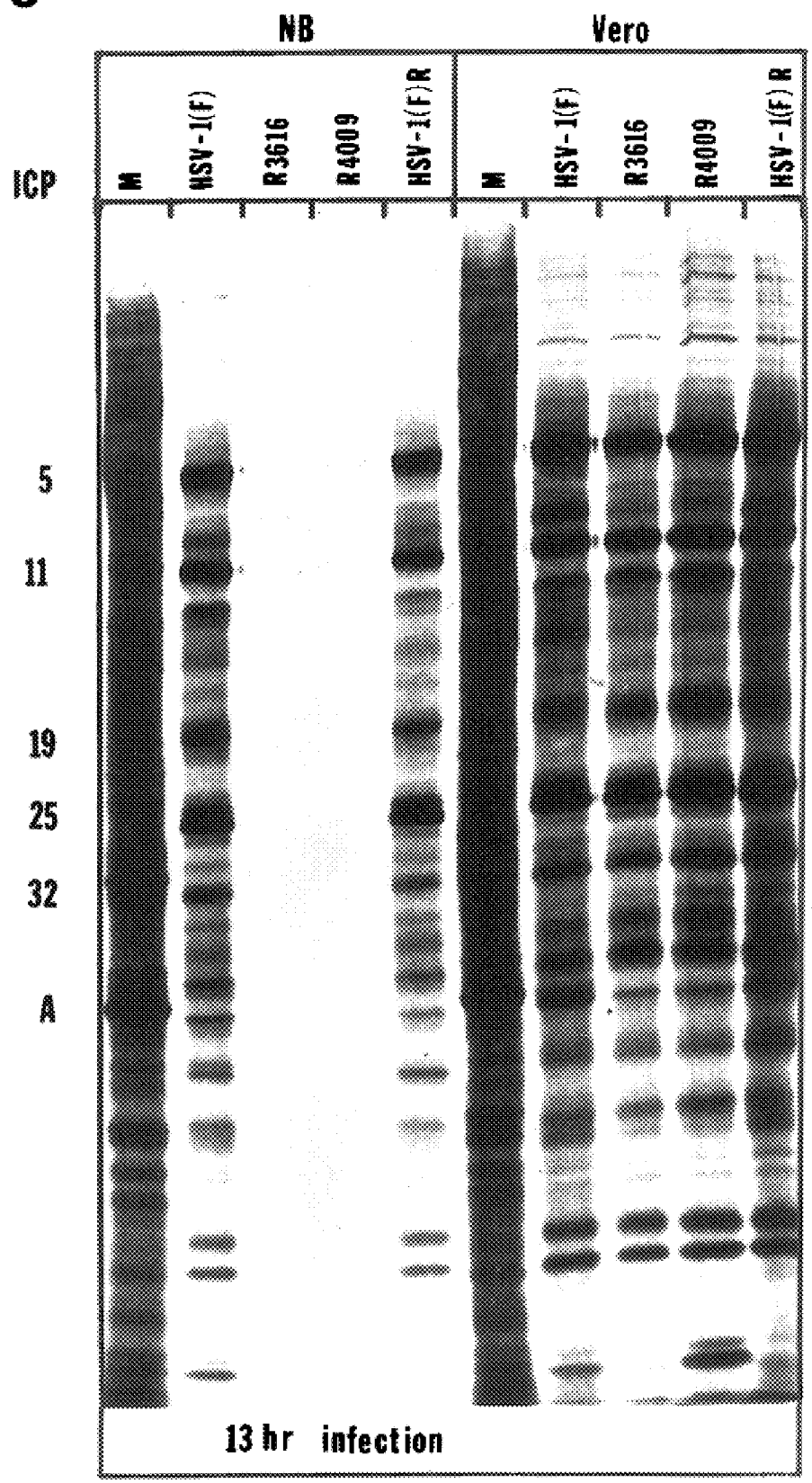

HSV-1 recombinant viruses lacking the $\gamma_1 34.5$ gene induce the shut off protein synthesis in neuroblastoma cells. In the course of screening human cell lines derived from CNS tissues it was apparent that the SK-N SH neuroblastoma cell lines produced 100 fold less mutant viruses than the fully permissive Vero cells. In was also noted, that the SK-N-SH neuroblastoma cells infected with R3616 or with R4009 exhibited reduced protein synthesis in cells harvested at 7 hours (FIG. 6a) and ceased to incorporate 3S-methionine by 13 hours (FIG. 6b) post infection. The phenomenon was observed in SK-N-SH neuroblastoma cells only, and could be attributed specifically to the mutations in the $\gamma_1 34.5$ gene inasmuch as restoration of the deleted sequences yielded a virus [HSV-1(F)R] which expressed viral proteins at 13 hour post infection (FIG. 6b) and exhibited the parental, wild type phenotype.

Figure 7A:
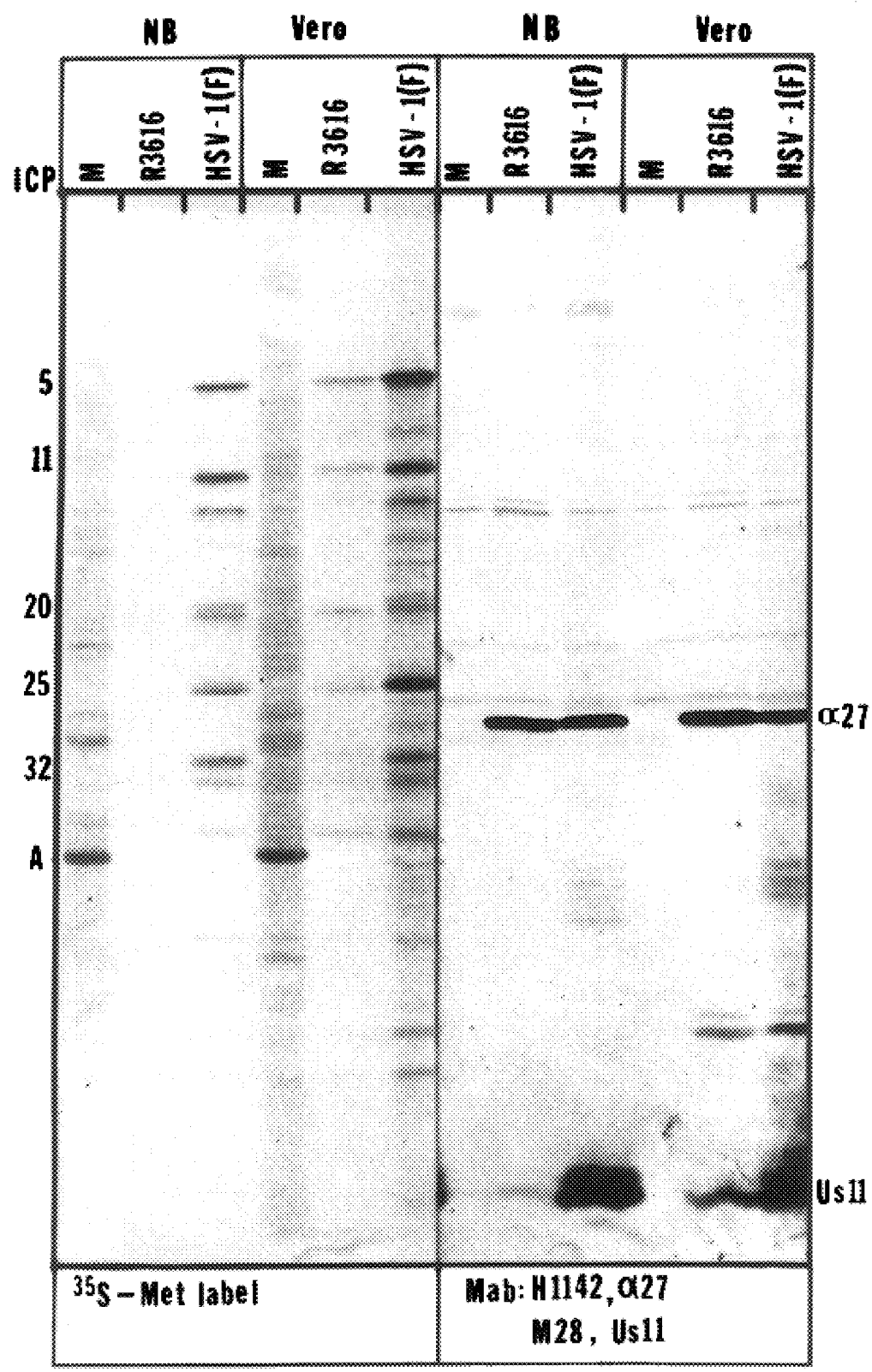
FIGS. 7a–7c show autoradiographic images of labeled polypeptides electrophoretically separated in denaturing gels and photographs of protein bands made apparent by their reactivity with antibodies. The SK-N-SH neuroblastoma and Vero cells were either mock infected (M) or infected with 5 pfu of either R3616 or the parent HSV-1(F) per cell as described in the legend to FIGS. 6a and 6b. The cultures were labeled for 1.5 hr before harvesting at 13th hr post exposure of cells to virus. Preparation of cell extracts, electrophoresis of the polypeptides, electric transfer of the separated polypeptides to a nitrocellulose sheet, and autoradiography were carried out as described elsewhere (Ackerman et al., J. Virol., 52: 108–118, 1984). The nitrocellulose sheets were reacted with the respective antibodies with the aid of kits from Promega, Inc. (Madison, Wis.) according to manufacture's instruction. Monoclonal antibodies H1142 against $\alpha$27 and H725 against the product of the $U_L 26.5$ gene were the generous gift of Lenore Pereira, University of California at San Francisco. The M28 monoclonal antibody to $U_S 11$ protein and the rabbit polyclonal antibody R161 against viral thymidine kinase ($\beta$tk) were made to a specific peptide (M. Sarmiento and B. Roizman, unpublished studies) in this laboratory. ICP designations were the same as noted before.
Figure 7B:
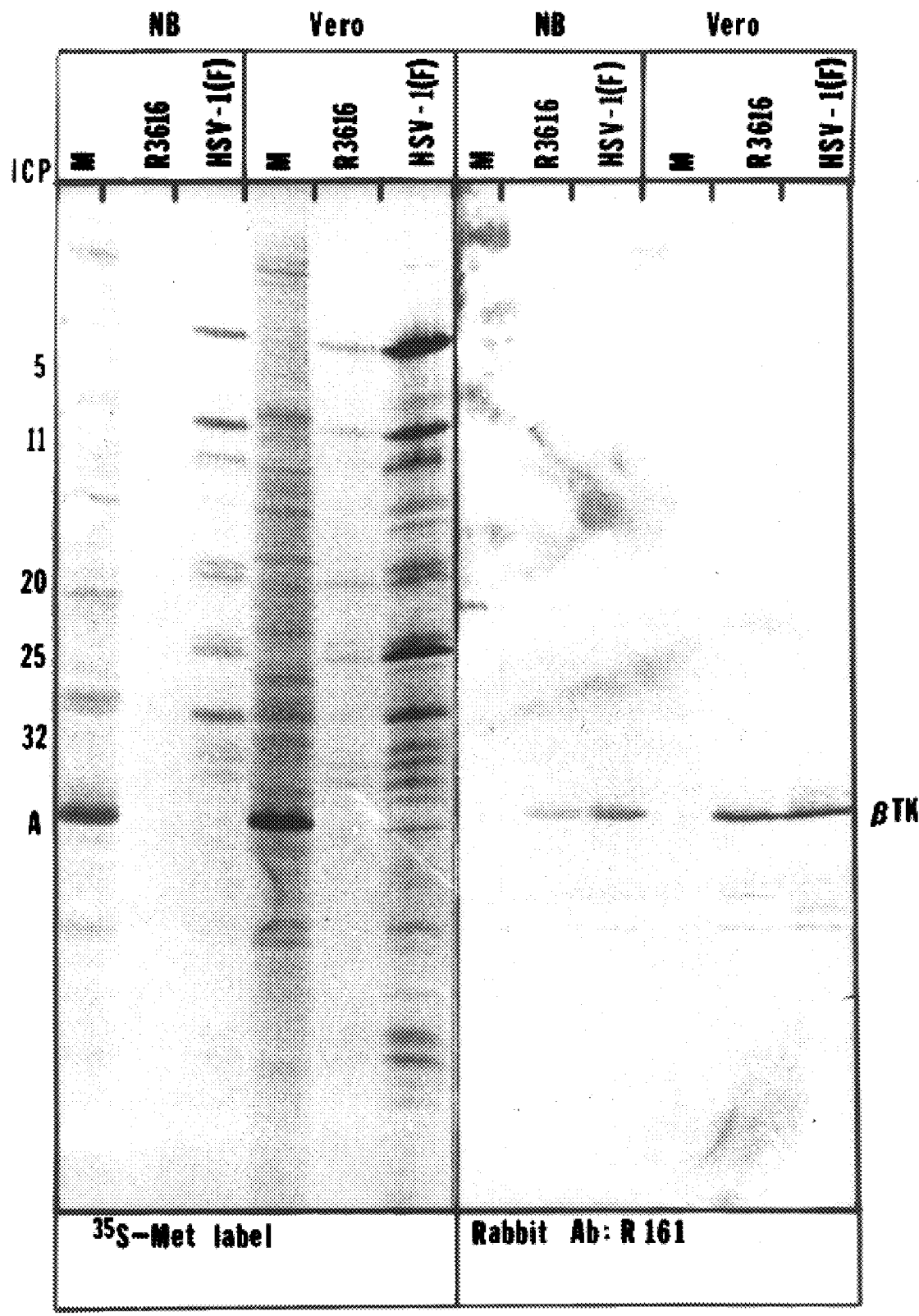
Figure 7C:
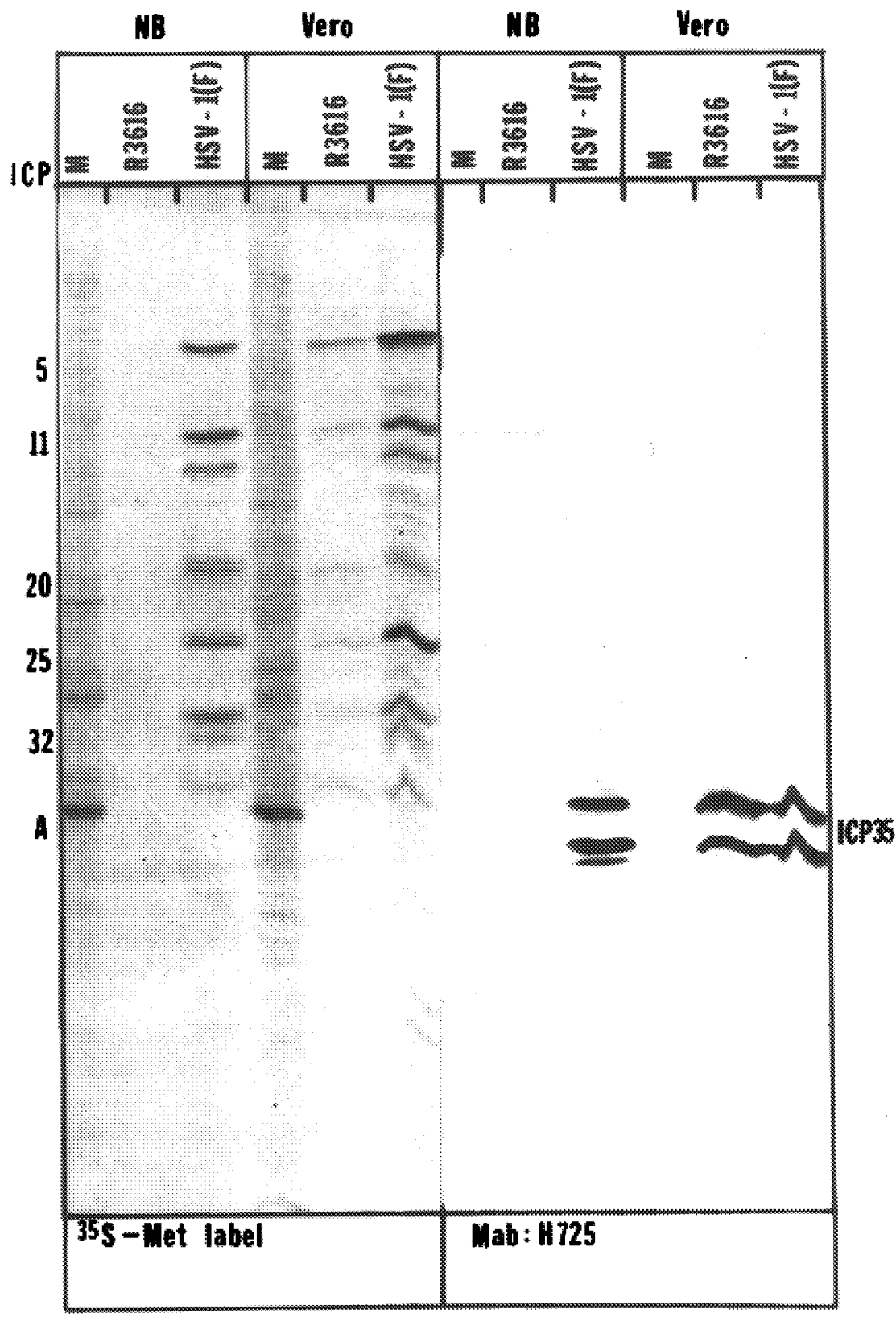

The shut off of protein synthesis occurred after the expression of α genes. Viral genes form three major groups whose expression is coordinately regulated and sequentially ordered in a cascade fashion. See Roizman and Sears, *Fields' Virology*, 2 ed., Fields et al., Ms, 1795–1841 (1990). The a genes do not require A novo protein synthesis for their expression, the β genes which are required for the synthesis of viral DNA require prior synthesis of functional α and β proteins and the onset of viral DNA synthesis. To determine the point at which expression of viral gene functions was terminated in SK-N-SH neuroblastoma cells infected with mutant viruses, infected cell lysates electrophoretically separated in denaturing polyacrylamide gels were transferred to a nitrocellulose sheet and probed with antibody to an α (α27), a β (viral thymidine kinase) and two abundant γ proteins. Roller and Roizman (*J. Virol.*, 6: 5873–5879 (1991) have shown that the latter were the products of $U_L 26.5$ and of $U_S 11$ genes whose expression at optimal levels requires viral DNA synthesis. As shown in FIGS. 7a–7c, the SK-N-SH neuroblastoma cells infected with the mutant viruses made normal amounts of α27 protein (FIG. 7a), reduced amounts of the thymidine kinase (β) protein (FIG. 7b), but no detectable γ proteins (FIGS. 7a and 7b). In contrast, both the wild type and mutant viruses could not be differentiated with respect to their capacity to replicate or to direct the synthesis of their proteins in Vero cells (FIGS. 7a–7c).

Figure 8:
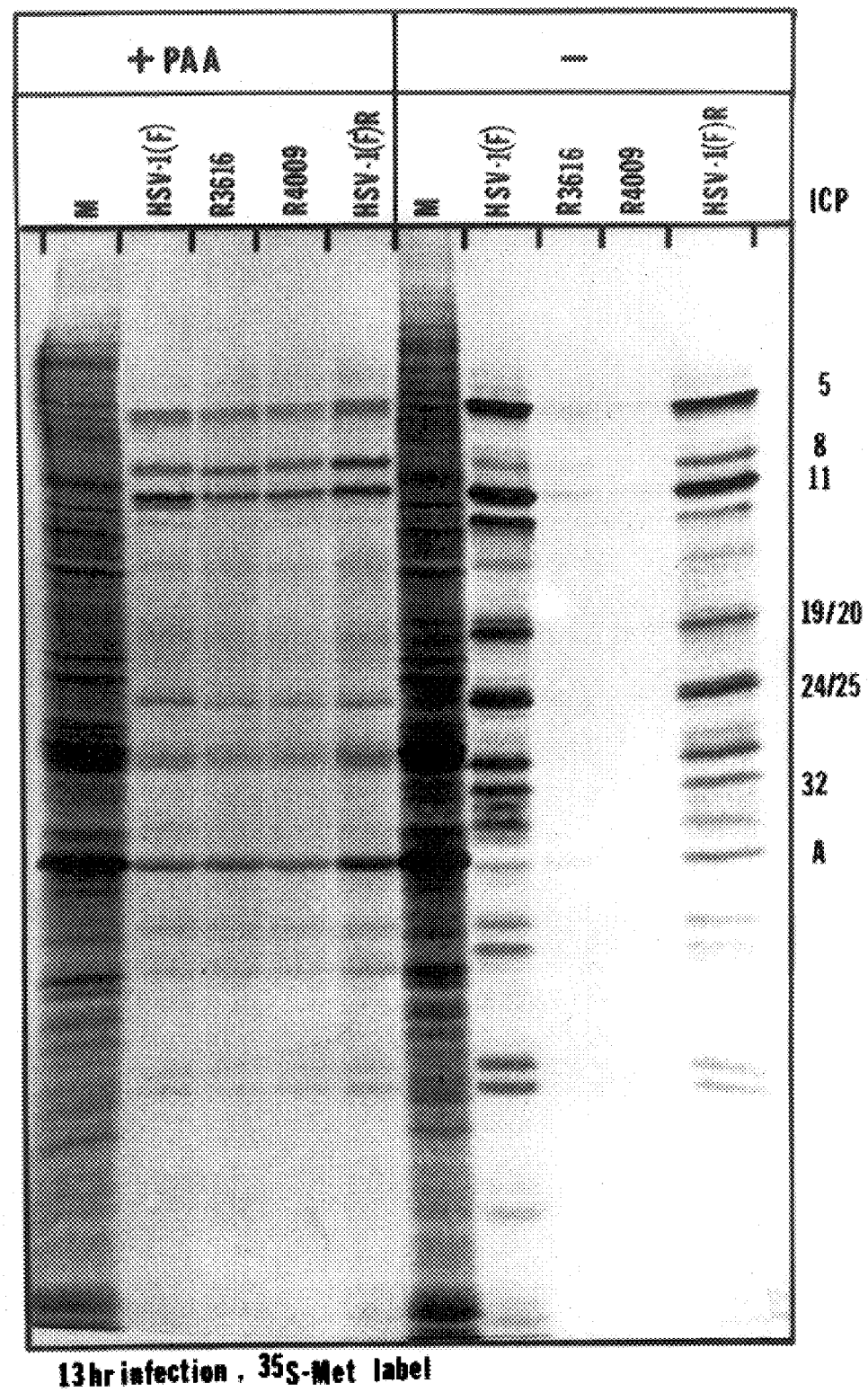
FIG. 8 shows an autoradiographic image of viral proteins expressed during infection on SK-N-SH neuroblastoma cell lines in the presence or absence of phosphonoacetate (PAA). Duplicate SK-N-SH neuroblastoma cell cultures were either treated with phosphonoacetate (300 $\mu$g/ml; Sigma Chemical Co., St. Louis, Mo.) starting at 1.5 hr prior to infection continuously until the termination of infection or left untreated. The cultures were either mock infected or exposed to 5 pfu of either HSV-1(F), R3616, R4009 and HSV-1(F)R at 5 pfu/cell. At 11.5 hours post exposure to virus, the cells were overlaid with medium containing 50 $\mu$Ci of $^{35}$S-methionine as described in legend to FIGS. 6a and 6b. Polypeptide extraction, electrophoresis on 12% polyacrylamide gels crosslinked with N,N' Diallytartardiamide, electrical transfer to nitrocellulose sheets and autoradiography were as described in the legend to FIG. 6.

The signal for shut off of protein synthesis is linked to viral DNA synthesis. These experiments were designed to determine whether the shutoff of protein synthesis was linked to a gene whose expression was dependent on viral DNA synthesis. The results of a key experiment are shown in FIG. 8. Replicate SK-N-SH and Vero cell cultures were infected with HSV-1(F) and recombinant viruses and maintained in the presence or absence of inhibitory concentrations of phosphonoacetate, a drug which blocks viral DNA synthesis. The cells were pulse labeled with $S^{35}$-methionine at 13 h post infection. The salient feature of the results were that protein synthesis in SK-N-SH cells infected with either R3616 or R4009 was sustained for at least 13 h in the presence of Phosphonoacetate but not in its absence. These results indicted that the signal for cessation of protein synthesis in SK-N-SH neuroblastoma cells infected with mutant viruses was associated with viral DNA synthesis or with a γ gene dependent on viral DNA synthesis for its expression.

Figure 9A:
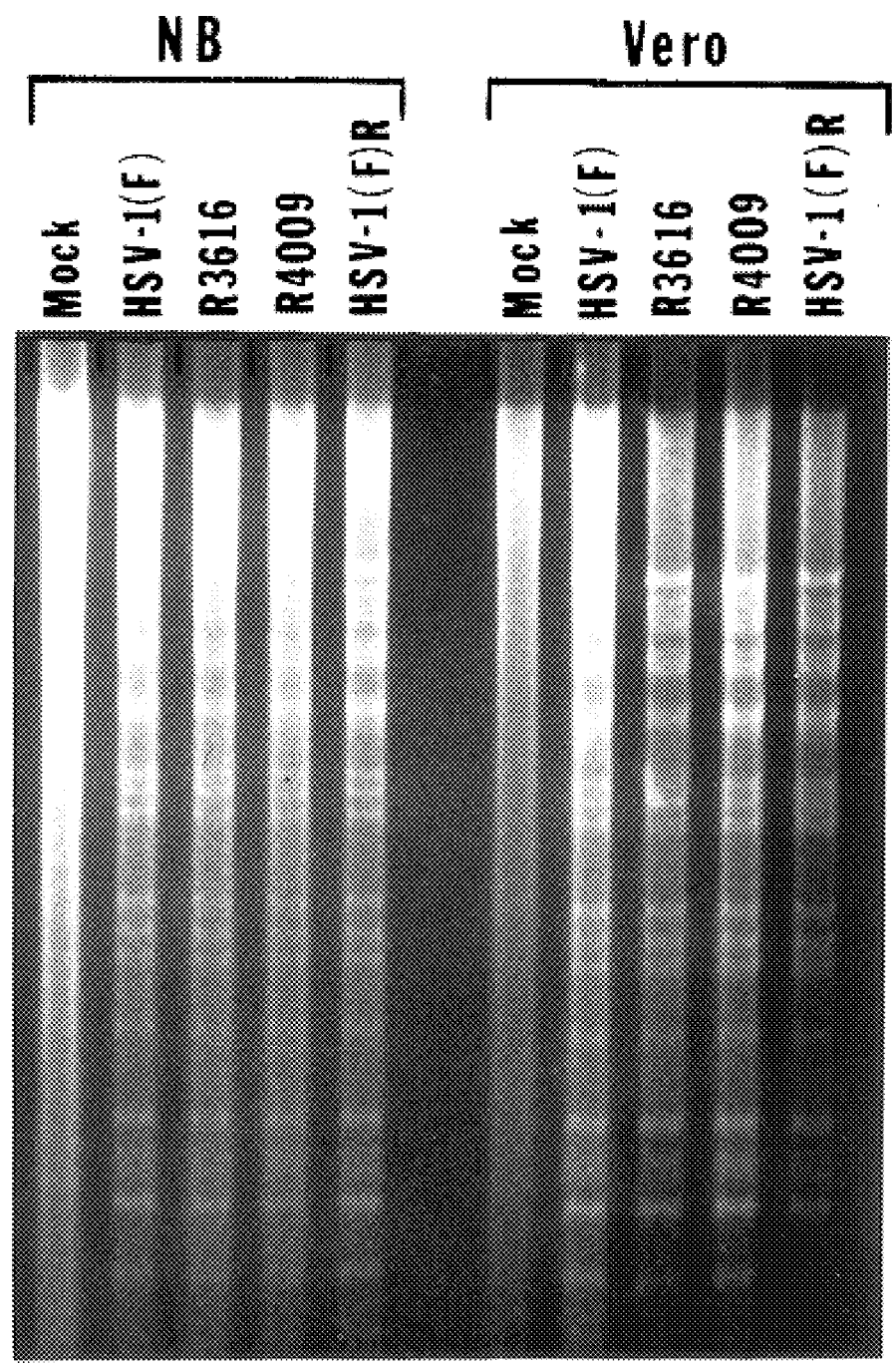
FIGS. 9a and 9b show viral DNA and RNA accumulation in infected SK-N-SH neuroblastoma and Vero cell cultures.
Figure 9B:

Human neuroblastoma cells infected with the $\gamma_1 34.5^-$ mutants synthesized viral DNA and accumulated late mRNA even though the shut off of protein synthesis precluded accumulation of late proteins. The evidence presented above indicated that in SK-N-SH neuroblastoma cells an event associated with viral DNA synthesis triggered the shut off of protein synthesis and that the late (γ) viral proteins did not accumulate. We expected, therefore, little or no accumulation of viral DNA and in the absence of viral DNA synthesis, little or no accumulation of late (γ)) viral transcripts whose synthesis is dependent on viral DNA synthesis. To our surprise, the amounts of viral DNA recovered from SK-N-SH neuroblastoma cells 17 hours post infection with mutant viruses were comparable to those obtained from wild type parent or repaired [(HSV-1)F)R] viruses (FIG. 9a). Furthermore, while the SK-N-SH neuroblastoma cells did not synthesize demonstrable amounts of U11 protein, the amounts of $U_S 11$ gene transcripts which accumulated in cells infected with mutant and wild type viruses were of similar magnitude (FIG. 9b).

The significance of these results stems from three observations. First, in infected cells, protein synthesis reflects a regulatory cascade; α protein synthesis is replaced by β and later by γ protein synthesis. In all cell lines other than the SK-N-SH neuroblastoma cells infected with the $\gamma_1 34.5$ mutants and tested to date, a block in the synthesis of one group of proteins does not lead to a cessation of total protein synthesis. For example, in cells treated with inhibitors of DNA synthesis like PAA, a subclass of γ proteins dependent for their synthesis on viral DNA synthesis is not made. However, in these cells, β protein synthesis continues beyond the time of their synthesis in untreated infected cells. The striking observations made in the studies on SK-N-SH cells infected with the $\gamma_1 34.5$ null mutants are that (i) all protein synthesis ceased completely, (ii) viral DNA was made and (iii) late, γ mRNA exemplified by $U_S 11$ mRNA was made even though protein synthesis ceased. These manifestations for viral replication have not been reported previously and are not characteristic of cells infected with wild type virus or any mutant virus infection of cells (e.g. Vero, HEp-2, baby hamster kidney, 143tk– and rabbit skin cell lines and human embryonic lung cells strain) other than those described in this report.

Second, the function of the $\gamma_1 34.5$ gene is to overcome this block in protein synthesis in SK-N-SH cells since repair of the mutation restores the wild type phenotype.

Lastly, while the association of cessation of protein synthesis with the onset of viral DNA replication does not exclude the possibility that a product made after infection is responsible of the shut off, the data does support the hypothesis that the cessation of protein synthesis is specifically caused by a known viral gene product interacting with the protein synthesizing machinery of the cell. For example, it has been well established that the product of the HSV-1 gene designated a vhs can shut off cellular protein synthesis after infection. vhs is a structural protein of the virus and is introduced into cells during infection. It destabilizes mRNA early in infection and its effects are not dependent on viral gene products made after infection. In the experiments set forth above, protein synthesis of wild type and mutant viruses could not be differentiated at 13 hours post infection in cells treated with Phosphonoacetate and hence the phenotype of mutant viruses cannot be attributed to the vhs gene product. This conclusion is reinforced by the observation that viral protein synthesis in SK-N-SH cells was not affected by increasing the multiplicity of infection with wild type virus to values as high as 100 pfu/cell (data not shown). A more likely source for the genetic information for the cessation of protein synthesis is the cell itself.

It has been reported that deprivation of growth factors from cells of neuronal origins results in programmed cell death, which manifests itself initially by the cessation of protein synthesis and subsequently by fragmentation of DNA. Apoptosis in lymphocytes is manifested by degradation of DNA. In the case of other herpes viruses, it has been shown that in B lymphocytes infected with the Epstein-Barr virus, the product of the viral LMP-1 gene induces the host gene Bcl-2 which precludes programmed lymphocyte death (Henderson et al, *Cell* 65: 1107–1991. Thus, it is apparent that the onset of viral DNA synthesis in neuronal cells triggers programmed cell death by cessation of protein synthesis and that HSV-1 $\gamma_1 34.5$ gene precludes this response.

The evolution of a HSV-1 gene which would preclude a response to a neuronal stress is not surprising. Infection of neurons, especially sensory neurons, is an essential feature of viral reproductive lifestyle which enables the HSV-1 to remain latent and to survive in human populations. If, as we propose, the function of $\gamma_1 34.5$ gene is to preclude cell death, the target of the gene would be neurons rather than lymphocytes since HSV normally infects nerve cells.

The $\gamma_1 34.5$ gene has several unusual features. The gene lacks a conventional TATAA box or response elements frequently associated with TATAA-less transcriptional units. The sequence which enables the expression of the gene is 12 bp long but repeated as many as 3 times in the wild type strain used in this laboratory. Various assays reported elsewhere indicate that the amounts of gene products produced in cells of non neuronal derivation are smaller than those expressed by most vial genes and that the amounts of the protein made in the, absence of viral DNA synthesis were smaller than those made in its presence. The gene is predicted to encode a protein of 263 amino acids. It contains the triplet Ala-Thr-Pro repeated. 10 time and accumulates in the cytoplasm. A recent note indicates that 63 amino acid residues near, the carboxyl terminus of the $\gamma_1 34.5$ protein shares 83% identity with a mouse protein MyD116 found in a myeloid leukemic cell line induced to differentiate by interleukin 6 (Lord et al., Nucleic Acid Res. 18: 2823, 1990). The function of MyD116 is unknown. The results presented above demonstrate that the product of the $7\gamma_1 34.5$ gene, the protein ICP34.5, quite clearly enables sustained protein synthesis in SK-N-SH neuroblastoma cells, and it is clear that the gene's expression is sufficient to preclude apoptosis.

The promoter-regulatory elements essential for the expression of $\gamma_1 34.5$ are contained within three elements of the a sequence, i.e. the direct repeats DR2 and DR4 and the unique $U_b$ sequences. Gel retardation assays failed to show binding of the product of the $\alpha 4$ gene encoding the major regulatory protein of the virus to any of the elements regulating expression of the $\gamma_1 34.5$ gene. In transient expression assays, the product of the $\alpha 4$ or of $\alpha 0$ genes failed to transactivate a chimeric reporter gene consisting of the coding sequences of the thymidine kinase gene fused to the 5' non-coding sequences of the $\gamma_1 34.5$ gene. The reporter gene was induced, but to a relatively low level by co-transfection with plasmids containing both $\alpha 4$ and $\alpha 0$ genes. The plasaid encoding the $\alpha 27$ gene had no effect on the expression of the chimeric reporter gene transfected alone although it reduced the induction of the chimeric gene by plasmids containing the $\alpha 0$ and $\alpha 4$ genes.

EXAMPLE 2

TREATMENT OF PROGRAMMED CELL DEATH (APOPTOSIS) WITH GENE THERAPY

In this example, $\gamma_1 34.5$ gene therapy directed toward the prevention or treatment of apoptosis is described. For the purposes of this example mutated HSV-1 virus is proposed as a vector for introduction of the gene into neuronal cells undergoing or about to undergo programmed cell death. It is also envisioned that this embodiment of the present invention could be practiced using alternative viral or phage vectors, including retroviral vectors and vaccinia viruses whose genome has been manipulated in alternative ways so as to render the virus non-pathogenic. The methods for creating such a viral mutation are set forth in detail in U.S. Pat. No. 4,769,331, incorporated herein by reference. Furthermore, it is also envisioned that this embodiment of the present invention could be practiced using any gene whose expression is beneficial in gene therapy, and use of the non-HSV viruses would allow gene therapy in non-neural systems.

Herpes simplex virus has a natural tropism for human CNS tissue. Under wild type conditions, the virus is capable of replicating and multiplying in the nervous system and is neurovirulent. The virus can also establish latent infection in the neurons and can be occasionally reactivated. To establish a vector system for delivery of genes into neurons, the proposed construct of an HSV vector must satisfy the following criteria: 1. Such a vector should have a natural tropism for CNS and brain tissue. 2. Such a vector should be non-pathogenic; that is, totally avirulent and not reactivatable to cause an infection. 3. Such a vector should consist of constitutive expression of $\gamma_1 34.5$ to prevent cell death in cells undergoing neurodegeneration. 4. Such a vector so proposed in 3 is suitable for additional foreign gene insertion for gene therapy.

Material and Methods

A HSV vector with a mutational lesion in the $\alpha 4$ gene is constructed. The proposed virus will no longer be able to replicate, multiply and reactivate from latent infection in the CNS. The virus can, in the absence of $\alpha 4$ gene, establish a latent infection in the neuron. This virus can be obtained by co-transfection of viral DNA with plasmid containing a $\alpha 4$ expressing cell line. $\alpha 4$ expressing cell lines and the virus have been reported previously. DeLuca et al., *J. Virol.*, 56: 558–570 (1985).

Additionally, such an HSV vector with $\gamma_1 34.5$ gene under a constitutive expression promoter is also envisioned this constitutive expression promoter can be the HSV LAT promoter, the LTR promoter of retrovirus or any other foreign promoter specific for naural gene expression. Such a viral vector properly introduced is suitable for prevention of cell death in neuronal cells undergoing apoptosis.

Moreover, such an HSV vector with foreign genes inserted at a neutral location on the viral genome is suitable for delivery of foreign genes into target neurons and for CNS gene therapy. The procedures to generate the above recombinant viruses are those published by Post and Roizman (*Cell*, 2: 227, 1991) incorporated herein by reference. See also U.S. Pat. No. 4,769,331, incorporated herein by reference.

In instances where use of the mutated HSV-1 virus is appropriate the virus can be combined with a pharmaceutically acceptable carrier such as buffered saline and injected at the site of peripheral nerve endings whose axons originate from neural cell bodies undergoing or about to undergo apoptosis. As will be recognized by those skilled in the medical arts the amount of virus administered will vary depending upon several factors, including the vector's ability to target the cells requiring treatement, the extent to which the gene is expressed in the target tissue, and the activity of the expressed protein among others. An innoculum containing approximately $10^4$–$10^5$ viruses in phosphate buffered saline or skim milk has produced successful results in mice. Virus so injected is taken up into the peripheral nerve endings and is then transported via retrograde axonal transport to the neuronal cell bodies. In instances where such peripheral injection is not useful or appropriate, localized intraspinal or intraventricular injection, or direct microinjection of the virus could be utilized.

An appropriately altered non-HSV virus, one with a genome manipulated in such a way as to render the virus non-pathogenic, could be used in a similar manner. Direct microinjection or peripheral injection for delivery to the cell body via retrograde axonal transport are options for viral delivery. Finally, it should also be noted that a biological functional equivalent gene could be utilized for gene therapy in any vector described in this example.

EXAMPLE 3

USE OF MULTI-POTENT NEURAL CELL LINES TO DELIVER THE 1434.5 GENE TO THE CNS

In addition to the viral vector delivery system to CNS and brain tissue, another vector system has been developed recently using cell lines passaged in vitro and engrafting these cells back to the animal. These procedures involve taking cells of fetal or postnatal CNS origin, immortalizing and transforming them in vitro and transplanting the cells back into the mouse brain. These cells, after engraftment, follow the migration pattern and environmental cue of normal brain cell development and differentiate in a nontumorigenic, cytoarchitecturally appropriate manner. This work has been examplified in several articles notably Snyder et al., *Cell,* 68: 33–51, 1992 and Ranfranz et al., *Cell,* 6: 713–729, 1991. Utilizing appropriately modified techniques, it is possible to introduce the $\gamma_1 34.5$ gene alone or in combination with other gene of interest into the cells and engraft. Such a procedure allows the delivery of the genes to its natural site. Proper expression of the $\gamma_1 34.5$,gene in these neurons should result in prevention of cell death in neurodegeneration and preserving cells carrying foreign genes suitable for gene therapy.

Materials and Methods

Propagation of Cerebellar Cell Lines Cerebellar cell lines are generated as described by Ryder et al. (*J. Neurobiol.* 21: 356–375, 1990). Lines are grown in Dulbecco's modified Eagle's medium supplemented with 10% fetal calf serum (Gibco), 5% horse serum (Gibco), and 2 mM glutamine on poly-L-lysine (PLL) (Sigma) (10 µgml)-coated tissue culture dishes (Corning). The lines are maintained in a standard humidified, 37° C., 5% $CO_2$-air incubator and are either fed weekly with one-half conditioned medium from confluent cultures and one-half fresh medium or split (1:10 or 1:20) weekly or semiweekly into fresh medium.

Transduction of Cerebellar Progenitor Lines with $\gamma_1 34.5$ gene A recent 1:10 split of the cell line of interest is plated onto 60 mm tissue culture plates. Between 24 and 48 hr after plating, the cells are incubated with the replication-incompetent retroviral vector BAG containing the -myc gene ($10^6$–$10^7$ colony-forming units [cfu]/ml) plus 8 µg/ml polybrene for 1–4 hr for introduction of the $\gamma_1 34.5$ gene alone or in combination with other suitable genes for gene therapy, along with the neomycin G418 marker. Cells are then cultured in fresh feeding medium for approximately 3 days until they appear to have undergone at least two doublings. The cultures are then trypsinized and seeded at low density (50–5000 cells on a 100 mm tissue culture dish). After approximately 2 weeks well-separated colonies are isolated by brief exposure to trypsin within plastic cloning cylinders. Colonies are plated in 24-well PLL-coated Costar plates. At confluence, these cultures are passaged to 60 mm tissue culture dishes and expended. A representative dish from each subclone is stained directly in the culture dish using X-gel histochemistry (see Price et al., 1967; Cepko, 1989a, 1989b). The percentage of blue cells is determined under the microscope. Subclones with the highest percentage of blue cells (ideally >90%; at least >50%) are maintained, characterized, and used for transplantation.

Tests for Virus Transmission The presence of helper virus is assayed by measurement of reverse transcriptase activity in supernatants of cells lines as described by Goff et al. (1981) and by testing the ability of supernatants to infect NIH 3T3 cells and generate G418-resistant colonies of X-gal$^+$ colonies (detailed in Cepko, 1989a, 1989b). All cerebellar cell lines used for transplantation are helper virus-free as judged by these methods.

Coculture of Neural Cell Lines with Primary Cerebellar Tissue Primary dissociated cultures of neonatal mouse cerebellum are prepared as in Ryder et al. (1990) and seeded at a density of $2 \times 10^6$ to $4 \times 10^6$ cells per PLL-coated eight-chamber Lab Tek glass or plastic slide (Miles). After the cells settled (usually 24 hr), 10% of a nearly confluent 10 cm dish of the neural cell line of interest is seeded, following trypsinization, onto the slide. The coculture is re-fed every other day and grown in a 50% $CO_2$-air, humified incubator until 8 or 14 days of coculture.

Preparation of Calls Lines for Transplantation Cells from a nearly confluent but still actively growing dish of donor cells are washed twice with phosphate-buffered saline (PBS), trypsinized, gently triturated with a wide-bore pipette in serum-containing medium (to inactivate the trypsin), gently pelleted (1100 rp for 1 min in a clinical centrifuge), and resuspended in 5 ml of PBS. Washing by pelleting and resuspension of fresh PBS is repeated twice, with the cells finally resuspended in a reduced volume of PBS to yield a high cellular concentration (at least $1 \times 10^6$ cells per µl). Trypan blue (0.05% w/v) is added to localize the inoculum. The suspension is kept well triturated, albeit gently, and maintained on ice-prior to transplantation to minimize clumping.

Injections into Postnatal Cerebellum Newborn CD-1 or CF-1 mice are cryoanesthetized, and the cerebellum is localized by transillumination of the head. Cells are administered either via a Hamilton 10 µl syringe with a beveled 33-gauge needle or a drawn glass micropipette with a 0.75 mm inner diameter and 1.0 mm outer diameter generated from borosilicate capillary tubing (FHC, Brunswick, Me.) by a Flaming Brown Micropipette Puller (Model p-87, Sutter Instruments) using the following parameters: heat 750, pull 0, velocity 60, time 0. Best results are achieved with the glass micropipette. The tip is inserted through the skin and skull into each hemisphere and vermis of the cerebellum where the cellular suspension was injected (usually 1–2 µl per injection). Typically, the following situation should exist: $1 \times 10^7$ cells per ml of suspension; $\times 10^6$ to $2 \times 10^6$ cells per injection; one injection in each cerebellar hemisphere and in the vermis. Importantly, the cellular suspension, maintained on ice throughout, is gently triturated prior to each injection in order to diminish clumping and to keep cells suspended.

The injection of BAG virus was performed as described for the cell suspension. The BAG virus stock ($8 \times 16^7$ G418-resistant cfu/ml) contained, in addition to trypan blue, polybrene at 8 µg/ml.

EXAMPLE 4

TREATMENT OF PROGRAMMED CELL DEATH (APOPTOSIS) WITH ICP34.5

As an alternative to the gene therapy methods described for exemplary purposes in Examples 2 and 3, neuronal cells undergoing or about to undergo programmed cell death can also be treated with the protein expressed by the $\gamma_1 34.5$ gene, i.e. ICP34.5. Alternatively, a biological functional equivalent protein could be used in such treatment.

For example, ICP34.5 is isolated from cells expressing the protein and purified using conventional chromatography purification and immunoaffinity purification methods described by Ackerman et al. (*J. Virol.* 58: 843–850, 1986, incorporated herein by reference). The purified protein is next combined with a pharmaceutically appropriate carrier, such as buffered saline or purified distilled water. For administration, the pharmaceutical composition can be injected in one of several ways, as appropriate: (i) intraspinal injection; (ii) intraventricular injection; (iii) direct injection into the area containing the neurons undergoing or about to undergo programmed cell death or any other appropriate method of administration understood by those skilled in the art. Such treatment would be particularly appropriate in the surgical repair of severed peripheral nerves, and the use of proteins as therapeutic agents is well within the current level of skill in the medical arts in light of the present specification.

EXAMPLE 5

ASSAYS FOR CANDIDATE SUBSTANCES FOR PREVENTION OF PROGRAMMED CELL DEATH (APOPTOSIS)

The $\gamma_1 34.5$ gene of herpes simplex virus enables the virus to replicate, multiply and spread in the central nervous system and the brain so that the virus is neurovirulent to the host. Recombinant virus lacking the gene lost this ability to penetrate the CNS of the host and become totally avirulent. In examining the nature of this avirulent phenotype in culture, the mutant virus lacking the gene exhibited a total translation shutoff phenotype characteristic of programmed cell death. This mechanism of programmed cell death afforded by the host cell greatly reduced the ability of the virus to multiply and spread. The function of $\gamma_1 34.5$ in the virus therefore is to inactivate the programmed death of the cell (anti-apoptosis) thereby restoring translation and enabling the virus to replicate to full potential in the host.

This anti-apoptotic effect of $\gamma_1 34.5$ was further examined and its ability to protect neural cells from other environmental stresses which lead to apoptosis was discovered. These environmental stresses include UV, nerve grown factor deprivation and neuronal cell differentiation. This Example describes the use of the $\gamma_1 34.5$ gene and its protective function to screen for pharmaceutical agents and drugs that mimic the in vivo function of $\gamma_1 34.5$ to prevent neurodegeneration. Such a screening procedure constitutes construction of cell lines expressing $\gamma_1 34.5$ and a null cell line without the gene and measurement of the viability of the cells after stress treatment by induction of a reporter gene. This can be a host gene promoter tagged by a fluorescence indicator or any other easily assayable marker to signal viability.

Materials and Methods

A test neuroblastoma cell line is established constitutively expressing $\gamma_1 34.5$ and containing a fluorescence tagged (e.g., the a sequence promoter fused to lacZ) cellular gene, or any tag that provides the easily assayable marker to signal viability. A neuroblastoma null cell line consisting of a-lacZ indicator gene and the same host indicator gene is also established, along with a Vero cell line consisting of a-lacZ indicator gene and the same host indicator gene. Environmental stresses are then applied that normally would (1) trigger the a sequence promoter activation; (2) trigger the protection afforded by $\gamma_1 34.5$ as signaled by viability after stress treatment; and (3) trigger cell programmed death in the absence of $\gamma_1 34.5$. Candidate substances of pharmaceutically appropriate drugs and agents can be tested in such an assay. The proposed scheme of the assay for scoring of positive candidates is shown in outline form in Table 2.

TABLE 2

EXPERIMENTAL FLOW CHART: ASSAY FOR CANDIDATE SUBSTANCE ABLE TO PREVENT PROGRAMMED CELL DEATH

| | CELL LINES | ACTION | EXPECTATION |
|---|---|---|---|
| A. | neuroblastoma cells constitutively express $\gamma_1 34.5$ and a second inducible promoter-indicator gene | stress followed by induction of second promoter | viability as measured by induction of a reporter gene hours after stress |
| B. | neuroblastoma cells expressing a-lacZ and a second inducible promoter | stress followed by induction of second promoter | 1. apoptosis related stress: a-lacZ induced; second promoter not induced 2. toxicity: no induction of a-lacZ and the second inducible promoter |
| C. | vero cells expressing a-lacZ and a second inducible promoter gene | stress followed by induction | 1. a-lacZ not induced 2. toxicity factor excluded, determined from expression of inducible second promoter |

EXAMPLE 6

ASSAY FOR CANDIDATE SUBSTANCES FOR ACTIVATION OF PROGRAMMED CELL DEATH (APOPTOSIS) FOR TREATMENT OF CANCER OR TUMOROGENIC DISEASES AND FOR SUPPRESSION OF HSV INFECTION

In order to induce cell death in tumor cells, it is desirable to block the expression of the anti-apoptosis gene or the activity of the protein expressed by the gene. As such, it is desirable to develop procedures that will allow screening for candidate substances which trigger cell death in tumor cells. In addition, since expression of the $\gamma_1 34.5$ gene of HSV-1 has been shown to prevent apoptosis in neuronal cells so that the virus can replicate, multiply and spread in the CNS (that is, so that the virus can become neurovirulent), a substance capable of blocking $\gamma_1 34.5$ expression or inhibiting the action of ICP34.5 can be expected to supress HSV neurovirulence (or the virulence of other viruses relying on a similar mechanism) by allowing apoptosis to occur in infected neurons.

It has been found that the protection afforded by $\gamma_1 34.5$ can be extended to protect other cells from environmental stresses, and indeed the gene has a generalized anti-apoptotic effect. The promoter for the gene $\gamma_1 34.5$ lies in the a sequence of HSV and, at time of stress, the promoter is activated. It can be assumed that the a sequence promoter contains apoptosis responsive elements and cellular factors (transcription factors in particular) that mediate the expression of anti-apoptosis gene are apoptotic in nature. These cellular factors are therefore the targets of the present assay to screen for drugs or agents that would inactivate their ability to induce the anti-apoptosis gene. The assay involves the use of the a sequence promoter and its inducibility by conditions which induce apoptosis as an indicator assay which screens for therapeutic agents and drugs capable of blocking the expression of the anti-apoptosis gene and therefore allow the cell to die of programmed cell death.

A test plasaid construct bearing the A sequence and coding sequence up to the 28th amino acid of $\gamma_1 34.5$ is fused to the lacZ reporter gene or any other readily assayable reporter gene. The construct is introduced into a neuroblastoma or PC12 cell line by G418 selection and a clonal and continuous cell line for screening purposes is established. A control plasmid construct bearing an HSV late promoter, a promoter which would normally not be expressed in cell lines and which further would not be induced to express by apoptosis-inducing stress is fused to the same indicator gene. This construct is also introduced into a continuous clonal cell line and serves as a control for the test cell line. Environmental stresses that trigger the a sequence promoter activation and that cause programmed cell death are then defined. These conditions include UV injury, virus infection, nerve growth factor deprivation, and the influence of antibodies on cell surface receptors, among others. Candidate substances or pharmaceutically appropriate drugs and agents are then tested in assays for their ability to block the a sequence promoter activation at time of stress.

The assay of the present invention allows the screening and identification of pharmaceutically appropriate drugs and agents targeted at various cellular factors that induce the expression of anti-apoptosis gene. By inactivating essential cellular factors, these agents should be able to allow cell programmed death to occur. Such positive candidates would then be appropriately administered (via intravenous, intrathecal, or direct injection, or via oral administration) in order to induce programmed cell death in tumor cells, in neurons infected with the herpes virus, or in cells infected with a virus the virulence of which is dependent upon an anti-apoptotic effect. The use of proteins and other chemotherapeutic substances in antitumor therapy is well known in the art, and therefore, it is considered that the use and dosages of candidate substances for treatment of tumorogenic diseases (e.g., cancer) or herpes infection is well within the skill of the present state of the medical arts in light of the present specification. See U.S. Pat. Nos. 4,457,916; 4,529,594; 4,447,355; and 4,477,245, all incorporated herein by reference. These positive candidates can also be used to identify intermediates in the pathways leading to cell programmed death.

Materials and Methods

W5 cell lines are established in 96 well culture dishes coated with collagen. Control cell lines containing the promoter fusion element are also established in such 96 well dishes. The test candidate substances are added to the medium in individual wells containing both the test and control cell lines set up in 96 well dishes. The cells are then briefly exposed to UV or other stresses. 8 hr post stress induction, cells are washed with PBS-A twice, and fixed with 0.5 ml containing 2% (v/v) formaldehyde and 0.2% glutaraldehyde in PBS for 5 min at room temperature. The cells are rinsed again with PBS and then stained with 2 ml 5 mM potassium ferrocyanide, 5 mM potassium ferrocyanide, 2 mM $MgCl_2$ and 1 mg/ml X-gal (diluted from a 40 mg/ml stock solution in dimethyl sulfoxide) in PBS. Cells expressing β-Galactosidase were stained blue after incubation at 37° C. for 2–3 days.

Results

The construct described above with the lacZ reporter gene was introduced into PC12 cell line. A new cell line W5 was clonally established by G418 selection. The W5 cell line was then tested for activation of the a sequence promoter under suboptimal conditions names in 3 above. The results are: (a) The above cells, when exposed briefly to UV for 2 minutes, turn blue upon staining the fixed cells with X-gal at 6–10 hr post UV exposure. (b) The above cells, when exposed to HSV-1(F) virus at multiplicity of infection of 5, also turn blue upon staining at 8 hr post infection. (c) The above cells turn light blue when nerve growth factor (rat, 7S) is introduced into the medium to allow differentiation processes. (d) The cells turn darker blue when Nerve, Growth Factor is removed from the medium after differentiation is complete and the cells have become dependent on nerve growth factor for survival. (e) Little or no difference in color development is seen in cells starved for serum (0% fetal bovine serum) and those fully supplied in 10% fetal bovine serum. (f) The above experiments are repeated with control promoter fusion elements to control for the true inhibition of anti-apoptosis gene expression rather than toxicity-induced cell death. By this procedure, the positive candidates that can induce cell death in cells will therefore render the following phenotypes: (i) Introduction of stress to the test cell line in the absence of this substance will give rise to blue colored cells. (ii) Introduction of stress to the test cell line in the presence of same substance will give rise to white cells. (iii) Introduction of stress to control cell lines with our without this putative substance will have no effect on the color of cells.

The present invention has been disclosed in terms of specific embodiments which are believed by the inventors to be the best modes for carrying out the invention. However, in light of the disclosure hereby provided, those of skill in the various arts will recognize that modifications can be made without departing from the intended scope of the invention. The exemplary embodiments set forth herein and all other modifications and embodiments are intended to be within the scope and spirit of the present invention and the appended claims.

REFERENCES CITED

Ackerman et al., *J. Virol.*, 58: 843 (1986)
Ackermann et al., *J. Virol.*, 52: 108–118 (1984)
Centifanto-Fitzgerald et al. *J. Exp. Med.*, 155: 475, 1982
Chou and Roizman *Cell,* 41: 803–811, 1985
Chou and Roizman *J. Virol.*, 64: 1014–1020, 1990
Chou et al., *Science,* 5: 1212–1266, 1990
Clem et al. Science, 245: 1388–1390, Nov. 29, 1991
Corey and Spear, *N. Eng. J. Med.*, 3: 686–691, 1986
DeLuca et al., *J. Virol.*, 5: 558–570 (1985)
Ejercito et al. *J. Gen. Virol.*, 2: 357–364 (1968)
Hayward et al., *Proc. Natl. Acad. Sci. USA,* 72: 4243–4247 (1975)
Henderson et al. *Cell,* 65: 1107–1115, 1991
Honess and Roizzan (*J. Virol.*, 12: 1346 (1973)
Honess and Roizman, *J. Virol.*, 12: 1347–1365 (1973)

Hubenthal-Voss et al., *J. Virol.,* 62: 454 (1988)
Itoh et al., *Cell* 66: 233–243 (1991)
Javier et al. (*J. Virol.,* 65: 1978, 1987) and Thompson et al. *Virology,* 172: 435, 1989
Johnson et al., *Neurobiol. of Aging,* 10: 549–552, 1989
Katz et al., *J. Virol.,* 64: 4288–4295
Kyte et al., *J. Mol. Biol.,* 157: 105–132, 1982
Lord et al., *Nucleic Acid Res.* 18: 2823, 1990
Mackem and Roizzan, *J. Virol.,* 44: 934–947 (1982)
McGeoch et al., *J. Gen. Virol.,* 64: 1531–1574 (1988)
Meignier et al., *J. Infect. Dis.,* 158: 602 (1988)
Peppel and Baglioni *BioTechniques,* 9: 711–712, 1990
Post and Roizman *Cell,* 25: 227, 1981
Ranfranz et al., *Cell,* 6: 713–729, 1991
Roizman and Sears, Fields' *Virology,* 2 ed., Fields et al., Eds, 1795–1841 (1990)
Roller and Roizran *J. Virol.,* 65: 5873–5879 (1991)
Ryder et al. *J. Neurobiol.* 21: 356–375, 1990
Sentman et al. *Cell,* 67: 879–88, Nov. 29, 1991
Snyder et al., *Cell,* 68: 33–51, 1992
Strasser et al. *Cell,* 67: 889–899, Nov. 29, 1991
Taha et al. *J. Gen. Viral.,* 70: 705, 1989
Wadsworth et al., *J. Virol.,* 15: 1487–1497 (1975)
Williams, *Cell,* 85; 1097–1098

What is claimed is:

1. A method of treating tumorigenic disease in a mammal comprising the step of administering at or near a site of a tumor of said tumorigenic disease a herpes simplex virus vector lacking an expressible $\gamma_1$ 34.5 gene, whereby the growth of said tumor is suppressed.

2. The method of claim 1 wherein the $\gamma_1$34.5 gene comprises a stop codon in reading frame.

3. The method of claim 1 wherein the $\gamma_1$34.5 gene comprises a deletion mutation.

4. The method of claim 1 wherein the herpes simplex Virus vector is HSV-1.

5. The method of claim 1 wherein the herpes simplex virus vector is HSV-2.

6. The method of claim 1 wherein the herpes simplex virus vector is administered via direct injection into said tumor of said tumorigenic disease.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TTTAAAGTCG CGGCGGC                                                     17
```

(2) INFORMATION FOR SEQ ID NO:2:

(i) SEQUENCE CHARACTERISTICS:
      (A) LENGTH: 133 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
GCAGCCCGGC CCCCCGCGGC CGAGACGAGC GAGTTAGACA GGCAAGCACT ACTCGCCTCT      60

GCACGCACAT GCTTGCCTGT CAAACTCTAC CACCCCGGCA CGCTCTCTGT CTCCATGGCC     120

CGCCGCCGCC GCC                                                       133
```

(2) INFORMATION FOR SEQ ID NO:3:

(i) SEQUENCE CHARACTERISTICS:
      (A) LENGTH: 291 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

```
ATCGCGGCCC CCGCCGCCCC CGGCCGCCCG GGCCCACGGG CGCCGTCCCA ACCGCACAGT      60

CCCAGGTAAC CTCCACGCCC AACTCGGAAC CCGCGGTCAG GAGCGCGCCC GCGGCCGCCC     120

CGCCGCCGCC CCCCGCCAGT GGGCCCCCGC CTTCTTGTTC GCTGCTGCTG CGCCAGTGGC     180

TCCACGTTCC CGAGTCCGCG TCCGACGACG ACGATGACGA CGACTGGCCG GACAGCCCCC     240

CGCCCGAGCC GGCGCCAGAG GCCCGGCCCA CCGCCGCCGC CCCCCGCCCC C             291
```

(2) INFORMATION FOR SEQ ID NO:4:

(i) SEQUENCE CHARACTERISTICS:
        (A) LENGTH: 595 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
ACCGCCCGGC GCGGGCCCGG GGGGCGGGGC TAACCCCTCC CACCCCCCCT CACGCCCCTT    60
CCGCCTTCCG CCGCGCCTCG CCCTCCGCCT GCGCGTCACC GCAGAGCACC TGGCGCGCCT   120
GCGCCTGCGA CGCGCGGGCG GGGAGGGGGC GCCGGAGCCC CCCGCGACCC CCGCGACCCC   180
CGCGACCCCC GCGACCCCCG CGACCCCCGC GACCCCCGCG ACCCCCGCGA CCCCCGCGAC   240
CCCCGCGACC CCCGCGCGGG TGCGCTTCTC GCCCCACGTC CGGGTGCGCC ACCTGGTGGT   300
CTGGGCCTCG GCCGCCCGCC TGGCGCGCCG CGGCTCGTGG GCCCGCGAGC GGGCCGACCG   360
GGCTCGGTTC CGGCGCCGGG TGGCGGAGGC CGAGGCGGTC ATCGGGCCGT GCCTGGGGCC   420
CGAGGCCCGT GCCCGGGCCC TGGCCCGCGG AGCCGGCCCG GCGAACTCGG TCTAACGTTA   480
CACCCGAGGC GGCCTGGGTC TTCCGCGGAG CTCCCGGGAG CTCCGCACCA AGCCGCTCTC   540
CGGAGAGACG ATGGCAGGAG CCGCGCATAT ATACGCTGGG AGCCGGCCCG CCCCC        595
```

(2) INFORMATION FOR SEQ ID NO:5:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GAGGCGGGCC CGCCCTCGGA GGGCGGGACT GGCCAATCGG CGGCCGCCAG CGCGGCGGGG    60
CCCGGCCAAC CAGCGTCCGC CGAGTCTTCG GGGCCCGGCC CACTGGGCGG GAGTTACCGC   120
CCAGTGGGCC GGGCCGCCCA CTTCCCGGTA TGGTAATTAA AAACTTACAA GAGGCCTTGT   180
TCCGCTTCCC GGTATGGTAA TTAGAAACTC ATTAATGGGC GGCCCCGGCC GCCCTTCCCG   240
CTTCCGGCAA TTCCCGCGGC CCTTAATGGG CAACCCCGGT ATTCCCCGCC T            291
```

(2) INFORMATION FOR SEQ ID NO:6:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTTAAAGCGG TGGCGGCGGG CAGCCCGGGC CCCCCGCCGA GACTAGCGAG TTAGACAGGC    60
AAGCACTACT CGCCTCTGCA CGCACATGCT TGCCTGTCAA ACTCTACCAC CCCGGCACGC   120
TCTCTGTCTC CATGGCCCGC CGCCGCCGCC                                   150
```

(2) INFORMATION FOR SEQ ID NO:7:

(i) SEQUENCE CHARACTERISTICS:
        (A) LENGTH: 503 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

| | | | | | |
|---|---|---|---|---|---|
| ATCGCGGCCC | CCGCCGCCCC | CGGCCGCCCG | GGCCCACGGG | CGCCGTCCCA | ACCGCACAGT | 60 |
| CCCAGGTAAC | CTCCACGCCC | AACTCGGAAC | CCGCGGTCAG | GAGCGCGCCC | GCGGCCGCCC | 120 |
| CGCCGCCGCC | CCCCGCCGGT | GGGCCCCCGC | CTTCTTGTTC | GCTGCTGCTG | CGCCAGTGGC | 180 |
| TCCACGTTCC | CGAGTCCGCG | TCCGACGACG | ACGATGACGA | CGACTGGCCG | GACAGCCCCC | 240 |
| CGCCCGAGTC | GGCGCCAGAG | GCCCGGCCCA | CCGCCGCCGC | CCCCCGCCCC | CCGGGCCCCC | 300 |
| ACCGCCCGGC | GTGGGCCCGG | GGGGCGGGGC | TGACCCCTCC | CACCCCCCCT | CGCGCCCCTT | 360 |
| CCGCCTTCCG | CCGCGCCTCG | CCCTCCGCCT | GCGCGTCACC | GCGGAGCACC | TGGCGCGCCT | 420 |
| GCGCCTGCGA | CGCGCGGGCG | GGGAGGGGGC | GCCGGAGCCC | CCGCGACCCC | CCGCGACCCC | 480 |
| CGCGACCCCC | GCGACCCCCG | CGA | | | | 503 |

(2) INFORMATION FOR SEQ ID NO:8:

(i) SEQUENCE CHARACTERISTICS:
        (A) LENGTH: 368 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| CCCCCGCGAC | CCCCGCGCGG | GTGCGCTTCT | CGCCCCACGT | CCGGGTGCGC | CACCTGGTGG | 60 |
| TCTGGGCCTC | GGCCGCCCGC | CTGGCGCGCC | GCGGCTCGTG | GGCCCGCGAG | CGGGCCGACC | 120 |
| GGGCTCGGTT | CCGGCGCCGG | GTGGCGGAGG | CCGAGGCGGT | CATCGGGCCG | TGCCTGGGGC | 180 |
| CCGAGGCCCG | TGCCCGGGCC | CTGGCCCGCG | GAGCCGGCCC | GGCGAACTCG | GTCTAACGTT | 240 |
| ACACCCGAGG | CGGCCTGGGT | CTTCCGCGGA | GCTCCCGGGA | GCTCCGCACC | AAGCCGCTCT | 300 |
| CCGGAGAGAC | GATGGCAGGA | GCCGCGCATA | TATACGCTTG | GAGCCAGCCC | GCCCTCACAG | 360 |
| GGCGGGCC | | | | | | 368 |

(2) INFORMATION FOR SEQ ID NO:9:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| | | | | | |
|---|---|---|---|---|---|
| GGGCGGGACT | GGCCAATCGG | CGGCCGCCAG | CGCGGCGGGG | CCCGGCCAAC | CAGCGTCCGC | 60 |
| CGAGTCTTCG | GGGCCCGGCC | CATTGGGCGG | GAGTTACCGC | CCAATGGGCC | GGGCCGCCCA | 120 |
| CTTCCCGGTA | TGGTAATTAA | AAACTTGCAA | GAGGCCTTGT | TCCGCTTCCC | GGTATGGTAA | 180 |
| TTAGAAACTC | ATTAATGGGC | GGCCCCGGCC | GCCCTTCCCG | CTTCCGGCAA | TTCCCGCGGC | 240 |
| CCTTAATGGG | CAACCCCGGT | ATTCCCCGCC | T | | | 271 |

(2) INFORMATION FOR SEQ ID NO:10:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TTTAAAGTCA C                                                          11
```

(2) INFORMATION FOR SEQ ID NO:11:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
AGCGGCGGGC AGCCCCCCCG CGGCCGAGAC TAGCGAGTTA GACAGGCAAG CACTACTCGC     60
CTCTGCACGC ACATGCTTGC CTGTCAAACT CTACCACCCC GGCACGCTCT CTGTCTCCAT    120
GGCCCGCCGC CGCCGCCGCC ATCGCGGCCC CCGCCGCCCC CGGCCGCCCG GGCCCACGGG    180
CGCGGTCCCA ACCGCACAGT CCCAGGTAAC CTCCACGCCC AACTCGGAAC CCGTGGTCAG    240
GAGCGCGCCC GCGGCC                                                    256
```

(2) INFORMATION FOR SEQ ID NO:12:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GGTGGGCCCC CGCCTTCTTG TTCGCTGCTG CTGCGCCAGT GGCTCCACGT TCCCGAGTCC     60
GCGTCCGACG ACGACGATGA CGACGACTGG CCGGACAGCC CCCCGCCCGA GCCGGCGCCA    120
GAGGCCCGGC CCACCGCCGC CGCCCCCCGC CCCC                                154
```

(2) INFORMATION FOR SEQ ID NO:13:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
ACCGCCCGGC GCGGGCCCGG GGGGCGGGGC TAACCCCTCC CACCCCCCCT CACGCCCCTT     60
CCGCCTTCCG CCGCGCCTCG CCCTCCGCCT GCGCGTCACC GCGGAGCACC TGGCGCGCCT    120
GCGCCTGCGA CGCGCGGGCG GGGAGGGGGC GCCGAAGCCC CCCGCGACCC CGCGACCCC     180
CGCGACCCCC GCGACCCCCG CGACCCCGC GA                                   212
```

(2) INFORMATION FOR SEQ ID NO:14:

(i) SEQUENCE CHARACTERISTICS:
        (A) LENGTH: 356 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

| | | | | | |
|---|---|---|---|---|---|
| CCCCCGCGAC | CCCCGCGCGG | GTGCGCTTCT | CGCCCCACGT | CCGGGTGCGC | CACCTGGTGG | 60 |
| TCTGGGCCTC | GGCCGCCCGC | CTGGCGCGCC | GCGGCTCGTG | GGCCCGCGAG | CGGGCCGACC | 120 |
| GGGCTCGGTT | CCGGCGCCGG | GTGGCGGAGG | CCGAGGCGGT | CATCGGGCCG | TGCCTGGGGC | 180 |
| CCGAGGCCCG | TGCCCGGGCC | CTGGCCCGCG | GAGCCGGCCC | GGCGAACTCG | GTCTAACGTT | 240 |
| ACACCCGAGG | CGGCCTGGGT | CTTCCGCGGA | GCTCCCGGGA | GCTCCACACC | AAGCCGCTCT | 300 |
| CCGGAGAGAC | GATGGCAGGA | GCCGCGCATA | TATACGCTGG | GAGCCGGCCC | GCCCCC | 356 |

(2) INFORMATION FOR SEQ ID NO:15:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

| | | | | | |
|---|---|---|---|---|---|
| GAGGCGGGCC | CGCCCTCGGA | GGGCGGGACT | GGCCAATCGG | CGGCCGCCAG | CGCGGCGGGG | 60 |
| CCCGGCCAAC | CAGCGTCCGC | CGAGTCGTCG | GGGCCCGGCC | CACTGGGCGG | TAACTCCCGC | 120 |
| CCAGTGGGCC | GGGCCGCCCA | CTTCCCGGTA | TGGTAATTAA | AAACTTGCAA | GAGGCCTTGT | 180 |
| TCCGCTTCCC | GGTATGGTAA | TTAGAAACTC | ATTAATGGGC | GGCCCCGGCC | GCCCTTCCCG | 240 |
| CTTCCGGCAA | TTCCCGCGGC | CCTTAATGGG | CAACCCCGGT | ATTCCCCGCC | T | 291 |

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TTTAAAGCGC                                                              10

(2) INFORMATION FOR SEQ ID NO:17:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

| | | | | | |
|---|---|---|---|---|---|
| GGCGGCGGGC | AGCCCCCCCG | CGGCCGAGAC | TAGCGAGTTA | GACAGGCAAG | CACTACTCGC | 60 |
| CTCTGCACGC | ACATGCTTGC | CTGTCAAACT | CTACCACCCC | GGCACGCTCT | CTGTCTCCAT | 120 |
| GGCCCGCCGC | CGCCGCCGCC | ATCGCGGCCC | CCGCCGCCCC | CGGCCGCCCG | GGCCCACGGG | 180 |

```
CGCGGTCCCA ACCGCACAGT CCCAGGTAAC CTCCACGCCC AACTCGGAAC CCGTGGTCAG    240

GAGCGCGCCC GCGGCCGCCC CGCCGCCGCC CCCCGCCGGT GGGCCCCCGC CTTCTTGTTC    300

GCTGCTGCTG CGGCAGTGGC TCCAGGTTCC GGAGTCCGCG TCCGACGACG ACGATGACGA    360

CGACTGGCCG GACAGCCCCC CGCCCGAGCC GGCGCCAGAG GCCCGGCCCA CCGCCGCCGC    420

CCCCCGCCCC C                                                         431

(2) INFORMATION FOR SEQ ID NO:18:

(i) SEQUENCE CHARACTERISTICS:
        (A) LENGTH: 212 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

ACCGCCCGGC GCGGGCCCAG GGGGCGGGGC TGACCCCTCC CACCCCCCCT CACGCCCCTT     60

CCGCCTTCCG CCGCGCCTCG CCCTCCGCCT GCGCGTCACC GCAGAGCACC TGGCGCGCCT    120

GCGCCTGCGA CGCGCGGGCG GGGAGGGGGC GCCGGAGCCC CCCGCGACCC CCGCGACCCC    180

CGCGACCCCC GCGACCCCCG CGACCCCCGC GA                                  212

(2) INFORMATION FOR SEQ ID NO:19:

(i) SEQUENCE CHARACTERISTICS:
        (A) LENGTH: 356 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CCCCCGCGAC CCCCGCGCGG GTGCGCTTCT CGCCCCACGT CCGGGTGCGC CACCTGGTGG     60

TCTGGGCCTC GGCCGCCCGC CTGGCGCGCC GCGGCTCGTG GGCCCGCGAG CGGGCCGACC    120

GGGCTCGGTT CCGGCGCCGG GTGGCGGAGG CCGAGGCGGT CATCGGGCCG TGCCTGGGCC    180

CCAAGGCCCG CGCCCGGGCC CTGGCCCGCG GAGCCGGCCC GGCGAACTCG GTCTAACGTT    240

ACACCCGAGG CGGCCTGGGT CTTCCGCGGA GCTCCCGGGA GCTCCACACC AAGCCGCTCT    300

CCGGAGAGAC GATGGCAGGA GCCGCGCATA TATACGCTGG GAGCCGGCCC GCCCCC        356

(2) INFORMATION FOR SEQ ID NO:20:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GAGGCGGGCC CGCCCTCGGA GGGCGGGACT GGCCAATCGG CGGCCGCCAG CGCGGCGGGG     60

CCCGGCCAAC CAGCGTCCGC CGAGTCGTCG GGGCCCGGCC CACTGGGCGG TAACTCCCGC    120

CCAGTGGGCC GGGCCGCCCA CTTCCCGGTA TGGTAATTAA AAACTTGCAA GAGGCCTTGT    180

TCCGCTTCCC GGTATGGTAA TTAGAAACTC ATTAATGGGC GGCCCCGGCC GCCCTTCCCG    240

CTTCCGGCAA TTCCCGCGGC CCTTAATGGG CAACCCCGGT ATTCCCCGCC T             291
```

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GTAACCTAGA CTAGTCTAGC                                                     20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GTTACGCTAG ACTAGTCTAG                                                     20

(2) INFORMATION FOR SEQ ID NO:23:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CCCGGACATG GAACGAGTAC GACGACGCAG CCGACGCCGC CGGCGACCGG GCCCCGGG       58

(2) INFORMATION FOR SEQ ID NO:24:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CTGCTCATGC TGCTGCGTCG GCTGCGGCGG CCGCTGGCCC GGGGCCCGTA C             51

(2) INFORMATION FOR SEQ ID NO:25:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

Met Ala Arg Arg Arg Arg
1             5

(2) INFORMATION FOR SEQ ID NO:26:

(i) SEQUENCE CHARACTERISTICS:
        (A) LENGTH: 258 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

His Arg Gly Pro Arg Arg Pro Arg Pro Pro Gly Pro Thr Gly Ala Val
1               5                   10                  15

Pro Thr Ala Gln Ser Gln Val Thr Ser Thr Pro Asn Ser Glu Pro Ala
            20                  25                  30

Val Arg Ser Ala Pro Ala Ala Ala Pro Pro Pro Pro Ala Ser Gly
        35                  40                  45

Pro Pro Pro Ser Cys Ser Leu Leu Leu Arg Gln Trp Leu His Val Pro
    50                  55                  60

Ala Glu Ser Ala Ser Asp Asp Asp Asp Asp Asp Trp Pro Asp Ser
65                  70                  75                  80

Pro Pro Pro Glu Pro Ala Pro Glu Ala Arg Pro Thr Ala Ala Ala Pro
            85                  90                  95

Arg Pro Arg Ser Pro Pro Gly Ala Gly Pro Gly Gly Gly Ala Asn
                100                 105                 110

Pro Ser His Pro Pro Ser Arg Pro Phe Arg Leu Pro Pro Arg Leu Ala
            115                 120                 125

Leu Arg Leu Arg Val Thr Ala Glu His Leu Ala Arg Leu Arg Leu Arg
    130                 135                 140

Arg Ala Gly Gly Glu Gly Ala Pro Glu Pro Pro Ala Thr Pro Ala Thr
145                 150                 155                 160

Pro Ala Thr Pro Ala Thr Pro Ala Thr Pro Ala Thr Pro Ala Thr Pro
            165                 170                 175

Ala Thr Pro Ala Thr Pro Ala Thr Pro Ala Arg Val Arg Phe Ser Pro
            180                 185                 190

His Val Arg Val Arg His Leu Val Val Trp Ala Ser Ala Ala Arg Leu
    195                 200                 205

Ala Arg Arg Gly Ser Trp Ala Arg Glu Arg Ala Asp Arg Ala Arg Phe
210                 215                 220

Arg Arg Arg Val Ala Glu Ala Glu Ala Val Ile Gly Pro Cys Leu Gly
225                 230                 235                 240

Pro Glu Ala Arg Ala Arg Ala Leu Ala Arg Gly Ala Gly Pro Ala Asn
            245                 250                 255

Ser Val (2) INFORMATION FOR SEQ ID NO:27:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Met Ala Arg Arg Arg Arg
1               5

(2) INFORMATION FOR SEQ ID NO:28:

```
    (i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

His Arg Gly Pro Arg Pro Arg Pro Pro Gly Pro Thr Gly Ala Val
1               5                   10                  15

Pro Thr Ala Gln Ser Gln Val Thr Ser Thr Pro Asn Ser Glu Pro Ala
            20                  25                  30

Val Arg Ser Ala Pro Ala Ala Ala Pro Pro Pro Pro Ala Gly Gly
            35                  40                  45

Pro Pro Pro Ser Cys Ser Leu Leu Leu Arg Gln Trp Leu His Val Pro
        50                  55                  60

Glu Ser Ala Ser Asp Asp Asp Asp Asp Asp Trp Pro Asp Ser Pro
65                  70                  75                  80

Pro Pro Glu Ser Ala Pro Glu Ala Arg Pro Thr Ala Ala Ala Pro Arg
                85                  90                  95

Pro Pro Gly Pro His Arg Pro Ala Trp Ala Arg Gly Ala Gly Leu Thr
            100                 105                 110

Pro Pro Thr Pro Pro Arg Ala Pro Ser Ala Phe Arg Arg Ala Ser Pro
        115                 120                 125

Ser Ala Cys Ala Ser Pro Arg Ser Thr Trp Arg Ala Cys Ala Cys Asp
    130                 135                 140

Ala Arg Ala Gly Arg Gly Arg Arg Ser Pro Pro Arg Pro Pro Arg Pro
145                 150                 155                 160

Pro Arg Pro Pro Arg Pro Pro Arg Pro
                165

(2) INFORMATION FOR SEQ ID NO:29:

(i) SEQUENCE CHARACTERISTICS:
        (A) LENGTH: 180 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Pro Arg Gly Cys Ala Ser Arg Pro Thr Ser Gly Cys Ala Thr Trp Trp
1               5                   10                  15

Ser Gly Pro Arg Pro Ala Trp Arg Ala Ala Arg Gly Pro Ala
            20                  25                  30

Ser Gly Pro Thr Gly Leu Gly Ser Gly Ala Gly Trp Arg Arg Pro Arg
            35                  40                  45

Arg Ser Ser Gly Arg Ala Trp Gly Pro Arg Pro Val Pro Gly Pro Trp
        50                  55                  60

Pro Ala Glu Pro Ala Arg Arg Thr Arg Ser Asn Val Thr Pro Glu Ala
65                  70                  75                  80

Ala Trp Val Phe Arg Gly Ala Pro Gly Ser Ser Ala Pro Ser Arg Ser
                85                  90                  95

Pro Glu Arg Arg Trp Gln Glu Pro Arg Ile Tyr Thr Leu Gly Ala Ser
            100                 105                 110

Pro Pro Ser Gln Gly Gly Pro Pro Arg Gly Arg Asp Trp Pro Ile Gly
```

```
            115                 120                 125
Gly Arg Gln Arg Gly Gly Ala Arg Pro Thr Ser Val Arg Val Phe
            130                 135                 140
Gly Ala Arg Pro Ile Gly Arg Glu Leu Pro Pro Asn Gly Pro Gly Arg
145                 150                 155                 160
Pro Leu Pro Gly Met Val Ile Lys Asn Leu Gln Glu Ala Leu Phe Arg
                    165                 170                 175
Phe Pro Val Trp
            180
```

(2) INFORMATION FOR SEQ ID NO:30:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Met Ala Arg Arg Arg Arg Arg His Arg Gly Pro Arg Arg Pro Arg Pro
1               5                   10                  15
Pro Gly Pro Thr Gly Ala Val Pro Thr Ala Gln Ser Gln Val Thr Ser
                20                  25                  30
Thr Pro Asn Ser Glu Pro Val Val Arg Ser Ala Pro Ala Ala
            35                  40                  45
```

(2) INFORMATION FOR SEQ ID NO:31:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Gly Gly Pro Pro Pro Ser Cys Ser Leu Leu Leu Arg Gln Trp Leu His
1               5                   10                  15
Val Pro Glu Ser Ala Ser Asp Asp Asp Asp Asp Asp Asp Trp Pro Asp
                20                  25                  30
Ser Pro Pro Pro Glu Pro Ala Pro Glu Ala Arg Pro Thr Ala Ala Ala
            35                  40                  45
Pro Arg Pro Arg Ser Pro Pro Gly Ala Gly Pro Gly Gly Ala
50                  55                  60
Asn Pro Ser His Pro Pro Ser Arg Pro Phe Arg Leu Pro Pro Arg Leu
65                  70                  75                  80
Ala Leu Arg Leu Arg Val Thr Ala Glu His Leu Ala Arg Leu Arg Leu
                85                  90                  95
Arg Arg Ala Gly Gly Glu Gly Ala Pro Lys Pro Pro Ala Thr Pro Ala
            100                 105                 110
Thr Pro Ala Thr Pro Ala Thr Pro Ala Thr Pro
            115                 120                 125
```

(2) INFORMATION FOR SEQ ID NO:32:

(i) SEQUENCE CHARACTERISTICS:
        (A) LENGTH: 73 amino acids
        (B) TYPE: amino acid (C) STRANDEDNESS: single
        (D) TOPOLOGY: linear (ii) MOLECULE TYPE: protein (xi) SEQUENCE DESCRIPTION: SEQ ID NO:32:

Ala Arg Val Arg Phe Ser Pro His Val Arg Val Arg His Leu Val Val
1               5                   10                  15

Trp Ala Ser Ala Ala Arg Leu Ala Arg Arg Gly Ser Trp Ala Arg Glu
                20                  25                  30

Arg Ala Asp Arg Ala Arg Phe Arg Arg Val Ala Glu Ala Glu Ala
            35                  40                  45

Val Ile Gly Pro Cys Leu Gly Pro Glu Ala Arg Ala Arg Ala Leu Ala
        50                  55                  60

Arg Gly Ala Gly Pro Ala Asn Ser Val
65                  70

(2) INFORMATION FOR SEQ ID NO:33:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Met Ala Arg Arg Arg Arg His Arg Gly Pro Arg Arg Pro Arg Pro
1               5                   10                  15

Pro Gly Pro Thr Gly Ala Val Pro Thr Ala Gln Ser Gln Val Thr Ser
                20                  25                  30

Thr Pro Asn Ser Glu Pro Val Val Arg Ser Ala Pro Ala Ala Pro
            35                  40                  45

Pro Pro Pro Pro Ala Gly Gly Pro Pro Pro Ser Cys Ser Leu Leu Leu
        50                  55                  60

Arg Gln Trp Leu Gln Val Pro Glu Ser Ala Ser Asp Asp Asp Asp
65                  70                  75                  80

Asp Asp Trp Pro Asp Ser Pro Pro Glu Pro Ala Pro Glu Ala Arg
            85                  90                  95

Pro Thr Ala Ala Ala Pro Arg Pro Arg Ser Pro Pro Gly Ala Gly
                100                 105                 110

Pro Gly Gly Gly Ala Asp Pro Ser His Pro Pro Ser Arg Pro Phe Arg
        115                 120                 125

Leu Pro Pro Arg Leu Ala Leu Arg Leu Arg Val Thr Ala Glu His Leu
        130                 135                 140

Ala Arg Leu Arg Leu Arg Arg Ala Gly Gly Glu Gly Ala Pro Glu Pro
145                 150                 155                 160

Pro Ala Thr Pro Ala Thr Pro Ala Thr Pro Ala Thr Pro Ala Thr Pro
                165                 170                 175

Ala Thr Pro (2) INFORMATION FOR SEQ ID NO:34:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Ala Arg Val Arg Phe Ser Pro His Val Arg Arg His Leu Val Val
1               5                   10                  15

Trp Ala Ser Ala Ala Arg Leu Ala Arg Arg Gly Ser Trp Ala Arg Glu
                20                  25                  30

Arg Ala Asp Arg Ala Arg Phe Arg Arg Val Ala Glu Ala Glu Ala
                35                  40                  45

Val Ile Gly Pro Cys Leu Gly Lys Glu Ala Arg Ala Arg Ala Leu Ala
        50                  55                  60

Arg Gly Ala Gly Pro Ala Asn Ser Val
65                  70

(2) INFORMATION FOR SEQ ID NO:35:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Met Asp Glu Tyr Asp Asp Ala Ala Asp Ala Ala Gly Asp Arg Ala Pro
1               5                   10                  15

Gly Met (2) INFORMATION FOR SEQ ID NO:36:

(i) SEQUENCE CHARACTERISTICS:
        (A) LENGTH: 1327 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
TTTAAAGTCG CGGCGGCGCA GCCCGGCCCC CCGCGGCCGA GACGAGCGAG TTAGACAGGC      60
AAGCACTACT CGCCTCTGCA CGCACATGCT TGCCTGTCAA ACTCTACCAC CCCGGCACGC     120
TCTCTGTCTC CATGGCCCGC CGCCGCCGCC ATCGCGGCCC CCGCCGCCCC CGGCCGCCCG     180
GGCCCACGGG CGCCGTCCCA ACCGCACAGT CCCAGGTAAC CTCCACGCCC AACTCGGAAC     240
CCGCGGTCAG GAGCGCGCCC GCGGCCGCCC CGCCGCCGCC CCCCGCCAGT GGGCCCCCGC     300
CTTCTTGTTC GCTGCTGCTG CGCCAGTGGC TCCACGTTCC CGAGTCCGCG TCCGACGACG     360
ACGATGACGA CGACTGGCCG GACAGCCCCC CGCCCGAGCC GGCGCCAGAG GCCCGGCCCA     420
CCGCCGCCGC CCCCCGCCCC CACCGCCCGG CGCGGGCCCG GGGGCGGGG  CTAACCCCTC     480
CCACCCCCCC TCACGCCCCT TCCGCCTTCC GCCGCGCCTC GCCCTCCGCC TGCGCGTCAC     540
CGCAGAGCAC CTGGCGCGCC TGCGCCTGCG ACGCGCGGGC GGGGAGGGGG CGCCGGAGCC     600
CCCCGCGACC CCCGCGACCC CCGCGACCCC CGCGACCCCC GCGACCCCCG CGACCCCCGC     660
GACCCCCGCG ACCCCCGCGA CCCCCGCGAC CCCCGCGCGG GTGCGCTTCT CGCCCCACGT     720
CCGGGTGCGC CACCTGGTGG TCTGGGCCTC GGCCGCCCGC CTGGCGCGCC GCGGCTCGTG     780
GGCCCGCGAG CGGGCCGACC GGGCTCGGTT CCGGCGCCGG GTGGCGGAGG CCGAGGCGGT     840
CATCGGGCCG TGCCTGGGGC CCGAGGCCCG TGCCCGGGCC CTGGCCCGCG GAGCCGGCCC     900
```

```
GGCGAACTCG GTCTAACGTT ACACCCGAGG CGGCCTGGGT CTTCCGCGGA GCTCCCGGGA      960

GCTCCGCACC AAGCCGCTCT CCGGAGAGAC GATGGCAGGA GCCGCGCATA TATACGCTGG     1020

GAGCCGGCCC GCCCCCGAGG CGGGCCCGCC CTCGGAGGGC GGGACTGGCC AATCGGCGGC     1080

CGCCAGCGCG GCGGGCCCG GCCAACCAGC GTCCGCCGAG TCTTCGGGGC CCGGCCCACT      1140

GGGCGGGAGT TACCGCCCAG TGGGCCGGGC CGCCCACTTC CCGGTATGGT AATTAAAAAC    1200

TTACAAGAGG CCTTGTTCCG CTTCCCGGTA TGGTAATTAG AAACTCATTA ATGGGCGGCC    1260

CCGGCCGCCC TTCCCGCTTC CGGCAATTCC CGCGGCCCTT AATGGGCAAC CCCGGTATTC    1320

CCCGCCT                                                              1327

(2) INFORMATION FOR SEQ ID NO:37:

(i) SEQUENCE CHARACTERISTICS:
        (A) LENGTH: 1292 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

TTTAAAGCGG TGGCGGCGGG CAGCCCGGGC CCCCCGCCGA GACTAGCGAG TTAGACAGGC       60

AAGCACTACT CGCCTCTGCA CGCACATGCT TGCCTGTCAA ACTCTACCAC CCCGGCACGC      120

TCTCTGTCTC CATGGCCCGC CGCCGCCGCC ATCGCGGCCC CCGCCGCCCC CGGCCGCCCG      180

GGCCCACGGG CGCCGTCCCA ACCGCACAGT CCCAGGTAAC CTCCACGCCC AACTCGGAAC      240

CCGCGGTCAG GAGCGCGCCC GCGGCCGCCC CGCCGCCGCC CCCCGCCGGT GGGCCCCCGC      300

CTTCTTGTTC GCTGCTGCTG CGCCAGTGGC TCCACGTTCC CGAGTCCGCG TCCGACGACG      360

ACGATGACGA CGACTGGCCG GACAGCCCCC CGCCCGAGTC GGCGCCAGAG GCCCGGCCCA      420

CCGCCGCCGC CCCCCGCCCC CGGGCCCCC ACCGCCCGGC GTGGGCCCGG GGGCGGGGC       480

TGACCCCTCC CACCCCCCCT CGCGCCCCTT CCGCCTTCCG CCGCGCCTCG CCCTCCGCCT      540

GCGCGTCACC GCGGAGCACC TGGCGCGCCT GCGCCTGCGA CGCGCGGGCG GGGAGGGGGC      600

GCCGGAGCCC CCCGCGACCC CCGCGACCCC CGCGACCCCC GCGACCCCCG CGACCCCCGC      660

GACCCCCGCG CGGGTGCGCT TCTCGCCCCA CGTCCGGGTG CGCCACCTGG TGGTCTGGGC      720

CTCGGCCGCC CGCCTGGCGC GCCGCGGCTC GTGGGCCCGC GAGCGGGCCG ACCGGGCTCG      780

GTTCCGGCGC CGGGTGGCGG AGGCCGAGGC GGTCATCGGG CCGTGCCTGG GGCCCGAGGC      840

CCGTGCCCGG GCCCTGGCCC GCGGAGCCGG CCCGGCGAAC TCGGTCTAAC GTTACACCCG      900

AGGCGGCCTG GGTCTTCCGC GGAGCTCCCG GGAGCTCCGC ACCAAGCCGC TCTCCGGAGA      960

GACGATGGCA GGAGCCGCGC ATATATACGC TTGGAGCCAG CCCGCCCTCA CAGGGCGGGC    1020

CGGGCGGGAC TGGCCAATCG GCGGCCGCCA GCGCGGCGGG GCCCGGCCAA CCAGCGTCCG    1080

CCGAGTCTTC GGGGCCCGGC CCATTGGGCG GGAGTTACCG CCCAATGGGC CGGGCCGCCC    1140

ACTTCCCGGT ATGGTAATTA AAAACTTGCA AGAGGCCTTG TTCCGCTTCC CGGTATGGTA    1200

ATTAGAAACT CATTAATGGG CGGCCCCGGC CGCCCTTCCC GCTTCCGGCA ATTCCCGCGG    1260

CCCTTAATGG GCAACCCCGG TATTCCCCGC CT                                  1292

(2) INFORMATION FOR SEQ ID NO:38:

(i) SEQUENCE CHARACTERISTICS:
        (A) LENGTH: 1280 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
TTTAAAGTCA CAGCGGCGGG CAGCCCCCCC GCGGCCGAGA CTAGCGAGTT AGACAGGCAA      60

GCACTACTCG CCTCTGCACG CACATGCTTG CCTGTCAAAC TCTACCACCC CGGCACGCTC     120

TCTGTCTCCA TGGCCCGCCG CCGCCGCCGC CATCGCGGCC CCCGCCGCCC CCGGCCGCCC     180

GGGCCCACGG GCGCGGTCCC AACCGCACAG TCCCAGGTAA CCTCCACGCC CAACTCGGAA     240

CCCGTGGTCA GGAGCGCGCC CGCGGCCGGT GGGCCCCCGC CTTCTTGTTC GCTGCTGCTG     300

CGCCAGTGGC TCCACGTTCC CGAGTCCGCG TCCGACGACG ACGATGACGA CGACTGGCCG     360

GACAGCCCCC CGCCCGAGCC GGCGCCAGAG GCCCGGCCCA CCGCCGCCGC CCCCCGCCCC     420

CACCGCCCGG CGCGGGCCCG GGGGCGGGG CTAACCCCTC CCACCCCCC TCACGCCCCT     480

TCCGCCTTCC GCCGCGCCTC GCCCTCCGCC TGCGCGTCAC CGCGGAGCAC CTGGCGCGCC     540

TGCGCCTGCG ACGCGCGGGC GGGGAGGGGG CGCCGAAGCC CCCCGCGACC CCCGCGACCC     600

CCGCGACCCC CGCGACCCCC GCGACCCCCG CGACCCCCGC GACCCCGCG CGGGTGCGCT     660

TCTCGCCCCA CGTCCGGGTG CGCCACCTGG TGGTCTGGGC CTCGGCCGCC CGCCTGGCGC     720

GCCGCGGCTC GTGGGCCCGC GAGCGGGCCG ACCGGGCTCG GTTCCGGCGC CGGGTGGCGG     780

AGGCCGAGGC GGTCATCGGG CCGTGCCTGG GGCCCGAGGC CCGTGCCCGG GCCCTGGCCC     840

GCGGAGCCGG CCCGGCGAAC TCGGTCTAAC GTTACACCCG AGGCGGCCTG GGTCTTCCGC     900

GGAGCTCCCG GGAGCTCCAC ACCAAGCCGC TCTCCGGAGA GACGATGGCA GGAGCCGCGC     960

ATATATACGC TGGGAGCCGG CCCGCCCCCG AGGCGGGCCC GCCCTCGGAG GGCGGGACTG    1020

GCCAATCGGC GGCCGCCAGC GCGGCGGGGC CCGGCCAACC AGCGTCCGCC GAGTCGTCGG    1080

GGCCCGGCCC ACTGGGCGGT AACTCCCGCC CAGTGGGCCG GGCCGCCCAC TTCCCGGTAT    1140

GGTAATTAAA AACTTGCAAG AGGCCTTGTT CCGCTTCCCG GTATGGTAAT TAGAAACTCA    1200

TTAATGGGCG GCCCCGGCCG CCCTTCCCGC TTCCGGCAAT TCCCGCGGCC CTTAATGGGC    1260

AACCCCGGTA TTCCCCGCCT                                                1280
```

(2) INFORMATION FOR SEQ ID NO:39:

(i) SEQUENCE CHARACTERISTICS:
        (A) LENGTH: 1300 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

```
TTTAAAGCGC GGCGGCGGGC AGCCCCCCCG CGGCCGAGAC TAGCGAGTTA GACAGGCAAG      60

CACTACTCGC CTCTGCACGC ACATGCTTGC CTGTCAAACT CTACCACCCC GGCACGCTCT     120

CTGTCTCCAT GGCCCGCCGC CGCCGCCGCC ATCGCGGCCC CCGCCGCCCC GGCCGCCCG     180

GGCCCACGGG CGCGGTCCCA ACCGCACAGT CCCAGGTAAC CTCCACGCCC AACTCGGAAC     240

CCGTGGTCAG GAGCGCGCCC GCGGCCGCCC CGCCGCCGCC CCCGCCGGT GGGCCCCCGC     300

CTTCTTGTTC GCTGCTGCTG CGGCAGTGGC TCCAGGTTCC GGAGTCCGCG TCCGACGACG     360

ACGATGACGA CGACTGGCCG GACAGCCCCC CGCCCGAGCC GGCGCCAGAG GCCCGGCCCA     420
```

```
CCGCCGCCGC CCCCCGCCCC CACCGCCCGG CGCGGGCCCA GGGGGCGGGG CTGACCCCTC    480

CCACCCCCCC TCACGCCCCT TCCGCCTTCC GCCGCGCCTC GCCCTCCGCC TGCGCGTCAC    540

CGCAGAGCAC CTGGCGCGCC TGCGCCTGCG ACGCGCGGGC GGGGAGGGGG CGCCGGAGCC    600

CCCCGCGACC CCCGCGACCC CCGCGACCCC CGCGACCCCC GCGACCCCCG CGACCCCCGC    660

GACCCCCGCG CGGGTGCGCT TCTCGCCCCA CGTCCGGGTG CGCCACCTGG TGGTCTGGGC    720

CTCGGCCGCC CGCCTGGCGC GCCGCGGCTC GTGGGCCCGC GAGCGGGCCG ACCGGGCTCG    780

GTTCCGGCGC CGGGTGGCGG AGGCCGAGGC GGTCATCGGG CCGTGCCTGG CCCCAAGGC     840

CCGCGCCCGG GCCCTGGCCC GCGGAGCCGG CCCGGCGAAC TCGGTCTAAC GTTACACCCG    900

AGGCGGCCTG GGTCTTCCGC GGAGCTCCCG GGAGCTCCAC ACCAAGCCGC TCTCCGGAGA    960

GACGATGGCA GGAGCCGCGC ATATATACGC TGGGAGCCGG CCCGCCCCCG AGGCGGGCCC   1020

GCCCTCGGAG GGCGGGACTG GCCAATCGGC GGCCGCCAGC GCGGCGGGGC CCGGCCAACC   1080

AGCGTCCGCC GAGTCGTCGG GGCCCGGCCC ACTGGGCGGT AACTCCCGCC CAGTGGGCCG   1140

GGCCGCCCAC TTCCCGGTAT GGTAATTAAA AACTTGCAAG AGGCCTTGTT CCGCTTCCCG   1200

GTATGGTAAT TAGAAACTCA TTAATGGGCG GCCCCGGCCG CCCTTCCCGC TTCCGGCAAT   1260

TCCCGCGGCC CTTAATGGGC AACCCCGGTA TTCCCCGCCT                         1300

(2) INFORMATION FOR SEQ ID NO:40:

(i) SEQUENCE CHARACTERISTICS:
        (A) LENGTH: 264 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

Met Ala Arg Arg Arg His Arg Gly Pro Arg Arg Pro Arg Pro
1               5                   10                  15

Gly Pro Thr Gly Ala Val Pro Thr Ala Gln Ser Gln Val Thr Ser Thr
            20                  25                  30

Pro Asn Ser Glu Pro Ala Val Arg Ser Ala Pro Ala Ala Pro Pro
        35                  40                  45

Pro Pro Pro Ala Ser Gly Pro Pro Ser Cys Ser Leu Leu Leu Arg
    50                  55                  60

Gln Trp Leu His Val Pro Ala Glu Ser Ala Ser Asp Asp Asp Asp
65                  70                  75                  80

Asp Asp Trp Pro Asp Ser Pro Pro Glu Pro Ala Pro Glu Ala Arg
                85                  90                  95

Pro Thr Ala Ala Ala Pro Arg Pro Arg Ser Pro Pro Gly Ala Gly
            100                 105                 110

Pro Gly Gly Gly Ala Asn Pro Ser His Pro Pro Ser Arg Pro Phe Arg
            115                 120                 125

Leu Pro Pro Arg Leu Ala Leu Arg Leu Arg Val Thr Ala Glu His Leu
            130                 135                 140

Ala Arg Leu Arg Leu Arg Arg Ala Gly Gly Glu Gly Ala Pro Glu Pro
145                 150                 155                 160

Pro Ala Thr Pro Ala Thr Pro Ala Thr Pro Ala Thr Pro Ala Thr Pro
                165                 170                 175

Ala Thr Pro Ala Thr Pro Ala Thr Pro Ala Thr Pro Ala Thr Pro Ala
                180                 185                 190
```

-continued

```
Arg Val Arg Phe Ser Pro His Val Arg Val His Leu Val Val Trp
        195                 200                 205
Ala Ser Ala Ala Arg Leu Ala Arg Arg Gly Ser Trp Ala Glu Arg
        210                 215                 220
Ala Asp Arg Ala Arg Phe Arg Arg Val Ala Glu Ala Glu Ala Val
225                 230                 235                 240
Ile Gly Pro Cys Leu Gly Pro Glu Ala Arg Ala Arg Ala Leu Ala Arg
                245                 250                 255
Gly Ala Gly Pro Ala Asn Ser Val
                260
```

(2) INFORMATION FOR SEQ ID NO:41:

(i) SEQUENCE CHARACTERISTICS:
        (A) LENGTH: 355 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
Met Ala Arg Arg Arg Arg His Arg Gly Pro Arg Arg Pro Arg Pro Pro
1               5                   10                  15
Gly Pro Thr Gly Ala Val Pro Thr Ala Gln Ser Gln Val Thr Ser Thr
                20                  25                  30
Pro Asn Ser Glu Pro Ala Val Arg Ser Ala Pro Ala Ala Pro Pro
            35                  40                  45
Pro Pro Pro Ala Gly Gly Pro Pro Ser Cys Ser Leu Leu Leu Arg
    50                  55                  60
Gln Trp Leu His Val Pro Glu Ser Ala Ser Asp Asp Asp Asp Asp
65                  70                  75                  80
Asp Trp Pro Asp Ser Pro Pro Glu Ser Ala Pro Glu Ala Arg Pro
                85                  90                  95
Thr Ala Ala Pro Arg Pro Pro Gly Pro His Arg Pro Ala Trp Ala
            100                 105                 110
Arg Gly Ala Gly Leu Thr Pro Pro Thr Pro Pro Arg Ala Pro Ser Ala
        115                 120                 125
Phe Arg Arg Ala Ser Pro Ser Ala Cys Ala Ser Pro Arg Ser Thr Trp
130                 135                 140
Arg Ala Cys Ala Cys Asp Ala Arg Ala Gly Arg Gly Arg Ser Pro
145                 150                 155                 160
Pro Arg Pro Pro Arg Pro Pro Arg Pro Pro Arg Pro Arg Pro Pro
                165                 170                 175
Arg Gly Cys Ala Ser Arg Pro Thr Ser Gly Cys Ala Thr Trp Trp Ser
            180                 185                 190
Gly Pro Arg Pro Ala Trp Arg Ala Ala Arg Gly Pro Ala Ser
        195                 200                 205
Gly Pro Thr Gly Leu Gly Ser Gly Ala Gly Trp Arg Arg Pro Arg Arg
        210                 215                 220
Ser Ser Gly Arg Ala Trp Gly Pro Arg Val Pro Gly Pro Trp Pro
225                 230                 235                 240
Ala Glu Pro Ala Arg Arg Thr Arg Ser Asn Val Thr Pro Glu Ala Ala
                245                 250                 255
Trp Val Phe Arg Gly Ala Pro Gly Ser Ser Ala Pro Ser Arg Ser Pro
            260                 265                 270
```

Glu Arg Arg Trp Gln Glu Pro Arg Ile Tyr Thr Leu Gly Ala Ser Pro
            275                 280                 285

Pro Ser Gln Gly Gly Pro Pro Arg Gly Arg Asp Trp Pro Ile Gly Gly
        290                 295                 300

Arg Gln Arg Gly Gly Ala Arg Pro Thr Ser Val Arg Val Phe Gly
305                 310                 315                 320

Ala Arg Pro Ile Gly Arg Glu Leu Pro Pro Asn Gly Pro Gly Arg Pro
                325                 330                 335

Leu Pro Gly Met Val Ile Lys Asn Leu Gln Glu Ala Leu Phe Arg Phe
            340                 345                 350

Pro Val Trp
        355

(2) INFORMATION FOR SEQ ID NO:42:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

Met Ala Arg Arg Arg Arg His Arg Gly Pro Arg Arg Pro Arg Pro
1               5                  10                  15

Pro Gly Pro Thr Gly Ala Val Pro Thr Ala Gln Ser Gln Val Thr Ser
            20                  25                  30

Thr Pro Asn Ser Glu Pro Val Val Arg Ser Ala Pro Ala Ala Gly Gly
        35                  40                  45

Pro Pro Pro Ser Cys Ser Leu Leu Leu Arg Gln Trp Leu His Val Pro
    50                  55                  60

Glu Ser Ala Ser Asp Asp Asp Asp Asp Trp Pro Asp Ser Pro
65                  70                  75                  80

Pro Pro Glu Pro Ala Pro Glu Ala Arg Pro Thr Ala Ala Ala Pro Arg
                85                  90                  95

Pro Arg Ser Pro Pro Gly Ala Gly Pro Gly Gly Ala Asn Pro
            100                 105                 110

Ser His Pro Pro Ser Arg Pro Phe Arg Leu Pro Pro Arg Leu Ala Leu
        115                 120                 125

Arg Leu Arg Val Thr Ala Glu His Leu Ala Arg Leu Arg Arg
    130                 135                 140

Ala Gly Gly Glu Gly Ala Pro Lys Pro Pro Ala Thr Pro Ala Thr Pro
145                 150                 155                 160

Ala Thr Pro Ala Thr Pro Ala Thr Pro Ala Thr Pro Ala Arg Val Arg
                165                 170                 175

Phe Ser Pro His Val Arg Val Arg His Leu Val Val Trp Ala Ser Ala
            180                 185                 190

Ala Arg Leu Ala Arg Arg Gly Ser Trp Ala Arg Glu Arg Ala Asp Arg
        195                 200                 205

Ala Arg Phe Arg Arg Arg Val Ala Glu Ala Glu Ala Val Ile Gly Pro
    210                 215                 220

Cys Leu Gly Pro Glu Ala Arg Ala Arg Ala Leu Ala Arg Gly Ala Gly
225                 230                 235                 240

Pro Ala Asn Ser Val
                245

(2) INFORMATION FOR SEQ ID NO:43:

(i) SEQUENCE CHARACTERISTICS:
      (A) LENGTH: 252 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:43:

```
Met Ala Arg Arg Arg Arg His Arg Gly Pro Arg Pro Arg Pro
1               5                  10                  15

Pro Gly Pro Thr Gly Ala Val Pro Thr Ala Gln Ser Gln Val Thr Ser
            20                  25                  30

Thr Pro Asn Ser Glu Pro Val Val Arg Ser Ala Pro Ala Ala Ala Pro
            35                  40                  45

Pro Pro Pro Ala Gly Gly Pro Pro Pro Ser Cys Ser Leu Leu Leu
50                  55                  60

Arg Gln Trp Leu Gln Val Pro Glu Ser Ala Ser Asp Asp Asp Asp
65                  70                  75                  80

Asp Asp Trp Pro Asp Ser Pro Pro Glu Pro Ala Pro Glu Ala Arg
                85                  90                  95

Pro Thr Ala Ala Ala Pro Arg Pro Arg Ser Pro Pro Pro Gly Ala Gly
                100                 105                 110

Pro Gly Gly Gly Ala Asp Pro Ser His Pro Pro Ser Arg Pro Phe Arg
            115                 120                 125

Leu Pro Pro Arg Leu Ala Leu Arg Leu Arg Val Thr Ala Glu His Leu
130                 135                 140

Ala Arg Leu Arg Leu Arg Arg Ala Gly Gly Glu Gly Ala Pro Glu Pro
145                 150                 155                 160

Pro Ala Thr Pro Ala Thr Pro Ala Thr Pro Ala Thr Pro Ala Thr Pro
                165                 170                 175

Ala Thr Pro Ala Arg Val Arg Phe Ser Pro His Val Arg Val Arg His
                180                 185                 190

Leu Val Val Trp Ala Ser Ala Ala Arg Leu Ala Arg Arg Gly Ser Trp
            195                 200                 205

Ala Arg Glu Arg Ala Asp Arg Ala Arg Phe Arg Arg Val Ala Glu
210                 215                 220

Ala Glu Ala Val Ile Gly Pro Cys Leu Gly Lys Glu Ala Arg Ala Arg
225                 230                 235                 240

Ala Leu Ala Arg Gly Ala Gly Pro Ala Asn Ser Val
                245                 250
```